(12) United States Patent
Golub et al.

(10) Patent No.: US 6,949,342 B2
(45) Date of Patent: Sep. 27, 2005

(54) PROSTATE CANCER DIAGNOSIS AND OUTCOME PREDICTION BY EXPRESSION ANALYSIS

(75) Inventors: Todd R. Golub, Newton, MA (US); Phillip G. Febbo, Jamaica Plain, MA (US); Kenneth N. Ross, Boston, MA (US); William R. Sellers, Chestnut Hill, MA (US)

(73) Assignees: Whitehead Institute for Biomedical Research, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 10/325,457

(22) Filed: Dec. 19, 2002

(65) Prior Publication Data

US 2003/0152980 A1 Aug. 14, 2003

Related U.S. Application Data

(60) Provisional application No. 60/343,448, filed on Dec. 21, 2001.

(51) Int. Cl.[7] .......................... C12Q 1/68; G01N 33/53
(52) U.S. Cl. ............................................ 435/6; 435/7.1
(58) Field of Search .......................... 435/6, 7.1, 7.9, 435/91.1, 91.2; 536/23.1, 24.3, 24.33

(56) References Cited

U.S. PATENT DOCUMENTS

| | | | |
|---|---|---|---|
| 6,476,207 B1 * | 11/2002 | Zhang et al. | 536/23.1 |
| 2002/0068036 A1 * | 6/2002 | Hevezi et al. | 424/9.2 |
| 2003/0013097 A1 * | 1/2003 | Welsh et al. | 435/6 |
| 2003/0113762 A1 | 6/2003 | Warrington | |

OTHER PUBLICATIONS

Constantine, L. and Harrington, C., "Use of GeneChip High–Density Oligonucleotide Arrays for Gene Expression Monitoring," *Life Science News*, pp. 11–14 (1998).
Schena, M., et al., "Parallel Human Genome Analysis: Microarray–Based Expression Monitoring of 1000 Genes," *Proceedings of the National Academy of Sciences U.S.A.*, 93:10614–10619 (1996).
Xu, J., et al., "Identification of Differentially Expressed Genes In Human Prostate Cancer Using Subtraction and Microarray," *Cancer Research*, 60:1677–1682 (2000).
Dhanasekaran, S.M., et al., "Delineation of Prognostic Biomarkers in Prostate Cancer," *Nature*, 412:822–826 (2001).
Eklöv, S., et al., "Lack of the Latent Transforming Growth Factor β Binding Protein in Malignant, But Not Benign Prostatic Tissue," *Cancer Research*, 53:3193–3197 (1993).
Jensen, S.L., et al., "Increased Levels of nm23 H1/Nucleoside Diphosphate Kinase A mRNA Associated with Adenocarcinoma of the Prostate," *World Journal of Urology*, 14: S21–S25 (1996).
Myers, R.B., et al., "Expression of nm23–H1 in Prostatic Intraepithelial Neoplasia and Adenocarcinoma," *Human Pathology*, 27:1021–1024 (1996).
Nelson, W.G., et al., "The Molecular Pathogenesis of Prostate Cancer: Implications for Prostate Cancer Prevention," *Urology*, 57 (Supp. 4A): 39–45 (2001).
Poczateck, R.B., et al., "Ep–CAM Levels in Prostatic Adenocarcinoma and Prostatic Intraepithelial Neoplasia," *The Journal of Urology*, 162: 1462–1466 (1999).
Saverio, B., et al., "Tumor Progression is Accompanied by Significant Changes in the Levels of Expression of Polyamine Metabolism Regulatory Genes and Clusterin (Sulfated Glycoprotein 2) in Human Prostate Cancer Specimens," *Cancer Research*, 60:28–34 (2000).
Sellers, W.R., "Analysis of Gene Expression in Prostate Cancer," Institutes of Health Directors' Challenge Group Presentation, Apr., 2001.
Silver, D.A., et al., "Prostate–specific Membrane Antigen Expression in Normal and Malignant Human Tissues," *Clinical Cancer Research*, 3:81–85 (1997).
Welsh, J.B., et al., "Analysis of Gene Expression Identifies Candidate Markers and Pharmacological Targets in Prostate Cancer," *Cancer Research*, 61:5974–5978 (2001).
Yang, M., et al., "Differential Expression and Androgen Regulation of the Human Selenium–Binding Protein Gene hSP56 in Prostate Cancer Cells," *Cancer Research*, 58:3150–3153 (1998).
Chetcuti, A., et al., "Loss of Annexin II Heavy and Light Chains in Prostate Cancer and Its Precursors," *Cancer Research*, 61:6331–6334 (2001).
Cornford, P.A., et al., "Heat Shock Protein Expression Independently Predicts Clinical Outcome in Prostate Cancer," *Cancer Research*, 60:7099–7105 (2000).
Djonov, V., et al., "Transforming Growth Factor–β3 is Expressed in Nondividing Basal Epithelial Cells in Normal Human Prostate and Benign Prostatic Hyperplasia, and Is No Longer Detectable in Prostate Carcinoma," *The Prostate*, 31:103–109 (1997).

* cited by examiner

*Primary Examiner*—Kenneth R. Horlick
(74) *Attorney, Agent, or Firm*—Fish & Neave IP Group

(57) ABSTRACT

Methods identifying prostate cancer, methods for prognosing and diagnosing prostate cancer, methods for identifying a compound that modulates prostate cancer development, methods for determining the efficacy of a prostate cancer therapy, and oligonucleotide microarrays containing probes for genes involved in prostate cancer development are described.

7 Claims, 74 Drawing Sheets

(2 of 74 Drawing Sheet(s) Filed in Color)

| Group | | Study Group Patient's | Pop (95-97) | Study Group vs Pop | Recurred | No Recurrence | Recur vs non-recur |
|---|---|---|---|---|---|---|---|
| # Patients | | 52 | 393 | | 8 | 13 | |
| Age | Median | 58.5 | 61 | 0.32 | 58.5 | 60.0 | 0.74 |
| | Range | 47-72 | 40-79 | | 51-72 | 47-72 | |
| | <60 | 27 (52%) | 168 (43%) | | 5 (63%) | 6 (46%) | |
| | 60-65 | 11 (21%) | 104 (27%) | | 2 (25%) | 1 (8%) | |
| | ≥65 | 14 (27%) | 120 (31%) | | 1 (12%) | 6 (46%) | |
| | Unknown | | 1 | | | | |
| PSA | Median | 6.3 | 6.7 | 0.62 | 6.8 | 6.3 | 0.64 |
| | Range | 1.0–27.8 | 0.7–46.0 | | 5.0-24.3 | 3.6-18.0 | |
| | <5 | 14 (27%) | 70 (22%) | | 0 | 3 (23%) | |
| | 5-10 | 23 (45%) | 176 (55%) | | 5 (63%) | 5 (38%) | |
| | ≥10 | 14 (27%) | 72 (22%) | | 3 (37%) | 5 (38%) | |
| | Unknown | 1 | 75 | | | | |
| Gleason Score | 2-6 | 19 (37%) | 190 (51%) | 0.10 | 2 (25%) | 6 (46%) | 0.45 |
| | 7 | 29 (56%) | 146 (39%) | | 5 (61%) | 6 (46%) | |
| | 8–10 | 4 (8%) | 34 (9%) | | 1 (12%) | 1 (8%) | |
| | Unknown | | 23 | | | | |
| Clinical Stage | T1-T2a | 38 (88%) | 285 (79%) | 0.10 | 5 (100%) | 10 (91%) | 1.00 |
| | T2b | 5 (12%) | 24 (7%) | | 0 | 9 (9%) | |
| | ≥T2c | 0 | 50 (14%) | | 0 | 0 | |
| | Unknown | 9 | 34 | | 3 | 2 | |
| Pathologic Stage | T2a | 7 (13%) | 49 (15%) | 0.15 | 1 (13%) | 2 (15%) | 0.90 |
| | T2b | 25 (48%) | 189 (58%) | | 4 (50%) | 5 (38%) | |
| | T3a | 16 (31%) | 74 (23%) | | 2 (25%) | 4 (31%) | |
| | T3b | 4 (8%) | 12 (4%) | | 1 (13%) | 2 (15%) | |
| | T4a | 0 | 2 (1%) | | 0 | 0 | |
| | Unknown | | 53 | | | | |
| Gland Volume | Median | 51.75 | 53.0 | 0.89 | 67.5 | 50.0 | 0.15 |
| | Range | 35-191 | 18-191 | | 35.5-191 | 35-169 | |
| | <45 cc | 14 (27%) | 85 (25%) | | 2 (25%) | 5 (38%) | |
| | 45-60 cc | 19 (37%) | 139 (41%) | | 0 | 5 (38%) | |
| | ≥60 cc | 19 (37%) | 116 (34%) | | 6 (75%) | 3 (23%) | |
| | Unknown | 0 | 53 | | | | |
| Extracapsular Extension | No | 32 (62%) | 239 (73%) | 0.10 | 5 (63%) | 7 (54%) | 1.00 |
| | Yes | 20 (38%) | 88 (27%) | | 3 (37%) | 6 (46%) | |
| | Unknown | | 66 | | | | |
| Seminal Vesicle Invasion | No | 49 (94%) | 315 (96%) | 0.44 | 7 (88%) | 12 (92%) | 1.00 |
| | Yes | 3 (6%) | 12 (4%) | | 1 (12%) | 1 (8%) | |
| | Unknown | | 66 | | | | |
| Positive | No | 39 (75%) | 283 (76%) | 0.86 | 5 (62%) | 7 (54%) | 1.00 |

FIG. 1

| | | | Genes upregulated in Normal prostate tissue compared to prostate tumors tissue | | | | |
|---|---|---|---|---|---|---|---|
| Label | Distinction | Distance | Desc | pearson corr Tumor | pearson corr Normal | Mean TN Ratio | Accession |
| 40282_s_at | normal | 0.8646274 | Cluster Incl. M84526:Human adipsin/complement factor D mRNA, complete cds /cds=(54,740) /gb=M84526 /gi=178625 /ug=Hs.155597 /len=1071 | -0.342 | -0.263 | 0.691208798 | 40282_s_at |
| 38406_f_at | normal | 0.8338151 | Cluster Incl. AI207842.a089h09.x1 Homo sapiens cDNA, 3 end /clone=IMAGE-1953089 /clone_end=3 /gb=AI207842 /gi=3769784 /ug=Hs.8272 /len=771 | -0.264 | -0.174 | 0.882732533 | 38406_f_at |
| 32598_at | normal | 0.8187385 | Cluster Incl. D83018:Homo sapiens mRNA for nel-related protein 2, complete cds /cds=(96,2546) /gb=D83018 /gi=1827484 /ug=Hs.79389 /len=3198 | 0.058 | -0.2 | 0.533962001 | 32598_at |
| 41288_at | normal | 0.8013052 | Cluster Incl. AL036744:DKFZp564I1663_r1 Homo sapiens cDNA, 5 end /clone=DKFZp564I1663 /clone_end=5 /gb=AL036744 /gi=5927888 /ug=Hs.236327 /len=617 | -0.133 | -0.297 | 1.049743237 | 41288_at |
| 38634_at | normal | 0.7762093 | Cluster Incl. M11433:Human cellular retinol-binding protein mRNA, complete cds /cds=(125,532) /gb=M11433 /gi=190947 /ug=Hs.101850 /len=716 | 0.024 | -0.296 | 0.602541647 | 38634_at |
| 556_s_at | normal | 0.7666016 | M96233 /FEATURE=expanded_cds /DEFINITION=HUMGSTM4A Human glutathione transferase class mu number 4 (GSTM4) gene, complete cds | -0.193 | -0.158 | 0.963395637 | 556_s_at |
| 1767_s_at | normal | 0.7556152 | X14885 /FEATURE=mRNA /DEFINITION=HSTGF31 H.sapiens gene for transforming growth factor-beta 3 (TGF-beta 3) exon 1 (and joined CDS) | 0.111 | 0.092 | 1.205721301 | 1767_s_at |
| 38028_at | normal | 0.7416515 | Cluster Incl. AL050152:Homo sapiens mRNA; cDNA DKFZp586K1220 (from clone DKFZp586K1220) /cds=UNKNOWN /gb=AL050152 /gi=4884363 /ug=Hs.7974 /len=2821 | 0 | -0.371 | 0.714265288 | 38028_at |
| 38044_at | normal | 0.7312475 | Cluster Incl. AF035283:Homo sapiens clone 23916 mRNA sequence /cds=UNKNOWN /gb=AF035283 /gi=2661034 /ug=Hs.8022 /len=2022 | -0.44 | -0.431 | 0.874062777 | 38044_at |
| 38087_s_at | normal | 0.7236925 | Cluster Incl. W72186:zd69b10.s1 Homo sapiens cDNA, 3 end /clone=IMAGE-345883 /clone_end=3 /gb=W72186 /gi=1382635 /ug=Hs.81256 /len=598 | -0.293 | -0.429 | 0.754224036 | 38087_s_at |

FIG. 2A

| Label | Distinction | Distance | Desc | pearson corr Tumor | pearson corr Normal | Mean TN Ratio | Accession |
|---|---|---|---|---|---|---|---|
| 38051_at | normal | 0.6961423 | Cluster Incl. X76220:H.sapiens MAL gene exon 1 (and joined CDS) /cds=(59,520) /gb=X76220 /gi=433225 /ug=Hs.80395 /len=1056 | | -0.375 | 0.879714869 | 38051_at |
| 33137_at | normal | 0.6717835 | Cluster Incl. Y13622:Homo sapiens mRNA for latent transforming growth factor-beta binding protein-4 /cds=(0,4763) /gb=Y13622 /gi=2190401 /ug=Hs.85087 /len=5031 | -0.123 | -0.372 | 0.967995629 | 33137_at |
| 39545_at | normal | 0.667826 | Cluster Incl. U22398:Human Cdk-inhibitor p57KIP2 (KIP2) mRNA, complete cds /cds=(260,1210) /gb=U22398 /gi=790247 /ug=Hs.106070 /len=1511 | 0 | -0.247 | 1.065142169 | 39545_at |
| 40856_at | normal | 0.6629694 | Cluster Incl. U29953:Human pigment epithelium-derived factor gene, complete cds /cds=(136,1224) /gb=U29953 /gi=1144298 /ug=Hs.173594 /len=1511 | -0.329 | -0.161 | 1.264180994 | 40856_at |
| 39315_at | normal | 0.6595787 | Cluster Incl. D13628:Human mRNA for KIAA0003 gene, complete cds /cds=(95,673) /gb=D13628 /gi=285988 /ug=Hs.2463 /len=3041 | -0.282 | -0.022 | 0.90928154 | 39315_at |
| 32206_at | normal | 0.6578734 | Cluster Incl. AB007920:Homo sapiens mRNA for KIAA0451 protein, complete cds /cds=(1482,2219) /gb=AB007920 /gi=3413863 /ug=Hs.18586 /len=6597 | 0.058 | -0.287 | 0.974909931 | 32206_at |
| 32243_g_at | normal | 0.6517518 | Cluster Incl. AL038340:DKFZp566K192_s1 Homo sapiens cDNA, 3 end /clone=DKFZp566K192 /clone_end=3 /gb=AL038340 /gi=5407591 /ug=Hs.1940 /len=746 | -0.369 | -0.448 | 0.875146984 | 32243_g_at |
| 31444_s_at | normal | 0.6500523 | Cluster Incl. M62895:Human lipocortin (LIP) 2 pseudogene mRNA, complete cds-like region /cds=UNKNOWN /gb=M62895 /gi=187145 /ug=Hs.166072 /len=1361 | -0.615 | -0.274 | 1.081769298 | 31444_s_at |
| 38950_r_at | normal | 0.6416278 | Cluster Incl. AJ005256:Homo sapiens mRNA for MMP-23 /cds=(38,1210) /gb=AJ005256 /gi=4468603 /ug=Hs.211819 /len=1246 | -0.051 | -0.37 | 0.907509394 | 38950_r_at |
| 769_s_at | normal | 0.6396087 | D00017 /FEATURE= /DEFINITION=HUMLIC Homo sapiens mRNA for lipocortin II, complete cds | -0.513 | -0.194 | 1.216348109 | 769_s_at |
| 40024_at | normal | 0.6356518 | Cluster Incl. D86640:Homo sapiens mRNA for stac, complete cds /cds=(39,1247) /gb=D86640 /gi=1799567 /ug=Hs.56045 /len=2963 | -0.351 | -0.375 | 0.777715303 | 40024_at |

FIG. 2B

| Label | Distinction | Distance | Desc | pearson corr Tumor | pearson corr Normal | Mean TN Ratio | Accession |
|---|---|---|---|---|---|---|---|
| 41504_s_at | normal | 0.6319174 | Cluster Incl. AF055376:Homo sapiens short form transcription factor C-MAF (c-maf) mRNA, complete cds /cds=(807,1928) /gb=AF055376 /gi=3335147 /ug=Hs.30250 /len=4246 | -0.214 | 0.244 | 1.45060811 | 41504_s_at |
| 33198_at | normal | 0.6257397 | Cluster Incl. AA206524:zq58b03.r1 Homo sapiens cDNA, 5 end /clone=IMAGE-645773 /clone_end=5 /gb=AA206524 /gi=1801905 /ug=Hs.9552 /len=848 | -0.246 | -0.251 | 1.243231577 | 33198_at |
| 39054_at | normal | 0.6205294 | Cluster Incl. X08020:Human mRNA for glutathione S-transferase subunit 4 (EC 2.5.1.18) /cds=(24,680) /gb=X08020 /gi=31923 /ug=Hs.117782 /len=1128 | -0.23 | -0.156 | 0.795846759 | 39054_at |
| 216_at | normal | 0.614769 | M98539 /FEATURE=exon /DEFINITION=HUMPDS03 Human prostaglandin D2 synthase gene, exon 7 | -0.474 | -0.121 | 2.865296326 | 216_at |
| 35742_at | normal | 0.6119738 | Cluster Incl. U95740:Human Chromosome 16 BAC clone CIT987SK-A-362G6 /cds=(0,1076) /gb=U95740 /gi=3417288 /ug=Hs.6349 /len=2516 | 0.024 | -0.333 | 1.046779683 | 35742_at |
| 39182_at | normal | 0.6071576 | Cluster Incl. U87947:Human hematopoietic neural membrane protein (HNMP-1) mRNA, complete cds /cds=(241,732) /gb=U87947 /gi=2358251 /ug=Hs.9999 /len=817 | 0 | -0.248 | 1.078845224 | 39182_at |
| 37203_at | normal | 0.6029024 | Cluster Incl. L07765:Human carboxylesterase mRNA, complete cds /cds=(67,1767) /gb=L07765 /gi=180949 /ug=Hs.76688 /len=1966 | 0 | -0.255 | 0.770709181 | 37203_at |
| 40607_at | normal | 0.5961886 | Cluster Incl. U97105:Homo sapiens N2A3 mRNA, complete cds /cds=(1336,3054) /gb=U97105 /gi=2967518 /ug=Hs.173381 /len=5407 | -0.077 | -0.315 | 0.988366336 | 40607_at |
| 37394_at | normal | 0.5915665 | Cluster Incl. J03507:Human complement protein component C7 mRNA, complete cds /cds=(0,2531) /gb=J03507 /gi=179715 /ug=Hs.78065 /len=3890 | 0.006 | 0.134 | 0.979167644 | 37394_at |
| 32076_at | normal | 0.5862052 | Cluster Incl. D83407:ZAKI-4 mRNA in human skin fibroblast, complete cds /cds=(204,782) /gb=D83407 /gi=1435039 /ug=Hs.156007 /len=3184 | 0.007 | -0.432 | 0.819865363 | 32076_at |
| 38322_at | normal | 0.573978 | Cluster Incl. AI093155:qa97g04.x1 Homo sapiens cDNA, 3 end /clone=IMAGE-1694742 /clone_end=3 /gb=AI093155 /gi=3432131 /ug=Hs.95420 /len=493 | -0.047 | 0.35 | 1.595101532 | 38322_at |

FIG. 2C

| Label | Distinction | Distance | Desc | pearson corr Tumor | pearson corr Normal | Mean TN Ratio | Accession |
|---|---|---|---|---|---|---|---|
| 38042_at | normal | 0.5691869 | Cluster Incl. X03674:Human mRNA for glucose-6-phosphate dehydrogenase (G6PD) /cds=(470,2017) /gb=X03674 /gi=31542 /ug=Hs.80206 /len=2625 | -0.158 | -0.301 | 0.8821169958 | 38042_at |
| 33362_at | normal | 0.5642287 | Cluster Incl. AF094521:Homo sapiens MSE55-related protein (UB1) mRNA, complete cds /cds=(0,764) /gb=AF094521 /gi=3834632 /ug=Hs.220056 /len=765 | -0.183 | -0.121 | 1.170674877 | 33362_at |
| 36601_at | normal | 0.55858 | Cluster Incl. M33308:Human vinculin mRNA, complete cds /cds=(50,3250) /gb=M33308 /gi=340236 /ug=Hs.75350 /len=5102 | -0.159 | -0.426 | 1.110387172 | 36601_at |
| 38338_at | normal | 0.5566991 | Cluster Incl. AI201108:qf69g07.x1 Homo sapiens cDNA, 3 end /clone=IMAGE-1755324 /clone_end=3 /gb=AI201108 /gi=3753714 /ug=Hs.9651 /len=756 | -0.415 | -0.378 | 1.080505478 | 38338_at |
| 36650_at | normal | 0.5559238 | Cluster Incl. D13639:Human mRNA for KIAK0002 gene, complete cds /cds=(269,1138) /gb=D13639 /gi=285990 /ug=Hs.75586 /len=6478 | -0.041 | -0.317 | 0.879132425 | 36650_at |
| 37573_at | normal | 0.5505459 | Cluster Incl. AF007150:Homo sapiens clone 23767 and 23782 mRNA sequences /cds=UNKNOWN /gb=AF007150 /gi=2852628 /ug=Hs.8025 /len=1444 | -0.32 | -0.417 | 0.977591304 | 37573_at |
| 36814_at | normal | 0.5496267 | Cluster Incl. AB029032:Homo sapiens mRNA for KIAA1109 protein, partial cds /cds=(0,5873) /gb=AB029032 /gi=5689554 /ug=Hs.6606 /len=6377 | -0.158 | -0.003 | 1.258203856 | 36814_at |
| 36780_at | normal | 0.5451067 | Cluster Incl. M25915:Human complement cytolysis inhibitor (CLI) mRNA, complete cds /cds=(198,1544) /gb=M25915 /gi=180619 /ug=Hs.75106 /len=1651 | -0.477 | -0.427 | 1.573337897 | 36780_at |
| 38740_at | normal | 0.5393807 | Cluster Incl. X79067:H.sapiens ERF-1 mRNA 3 end /cds=UNKNOWN /gb=X79067 /gi=483524 /ug=Hs.85155 /len=3922 | -0.354 | -0.29 | 0.9439629353 | 38740_at |
| 41388_at | normal | 0.5359967 | Cluster Incl. AF017418:Homo sapiens homeobox protein MEIS2 (MEIS2) mRNA, partial cds /cds=(0,376) /gb=AF017418 /gi=2394309 /ug=Hs.104105 /len=1879 | 0 | -0.038 | 0.9332180955 | 41388_at |
| 35776_at | normal | 0.5348017 | Cluster Incl. AF064243:Homo sapiens intersectin short form mRNA, complete cds /cds=(106,3768) /gb=AF064243 /gi=3859852 /ug=Hs.66392 /len=5272 | -0.103 | -0.222 | 0.778192148 | 35776_at |

FIG. 2D

| Label | Distinction | Distance | Desc | pearson corr Tumor | pearson corr Normal | Mean TN Ratio | Accession |
|---|---|---|---|---|---|---|---|
| 1897_at | normal | 0.5343011 | L07594 /FEATURE= /DEFINITION=HUMTGFB3C Human transforming growth factor-beta type III receptor (TGF-beta) mRNA, complete cds | 0 | -0.324 | 0.8868654531 | 1897_at |
| 38410_at | normal | 0.5323741 | Cluster Incl. X72964:H.sapiens mRNA for caltractin /cds=(47,565) /gb=X72964 /gi=441311 /ug=Hs.82794 /len=1087 | -0.483 | -0.282 | 1.258171916 | 38410_at |
| 35238_at | normal | 0.5321019 | Cluster Incl. AB000509:Homo sapiens mRNA for TRAF5, complete cds /cds=(54,1727) /gb=AB000509 /gi=2982670 /ug=Hs.29736 /len=3968 | -0.367 | -0.277 | 1.030274425 | 35238_at |
| 37225_at | normal | 0.5299581 | Cluster Incl. D79994:Human mRNA for KIAA0172 gene, partial cds /cds=(0,3923) /gb=D79994 /gi=1136403 /ug=Hs.77546 /len=4792 | -0.56 | -0.202 | 1.064119119 | 37225_at |
| 32695_at | normal | 0.5297692 | Cluster Incl. Z97632:dJ196E23.2 (HIV-1 transcriptional elongation factor TAT cofactor TAT-SF1) /cds=(111,2378) /gb=Z97632 /gi=2808417 /ug=Hs.171595 /len=2712 | -0.213 | -0.141 | 1.183176805 | 32695_at |
| 33396_at | normal | 0.529549 | Cluster Incl. U12472:Human glutathione S-transferase (GST phi) gene, complete cds /cds=(0,632) /gb=U12472 /gi=763404 /ug=Hs.226795 /len=757 | -0.256 | -0.074 | 1.706280535 | 33396_at |
| 39026_r_at | normal | 0.521492 | Cluster Incl. AF052114:Homo sapiens clone 23887 mRNA sequence /cds=UNKNOWN /gb=AF052114 /gi=3360421 /ug=Hs.112844 /len=2416 | -0.219 | -0.225 | 0.806402409 | 39026_r_at |
| 37405_at | normal | 0.5207971 | Cluster Incl. U29091:Human selenium-binding protein (hSBP) mRNA, complete cds /cds=(4,1422) /gb=U29091 /gi=1374791 /ug=Hs.7833 /len=1429 | -0.347 | -0.185 | 1.011399668 | 37405_at |
| 40419_at | normal | 0.5171321 | Cluster Incl. X85116:H.sapiens epb72 gene exon 1 /cds=(61,927) /gb=X85116 /gi=1161561 /ug=Hs.160483 /len=3035 | -0.177 | -0.474 | 1.056547462 | 40419_at |
| 33408_at | normal | 0.5164161 | Cluster Incl. AB023151:Homo sapiens mRNA for KIAA0934 protein, partial cds /cds=(0,4060) /gb=AB023151 /gi=4589511 /ug=Hs.227716 /len=5892 | -0.047 | -0.106 | 1.063794663 | 33408_at |
| 38291_at | normal | 0.5143506 | Cluster Incl. J00123:Human enkephalin gene /cds=(0,803) /gb=J00123 /gi=182098 /ug=Hs.93557 /len=804 | -0.44 | -0.063 | 0.670884219 | 38291_at |

FIG. 2E

| Label | Distinction | Distance | Desc | pearson corr Tumor | pearson corr Normal | Mean TN Ratio | Accession |
|---|---|---|---|---|---|---|---|
| 36119_at | normal | 0.5141662 | Cluster Incl. AF070648:Homo sapiens clone 24651 mRNA sequence /cds=UNKNOWN /gb=AF070648 /gi=3283922 /ug=Hs.74034 /len=1313 | -0.319 | -0.262 | 1.149919706 | 36119_at |
| 39551_at | normal | 0.5114553 | Cluster Incl. N98667:yy66d05.r1 Homo sapiens cDNA, 5 end /clone=IMAGE-278505 /clone_end=5 /gb=N98667 /gi=1270089 /ug=Hs.106826 /len=549 | -0.232 | -0.115 | 1.148523009 | 39551_at |
| 1664_at | normal | 0.5113992 | Insulin-Like Growth Factor 2 | -0.371 | -0.281 | 0.674169354 | 1664_at |
| 38120_at | normal | 0.510708 | Cluster Incl. U50928:Human autosomal dominant polycystic kidney disease type II (PKD2) mRNA, complete cds /cds=(66,2972) /gb=U50928 /gi=1373168 /ug=Hs.82001 /len=5057 | 0.117 | -0.342 | 1.243676769 | 38120_at |
| 33716_at | normal | 0.5104098 | Cluster Incl. N95443:zb81c12.s1 Homo sapiens cDNA, 3 end /clone=IMAGE-310006 /clone_end=3 /gb=N95443 /gi=1267753 /ug=Hs.19180 /len=611 | 0 | -0.083 | 1.008275126 | 33716_at |
| 40971_at | normal | 0.5085203 | Cluster Incl. D86982:Human mRNA for KIAA0229 gene, partial cds /cds=(0,3543) /gb=D86982 /gi=1504037 /ug=Hs.20060 /len=6335 | 0 | -0.127 | 0.982792326 | 40971_at |
| 34376_at | normal | 0.5077378 | Cluster Incl. AB019517:Homo sapiens PKIG mRNA for protein kinase inhibitor gamma, complete cds /cds=(4,234) /gb=AB019517 /gi=4760550 /ug=Hs.3407 /len=907 | -0.189 | -0.577 | 1.090185032 | 34376_at |
| 37599_at | normal | 0.5050271 | Cluster Incl. AF017060:untitled /cds=(298,4314) /gb=AF017060 /gi=2343154 /ug=Hs.81047 /len=5125 | 0 | -0.094 | 0.956519333 | 37599_at |
| 35146_at | normal | 0.5027407 | Cluster Incl. AB007836:Homo sapiens mRNA for Hic-5, partial cds /cds=(0,1383) /gb=AB007836 /gi=2865162 /ug=Hs.25511 /len=1770 | -0.206 | -0.453 | 0.996300995 | 35146_at |
| 41013_at | normal | 0.5023909 | Cluster Incl. AL080114:Homo sapiens mRNA; cDNA DKFZp586M2022 (from clone DKFZp586M2022) /cds=UNKNOWN /gb=AL080114 /gi=5262541 /ug=Hs.9208 /len=2572 | -0.583 | -0.253 | 1.04435939 | 41013_at |
| 33134_at | normal | 0.5010476 | Cluster Incl. AB011083:Homo sapiens mRNA for KIAA0511 protein, partial cds /cds=(0,2802) /gb=AB011083 /gi=3043545 /ug=Hs.8402 /len=3563 | -0.241 | -0.269 | 0.818321162 | 33134_at |

FIG. 2F

| Label | Distinction | Distance | Desc | pearson corr Tumor | pearson corr Normal | Mean TN Ratio | Accession |
|---|---|---|---|---|---|---|---|
| 31791_at | normal | 0.4999984 | Cluster Incl. Y16961:Homo sapiens mRNA for KET protein /cds=(27,2069) /gb=Y16961 /gi=3970716 /ug=Hs.137569 /len=4849 | -0.382 | 0.212 | 0.8848633141 | 31791_at |
| 34407_at | normal | 0.499588 | Cluster Incl. U77594:Human tazarotene-induced gene 2 (TIG2) mRNA, complete cds /cds=(96,587) /gb=U77594 /gi=1848263 /ug=Hs.37682 /len=708 | -0.401 | -0.323 | 1.24064117 | 34407_at |
| 40077_at | normal | 0.4979931 | Cluster Incl. Z11559:H.sapiens mRNA for iron regulatory factor /cds=(107,2776) /gb=Z11559 /gi=33962 /ug=Hs.154721 /len=3498 | 0.131 | -0.095 | 1.1237341011 | 40077_at |
| 36030_at | normal | 0.49495 | Cluster Incl. AL080214:Homo sapiens mRNA; cDNA DKFZp586I2223 (from clone DKFZp586I2223) /cds=(0,318) /gb=AL080214 /gi=5262704 /ug=Hs.46659 /len=1272 | -0.532 | -0.205 | 0.8272386665 | 36030_at |
| 32123_at | normal | 0.4942075 | Cluster Incl. L02870:Human alpha-1 type VII collagen (COL7A1) mRNA, complete cds /cds=(113,8947) /gb=L02870 /gi=987124 /ug=Hs.1640 /len=9287 | 0.117 | -0.079 | 1.0142669371 | 32123_at |
| 39673_i_at | normal | 0.4919724 | Cluster Incl. AB011792:Homo sapiens mRNA for extracellular matrix protein, complete cds /cds=(73,2172) /gb=AB011792 /gi=3786311 /ug=Hs.35094 /len=3171 | -0.001 | -0.335 | 1.0021181951 | 39673_i_at |
| 32554_s_at | normal | 0.491258 | Cluster Incl. Y12781:Homo sapiens mRNA for transducin (beta) like 1 protein /cds=(646,2379) /gb=Y12781 /gi=3021408 /ug=Hs.76536 /len=5875 | -0.073 | -0.468 | 1.0015818561 | 32554_s_at |
| 39243_s_at | normal | 0.488193 | Cluster Incl. U94319:Human autoantigen DFS70 mRNA, partial cds /cds=(0,1055) /gb=U94319 /gi=1945444 /ug=Hs.231884 /len=2507 | 0.024 | -0.119 | 1.1327781351 | 39243_s_at |
| 36569_at | normal | 0.4869782 | Cluster Incl. X64559:H.sapiens mRNA for tetranectin /cds=(93,701) /gb=X64559 /gi=37408 /ug=Hs.65424 /len=848 | 0.02 | -0.409 | 0.7708767611 | 36569_at |
| 863_g_at | normal | 0.4841968 | U04313 /FEATURE= /DEFINITION=HSU04313 Human maspin mRNA, complete cds | 0 | -0.191 | 0.8100314191 | 863_g_at |
| 37708_r_at | normal | 0.4821983 | Cluster Incl. M81118:Human alcohol dehydrogenase chi polypeptide (ADH5) gene /cds=(0,1124) /gb=M81118 /gi=178129 /ug=Hs.78989 /len=2334 | -0.165 | -0.086 | 1.2154635261 | 37708_r_at |

FIG. 2G

| Label | Distinction | Distance | Desc | pearson corr Tumor | pearson corr Normal | Mean TN Ratio | Accession |
|---|---|---|---|---|---|---|---|
| 33328_at | normal | 0.4816378 | Cluster Incl. W28612:49b3 Homo sapiens cDNA /gb=W28612 /gi=1308560 /ug=Hs.184724 /len=809 | -0.344 | -0.492 | 1.146081271 | 33328_at |
| 32780_at | normal | 0.4815746 | Cluster Incl. AB018271:Homo sapiens mRNA for KIAA0728 protein, partial cds /cds=(0,3197) /gb=AB018271 /gi=3882176 /ug=Hs.198689 /len=3964 | -0.417 | -0.258 | 1.059373721 | 32780_at |
| 38972_at | normal | 0.4792141 | Cluster Incl. AF052169:Homo sapiens clone 24775 mRNA sequence /cds=UNKNOWN /gb=AF052169 /gi=3360480 /ug=Hs.109438 /len=1385 | -0.267 | -0.475 | 1.156405165 | 38972_at |
| 37765_at | normal | 0.4774398 | Cluster Incl. X54162:Human mRNA for a 64 Kd autoantigen expressed in thyroid and extra-ocular muscle /cds=(212,1930) /gb=X54162 /gi=28968 /ug=Hs.79386 /len=3849 | -0.393 | -0.288 | 1.386937831 | 37765_at |
| 34853_at | normal | 0.4769865 | Cluster Incl. AB007865:Homo sapiens KIAA0405 mRNA, complete cds /cds=(1124,3106) /gb=AB007865 /gi=2662090 /ug=Hs.48998 /len=7527 | -0.358 | -0.178 | 0.854407582 | 34853_at |
| 39400_at | normal | 0.4760126 | Cluster Incl. AB028978:Homo sapiens mRNA for KIAA1055 protein, partial cds /cds=(0,2607) /gb=AB028978 /gi=5689446 /ug=Hs.126084 /len=5876 | -0.347 | -0.279 | 1.008370694 | 39400_at |
| 39634_at | normal | 0.4758675 | Cluster Incl. AB017168:Homo sapiens mRNA for Slit-2 protein, complete cds /cds=(204,4793) /gb=AB017168 /gi=4049586 /ug=Hs.29802 /len=4950 | 0.072 | -0.285 | 1.070284161 | 39634_at |
| 38057_at | normal | 0.4746458 | Cluster Incl. AL049798:Human DNA sequence from clone 797M17 on chromosome 1q22-24.3. Contains the DPT gene for Dermatopontin, ESTs, an STS and GSSs /cds=(9,614) /gb=AL049798 /gi=4995638 /ug=Hs.80552 /len=1705 | 0.024 | -0.052 | 0.726453651 | 38057_at |
| 35692_at | normal | 0.4728748 | Cluster Incl. AL080235:Homo sapiens mRNA; cDNA DKFZp586E1621 (from clone DKFZp586E1621) /cds=(0,452) /gb=AL080235 /gi=5262728 /ug=Hs.35861 /len=1111 | -0.432 | -0.405 | 0.933067285 | 35692_at |
| 40570_at | normal | 0.4687552 | Cluster Incl. AF032885:Homo sapiens forkhead protein (FKHR) mRNA, complete cds /cds=(385,2352) /gb=AF032885 /gi=2895491 /ug=Hs.170133 /len=5723 | -0.026 | -0.171 | 1.171886671 | 40570_at |

FIG. 2H

| Label | Distinction | Distance | Desc | pearson corr Tumor | pearson corr Normal | Mean TN Ratio | Accession |
|---|---|---|---|---|---|---|---|
| 36883_at | normal | 0.4685475 | Cluster Incl. X14640:Human mRNA for keratin 13 /cds=(42,1418) /gb=X14640 /gi=34032 /ug=Hs.74070 /len=1691 | -0.344 | -0.203 | 0.922439762 | 36883_at |
| 39750_at | normal | 0.4656649 | Cluster Incl. W61005:zd29a11.s1 Homo sapiens cDNA, 3 end /clone=IMAGE-342044 /clone_end=3 /gb=W61005 /gi=1367764 /ug=Hs.14896 /len=786 | -0.504 | -0.438 | 0.977588189 | 39750_at |
| 38730_at | normal | 0.4633874 | Cluster Incl. AB020671:Homo sapiens mRNA for KIAA0864 protein, partial cds /cds=(0,3656) /gb=AB020671 /gi=4240216 /ug=Hs.84883 /len=4319 | -0.067 | -0.13 | 1.145084285 | 38730_at |
| 38408_at | normal | 0.4625021 | Cluster Incl. L10373:Human (clone CCG-B7) mRNA sequence /cds=UNKNOWN /gb=L10373 /gi=307287 /ug=Hs.82749 /len=1792 | -0.332 | -0.232 | 0.806866038 | 38408_at |
| 1501_at | normal | 0.4622291 | X57025 /FEATURE=mRNA /DEFINITION=HSIGFACI Human IGF-I mRNA for insulin-like growth factor I | 0.109 | 0.077 | 1.143361908 | 1501_at |
| 38127_at | normal | 0.4602889 | Cluster Incl. Z48199:H.sapiens syndecan-1 gene (exons 2-5) /cds=(0,866) /gb=Z48199 /gi=666051 /ug=Hs.82109 /len=2802 | -0.242 | -0.181 | 0.939975803 | 38127_at |
| 41381_at | normal | 0.4588334 | Cluster Incl. AB002306:Human mRNA for KIAA0308 gene, partial cds /cds=(0,3895) /gb=AB002306 /gi=2224556 /ug=Hs.10351 /len=6452 | 0 | -0.214 | 1.266579255 | 41381_at |
| 39031_at | normal | 0.4567659 | Cluster Incl. AA152406:zo07f01.s1 Homo sapiens cDNA, 3 end /clone=IMAGE-567001 /clone_end=3 /gb=AA152406 /gi=1718616 /ug=Hs.114346 /len=400 | -0.174 | -0.337 | 1.274493058 | 39031_at |
| 32109_at | normal | 0.4561597 | Cluster Incl. AA524547:ng45h04.s1 Homo sapiens cDNA, 3 end /clone=IMAGE-937783 /clone_end=3 /gb=AA524547 /gi=2265475 /ug=Hs.160318 /len=626 | -0.203 | -0.297 | 0.795629701 | 32109_at |
| 32800_at | normal | 0.4530129 | Cluster Incl. U66306:Human retinoid X receptor alpha mRNA, 3 UTR, partial sequence /cds=UNKNOWN /gb=U66306 /gi=3411007 /ug=Hs.20084 /len=3772 | -0.325 | -0.03 | 1.126390293 | 32800_at |
| 39416_at | normal | 0.4516176 | Cluster Incl. U90913:Human clone 23665 mRNA sequence /cds=UNKNOWN /gb=U90913 /gi=1913893 /ug=Hs.12956 /len=1260 | -0.035 | -0.266 | 1.501378572 | 39416_at |

FIG. 2I

| Label | Distinction | Distance | Desc | pearson corr Tumor | pearson corr Normal | Mean TN Ratio | Accession |
|---|---|---|---|---|---|---|---|
| 33355_at | normal | 0.4515078 | Cluster Incl. AL049381:Homo sapiens mRNA; cDNA DKFZp586J2118 (from clone DKFZp586J2118) /cds=UNKNOWN /gb=AL049381 /gi=4500168 /ug=Hs.21851 /len=2261 | -0.423 | -0.137 | 1.14515886 | 33355_at |
| 36937_s_at | normal | 0.449224 | Cluster Incl. U90878:Homo sapiens carboxyl terminal LIM domain protein (CLIM1) mRNA, complete cds /cds=(142,1131) /gb=U90878 /gi=2957144 /ug=Hs.75807 /len=1480 | -0.015 | -0.229 | 1.072592511 | 36937_s_at |
| 34802_at | normal | 0.449053 | Cluster Incl. X15882:Human mRNA for collagen VI alpha-2 C-terminal globular domain /cds=(0,1289) /gb=X15882 /gi=30044 /ug=Hs.4217 /len=1585 | -0.212 | -0.251 | 1.053595579 | 34802_at |
| 1598_g_at | normal | 0.4480484 | L13720 /FEATURE= /DEFINITION=HUMGAS Homo sapiens growth-arrest-specific protein (gas) mRNA, complete cds | -0.279 | -0.366 | 0.8897921 | 1598_g_at |
| 31609_s_at | normal | 0.4478546 | Cluster Incl. L33799:Human procollagen C-proteinase enhancer protein (PCOLCE) mRNA, complete cds /cds=(60,1409) /gb=L33799 /gi=642907 /ug=Hs.202097 /len=1480 | -0.132 | -0.345 | 1.175487345 | 31609_s_at |
| 34735_at | normal | 0.4476179 | Cluster Incl. U43195:Human Rho-associated, coiled-coil containing protein kinase p160ROCK mRNA, complete cds /cds=(0,4064) /gb=U43195 /gi=1276900 /ug=Hs.239587 /len=4065 | 0.094 | -0.115 | 1.010775418 | 34735_at |
| 37408_at | normal | 0.4455124 | Cluster Incl. AB014609:Homo sapiens mRNA for KIAA0709 protein, complete cds /cds=(116,4555) /gb=AB014609 /gi=3327231 /ug=Hs.7835 /len=5641 | -0.1 | -0.195 | 1.042844429 | 37408_at |
| 37330_at | normal | 0.4454767 | Cluster Incl. U24266:Human pyrroline-5-carboxylate dehydrogenase (P5CDh) mRNA, long form, complete cds /cds=(30,1721) /gb=U24266 /gi=1353247 /ug=Hs.77448 /len=3134 | -0.072 | -0.092 | 0.771540279 | 37330_at |
| 37043_at | normal | 0.4446472 | Cluster Incl. AL021154:dJ150O5.2 (Inhibitor of DNA binding 3 (dominant negative helix-loop-helix protein, 1R21, HEIR-1)) /cds=(368,727) /gb=AL021154 /gi=3219576 /ug=Hs.76884 /len=1235 | -0.355 | -0.306 | 1.486268908 | 37043_at |

FIG. 2J

| Label | Distinction | Distance | Desc | pearson corr Tumor | pearson corr Normal | Mean TN Ratio | Accession |
|---|---|---|---|---|---|---|---|
| 33790_at | normal | 0.4435859 | Cluster Incl. AI720438:as81g04.x1 Homo sapiens cDNA, 3 end /clone=IMAGE-2335158 /clone_end=3 /gb=AI720438 /gi=5037694 /ug=Hs.20144 /len=550 | -0.204 | -0.434 | 0.9100439141 | 33790_at |
| 1541_f_at | normal | 0.4431409 | X02958 /FEATURE=cds /DEFINITION=HSIFNA6 Human interferon alpha gene IFN-alpha 6 | -0.329 | -0.238 | 0.8582296991 | 1541_f_at |
| 39082_at | normal | 0.4421718 | Cluster Incl. Y00097:Human mRNA for protein p68 /cds=(100,2121) /gb=Y00097 /gi=35217 /ug=Hs.118796 /len=2468 | -0.431 | -0.335 | 1.22375357 | 39082_at |
| 34678_at | normal | 0.4417292 | Cluster Incl. AL096713:Homo sapiens mRNA; cDNA DKFZp564E1616 (from clone DKFZp564E1616) /cds=UNKNOWN /gb=AL096713 /gi=5419845 /ug=Hs.234680 /len=4827 | 0.109 | -0.023 | 1.1661179721 | 34678_at |
| 39705_at | normal | 0.4416247 | Cluster Incl. AB014600:Homo sapiens mRNA for KIAA0700 protein, partial cds /cds=(0,3393) /gb=AB014600 /gi=3327213 /ug=Hs.13999 /len=5020 | -0.36 | -0.154 | 1.0838225941 | 39705_at |
| 38033_at | normal | 0.4407157 | Cluster Incl. AL049934:Homo sapiens mRNA; cDNA DKFZp564M1416 (from clone DKFZp564M1416) /cds=(0,546) /gb=AL049934 /gi=4884072 /ug=Hs.79844 /len=1869 | 0.117 | 0.04 | 1.36278072 | 38033_at |
| 37191_at | normal | 0.4406208 | Cluster Incl. D87463:Human mRNA for KIAA0273 gene, complete cds /cds=(403,1395) /gb=D87463 /gi=1665810 /ug=Hs.75899 /len=3040 | 0.068 | -0.464 | 0.7599039637 | 37191_at |
| 40767_at | normal | 0.4404459 | Cluster Incl. M59499:Human lipoprotein-associated coagulation inhibitor (LACI) gene /cds=(2,916) /gb=M59499 /gi=187205 /ug=Hs.170279 /len=3599 | -0.148 | -0.229 | 0.8848456921 | 40767_at |
| 32218_at | normal | 0.4396736 | Cluster Incl. AF034176:AF034176 Homo sapiens cDNA /clone=ntcon5-contig /gb=AF034176 /gi=2707738 /ug=Hs.188882 /len=7232 | -0.31 | -0.267 | 0.9559248211 | 32218_at |
| 41246_at | normal | 0.4364696 | Cluster Incl. AI743134:wg87f07.x1 Homo sapiens cDNA, 3 end /clone=IMAGE-2372101 /clone_end=3 /gb=AI743134 /gi=5111422 /ug=Hs.21858 /len=853 | -0.274 | -0.385 | 0.9056186541 | 41246_at |
| 37669_s_at | normal | 0.4361951 | Cluster Incl. U16799:Human Na,K-ATPase beta-1 subunit mRNA, complete cds /cds=(45,950) /gb=U16799 /gi=806753 /ug=Hs.78629 /len=1476 | -0.378 | -0.131 | 0.9657021971 | 37669_s_at |

FIG. 2K

| Label | Distinction | Distance | Desc | pearson corr Tumor | pearson corr Normal | Mean TN Ratio | Accession |
|---|---|---|---|---|---|---|---|
| 37853_at | normal | 0.4347634 | Cluster Incl. AI857458:wl57e02.x1 Homo sapiens cDNA, 3 end /clone=IMAGE-2429018 /clone_end=3 /gb=AI857458 /gi=5511074 /ug=Hs.134932 /len=540 | -0.083 | -0.096 | 0.686475542 | 37853_at |
| 39556_at | normal | 0.4346278 | Cluster Incl. M96803:Human general beta-spectrin (SPTBN1) mRNA, complete cds /cds=(310,7404) /gb=M96803 /gi=338442 /ug=Hs.107164 /len=7561 | 0.099 | -0.178 | 1.234605069 | 39556_at |
| 37630_at | normal | 0.43454 | Cluster Incl. AL049176:Human DNA sequence from clone 141H5 on chromosome Xq22.1-23. Contains parts of a novel Chordin LIKE protein with von Willebrand factor type C domains. Contains ESTs, STSs and GSSs /cds=(0,767) /gb=AL049176 /gi=4808226 /ug=Hs.82223 / | 0.024 | -0.068 | 0.932278886 | 37630_at |
| 1898_at | normal | 0.4327861 | L24203 /FEATURE= /DEFINITION=HUMDK Homo sapiens ataxia-telangiectasia group D-associated protein mRNA, complete cds | 0 | -0.104 | 1.087167291 | 1898_at |
| 829_s_at | normal | 0.4327326 | U21689 /FEATURE=cds /DEFINITION=HSU21689 Human glutathione S-transferase-P1c gene, complete cds | -0.285 | 0.01 | 0.93303168 | 829_s_at |
| 37326_at | normal | 0.4314067 | Cluster Incl. U93305:Homo sapiens A4 differentiation-dependent protein (A4), triple LIM domain protein (LMO6), and synaptophysin (SYP) genes, complete cds; and calcium channel alpha-1 subunit (CACNA1F) gene, partial cds /cds=(75,533) /gb=U93305 /gi=270759 | -0.203 | -0.088 | 1.261870935 | 37326_at |
| 32239_at | normal | 0.42833 | Cluster Incl. U69263:Human matrilin-2 precursor mRNA, partial cds /cds=(0,941) /gb=U69263 /gi=2072789 /ug=Hs.19368 /len=1033 | 0 | -0.189 | 1.064426985 | 32239_at |
| 36073_at | normal | 0.427804 | Cluster Incl. U35139:Human NECDIN related protein mRNA, complete cds /cds=(58,1023) /gb=U35139 /gi=1754970 /ug=Hs.50130 /len=1592 | 0.024 | -0.029 | 1.113966665 | 36073_at |
| 41404_at | normal | 0.4277829 | Cluster Incl. AJ010119:Homo sapiens mRNA for Ribosomal protein kinase B (RSK-B) /cds=(65,2383) /gb=AJ010119 /gi=3452408 /ug=Hs.105584 /len=3118 | 0 | -0.013 | 1.154877797 | 41404_at |
| 37658_at | normal | 0.4272229 | Cluster Incl. L13720:Homo sapiens growth-arrest-specific protein (gas) mRNA, complete cds /cds=(134,2170) /gb=L13720 /gi=401766 /ug=Hs.78501 /len=2461 | -0.372 | -0.241 | 1.022411047 | 37658_at |

FIG. 2L

| Label | Distinction | Distance | Desc | pearson corr Tumor | pearson corr Normal | Mean TN Ratio | Accession |
|---|---|---|---|---|---|---|---|
| 35354_at | normal | 0.4271821 | Cluster Incl. AL022326:dJ333H23.2.2 (Synaptogyrin 1A (SYNGR1A)) /cds=(43,744) /gb=AL022326 /gi=3550039 /ug=Hs.6139 /len=4406 | -0.534 | -0.088 | 0.914793807 | 35354_r_at |
| 32923_r_at | normal | 0.4269389 | Cluster Incl. M58378:Human synapsin I (SYN1) gene /cds=(0,2117) /gb=M58378 /gi=338648 /ug=Hs.225936 /len=2118 | 0.051 | -0.266 | 1.399794414 | 32923_r_at |
| 32747_at | normal | 0.4259642 | Cluster Incl. X05409:Human RNA for mitochondrial aldehyde dehydrogenase I ALDH I (EC 1.2.1.3) /cds=(36,1586) /gb=X05409 /gi=28605 /ug=Hs.195432 /len=1989 | -0.106 | -0.039 | 1.547370189 | 32747_at |
| 32035_at | normal | 0.4253557 | Cluster Incl. M16942:Human MHC class II HLA-DRw53-associated glycoprotein beta- chain mRNA, complete cds /cds=(28,828) /gb=M16942 /gi=188352 /ug=Hs.155122 /len=1141 | -0.073 | -0.195 | 1.149942774 | 32035_at |
| 39674_r_at | normal | 0.4242077 | Cluster Incl. AB011792:Homo sapiens mRNA for extracellular matrix protein, complete cds /cds=(73,2172) /gb=AB011792 /gi=3786311 /ug=Hs.35094 /len=3171 | -0.359 | -0.306 | 1.040980755 | 39674_r_at |
| 32629_f_at | normal | 0.4238503 | Cluster Incl. U90552:Human butyrophilin (BTF5) mRNA, complete cds /cds=(359,1900) /gb=U90552 /gi=2062705 /ug=Hs.167740 /len=3416 | -0.355 | -0.034 | 1.096669708 | 32629_f_at |
| 38761_s_at | normal | 0.4236463 | Cluster Incl. AA487755:ab13f01.r1 Homo sapiens cDNA, 5 end /clone=IMAGE-840697 /clone_end=5 /gb=AA487755 /gi=2215186 /ug=Hs.8762 /len=596 | -0.388 | -0.177 | 1.029545024 | 38761_s_at |
| 40098_at | normal | 0.4230661 | Cluster Incl. AF001434:Human Hpast (HPAST) mRNA, complete cds /cds=(255,1859) /gb=AF001434 /gi=2529706 /ug=Hs.155119 /len=3460 | -0.355 | -0.212 | 0.982709903 | 40098_at |
| 36037_g_at | normal | 0.4229615 | Cluster Incl. J05500:Human beta-spectrin (SPTB) mRNA, complete cds /cds=(95,6508) /gb=J05500 /gi=338439 /ug=Hs.47431 /len=6765 | 0.176 | -0.053 | 0.883179338 | 36037_g_at |
| 2041_i_at | normal | 0.4204168 | M14752 /FEATURE= /DEFINITION=HUMABLA Human c-abl gene, complete cds | 0 | -0.234 | 0.922697687 | 2041_i_at |
| 38424_at | normal | 0.4191129 | Cluster Incl. AB018290:Homo sapiens mRNA for KIAA0747 protein, partial cds /cds=(0,3219) /gb=AB018290 /gi=3882214 /ug=Hs.8309 /len=4026 | 0.009 | -0.257 | 1.123174605 | 38424_at |

FIG. 2M

| Label | Distinction | Distance | Desc | pearson corr Tumor | pearson corr Normal | Mean TN Ratio | Accession |
|---|---|---|---|---|---|---|---|
| 648_at | normal | 0.4180773 | L37112 /FEATURE=mRNA /DEFINITION=HUMVVR Homo sapiens vasopressin V3 receptor mRNA, complete cds | 0.147 | -0.152 | 0.9691277785 | 648_at |

FIG. 2N

| | | | Genes upregulated in Prostate tumors compared to Normal Prostate tissue | | | | |
|---|---|---|---|---|---|---|---|
| Label | Distinction | Distance | Desc | pearson corr Tumor | pearson corr Normal | Mean TN Ratio | Accession |
| 37639_at | tumor | 1.02803 | Cluster Incl. X07732:Human hepatoma mRNA for serine protease hepsin /cds=UNKNOWN /gb=X07732 /gi=32063 /ug=Hs.823 /len=2363 | 0.212 | -0.07 | 7.265066649 | 37639_at |
| 37720_at | tumor | 0.8952621 | Cluster Incl. M22382:Human mitochondrial matrix protein P1 (nuclear encoded) mRNA, complete cds /cds=(45,1766) /gb=M22382 /gi=190126 /ug=Hs.79037 /len=2227 | 0.365 | 0.181 | 3.578937122 | 37720_at |
| 41468_at | tumor | 0.879633 | Cluster Incl. M30894:Human T-cell receptor Ti rearranged gamma-chain mRNA V-J-C region, complete cds /cds=(140,1156) /gb=M30894 /gi=339406 /ug=Hs.112259 /len=1586 | 0.416 | 0.139 | 21.59227184 | 41468_at |
| 575_s_at | tumor | 0.8019986 | M93036 /FEATURE=mRNA /DEFINITION=HUMGA7A08 Human (clone 21726) carcinoma-associated antigen GA733-2 (GA733-2) mRNA, exon 9 and complete cds | 0.339 | 0.385 | 5.624420735 | 575_s_at |
| 33121_g_at | tumor | 0.7731754 | Cluster Incl. AF045229:Homo sapiens regulator of G protein signaling 10 mRNA, complete cds /cds=(132,635) /gb=AF045229 /gi=2906029 /ug=Hs.82280 /len=753 | 0.05 | 0.324 | 4.08091367 | 33121_g_at |
| 34840_at | tumor | 0.7680757 | Cluster Incl. AI700633:we38g03.x1 Homo sapiens cDNA, 3 end /clone=IMAGE-2343412 /clone_end=3 /gb=AI700633 /gi=4988533 /ug=Hs.4815 /len=565 | 0.197 | 0.514 | 3.822849421 | 34840_at |
| 39756_g_at | tumor | 0.7410893 | Cluster Incl. Z93930:Human DNA sequence from clone 292E10 on chromosome 22q11-12. Contains the XBP1 gene for X-box binding protein 1 (TREB5), ESTs, STSs, GSSs and a putative CpG island /cds=(30,815) /gb=Z93930 /gi=4775603 /ug=Hs.149923 /len=1802 | 0.183 | 0.399 | 7.703211629 | 39756_g_at |
| 40436_g_at | tumor | 0.7361572 | Cluster Incl. J03592:Human ADP/ATP translocase mRNA, 3 end, clone pHAT8 /cds=(0,788) /gb=J03592 /gi=339722 /ug=Hs.164280 /len=1116 | -0.062 | 0.099 | 6.814009007 | 40436_g_at |
| 914_g_at | tumor | 0.6866758 | M21535 /FEATURE= /DEFINITION=HUMERG11 Human erg protein (ets-related gene) mRNA, complete cds | -0.111 | 0 | 3.731285913 | 914_g_at |
| 36666_at | tumor | 0.6801084 | Cluster Incl. M22806:Human prolyl 4-hydroxylase beta-subunit and disulfide isomerase (P4HB) gene /cds=(66,1592) /gb=M22806 /gi=487831 /ug=Hs.75655 /len=2438 | 0.03 | 0.458 | 10.17667203 | 36666_at |

FIG. 3A

| Label | Distinction | Distance | Desc | pearson corr Tumor | pearson corr Normal | Mean TN Ratio | Accession |
|---|---|---|---|---|---|---|---|
| 1521_at | tumor | 0.6687818 | X17620 /FEATURE=mRNA /DEFINITION=HSNM23 Human mRNA for Nm23 protein, involved in developmental regulation (homolog. to Drosophila Awd protein) | 0.065 | 0.252 | 4.813779005 | 1521_at |
| 36495_at | tumor | 0.6597541 | Cluster Incl. U21931:Human fructose-1,6-biphosphatase (FBP1) gene /cds=(211,1227) /gb=U21931 /gi=1000077 /ug=Hs.574 /len=1476 | 0.354 | 0.125 | 4.320679169 | 36495_at |
| 31527_at | tumor | 0.6543049 | Cluster Incl. X17206:Human mRNA for LLRep3 /cds=(240,905) /gb=X17206 /gi=34391 /ug=Hs.182426 /len=934 | 0.21 | 0.19 | 10.43969779 | 31527_at |
| 37366_at | tumor | 0.6439773 | Cluster Incl. AL049969:Homo sapiens mRNA; cDNA DKFZp564A072 (from clone DKFZp564A072) /cds=UNKNOWN /gb=AL049969 /gi=4884218 /ug=Hs.7780 /len=2460 | 0.371 | -0.019 | 10.15824754 | 37366_at |
| 38814_at | tumor | 0.6374627 | Cluster Incl. AF038954:Homo sapiens vacuolar H(+)-ATPase subunit mRNA, complete cds /cds=(63,419) /gb=AF038954 /gi=3329377 /ug=Hs.90336 /len=1048 | 0.326 | 0.419 | 5.349300133 | 38814_at |
| 33904_at | tumor | 0.6302493 | Cluster Incl. AB000714:Homo sapiens hRVP1 mRNA for RVP1, complete cds /cds=(198,860) /gb=AB000714 /gi=2570128 /ug=Hs.25640 /len=1250 | 0.211 | 0.083 | 9.157059073 | 33904_at |
| 39755_at | tumor | 0.6152012 | Cluster Incl. Z93930:Human DNA sequence from clone 292E10 on chromosome 22q11-12. Contains the XBP1 gene for X-box binding protein 1 (TREB5), ESTs, STSs, GSSs and a putative CpG island /cds=(30,815) /gb=Z93930 /gi=4775603 /ug=Hs.149923 /len=1802 | 0.243 | 0.435 | 3.331069143 | 39755_at |
| 34775_at | tumor | 0.6134028 | Cluster Incl. AF065388:Homo sapiens tetraspan NET-1 mRNA, complete cds /cds=(121,846) /gb=AF065388 /gi=3152700 /ug=Hs.38972 /len=1278 | 0.296 | 0.577 | 15.99946769 | 34775_at |
| 1980_s_at | tumor | 0.6124387 | X58965 /FEATURE= /DEFINITION=HSNM23H2G H.sapiens RNA for nm23-H2 gene | 0.112 | -0.073 | 3.899965205 | 1980_s_at |
| 38429_at | tumor | 0.6082051 | Cluster Incl. U29344:Human breast carcinoma fatty acid synthase mRNA, complete cds /cds=(123,7652) /gb=U29344 /gi=915391 /ug=Hs.83190 /len=8460 | 0.093 | 0.41 | 7.764259505 | 38429_at |
| 40435_at | tumor | 0.6066332 | Cluster Incl. J03592:Human ADP/ATP translocase mRNA, 3 end, clone pHAT8 /cds=(0,788) /gb=J03592 /gi=339722 /ug=Hs.164280 /len=1116 | 0.236 | 0.186 | 6.968133119 | 40435_at |

FIG. 3B

| Label | Distinction | Distance | Desc | pearson corr Tumor | pearson corr Normal | Mean TN Ratio | Accession |
|---|---|---|---|---|---|---|---|
| 33614_at | tumor | 0.6058659 | Cluster Incl. X80822:H.sapiens mRNA for ORF /cds=(133,555) /gb=X80822 /gi=527577 /ug=Hs.163593 /len=657 | 0.216 | 0.157 | 6.200717326 | 33614_at |
| 31538_at | tumor | 0.6007735 | Cluster Incl. M17885:Human acidic ribosomal phosphoprotein P0 mRNA, complete cds /cds=(77,1030) /gb=M17885 /gi=190231 /ug=Hs.73742 /len=1097 | 0.247 | 0.264 | 21.40532513 | 31538_at |
| 36587_at | tumor | 0.5927849 | Cluster Incl. Z11692:H.sapiens mRNA for elongation factor 2 /cds=(0,2576) /gb=Z11692 /gi=31107 /ug=Hs.75309 /len=3080 | 0.225 | 0.07 | 5.931958891 | 36587_at |
| 34304_s_at | tumor | 0.5926514 | Cluster Incl. AL050290:Homo sapiens mRNA; cDNA DKFZp586G1923 (from clone DKFZp586G1923) /cds=(490,780) /gb=AL050290 /gi=4886512 /ug=Hs.28491 /len=1133 | 0.068 | 0.279 | 4.091941111 | 34304_s_at |
| 41755_at | tumor | 0.5876635 | Cluster Incl. AB023194:Homo sapiens mRNA for KIAA0977 protein, complete cds /cds=(216,3716) /gb=AB023194 /gi=4589597 /ug=Hs.182527 /len=4834 | -0.105 | 0.606 | 4.291548289 | 41755_at |
| 1715_at | tumor | 0.5806587 | U37518 /FEATURE= /DEFINITION=HSU37518 Human TNF-related apoptosis inducing ligand TRAIL mRNA, complete cds | 0.041 | 0.516 | 4.308381408 | 1715_at |
| 291_s_at | tumor | 0.5780528 | J04152 /FEATURE=mRNA /DEFINITION=HUMGA733A Human gastrointestinal tumor-associated antigen GA733-1 protein gene, complete cds, clone 05516 | 0.316 | 0.23 | 6.665470698 | 291_s_at |
| 37741_at | tumor | 0.5745491 | Cluster Incl. M77836:Human pyrroline 5-carboxylate reductase mRNA, complete cds /cds=(11,970) /gb=M77836 /gi=189497 /ug=Hs.79217 /len=1792 | 0.198 | 0.043 | 4.140536049 | 37741_at |
| 37730_at | tumor | 0.5593492 | Cluster Incl. U22055:Human 100 kDa coactivator mRNA, complete cds /cds=(267,2924) /gb=U22055 /gi=799176 /ug=Hs.79093 /len=3480 | 0.215 | 0.479 | 6.232930793 | 37730_at |
| 1676_s_at | tumor | 0.5561878 | M55409 /FEATURE= /DEFINITION=HUMPANCAN Homo sapiens pancreatic tumor-related protein mRNA, partial cds | 0.31 | 0.338 | 8.983150435 | 1676_s_at |
| 38642_at | tumor | 0.5542456 | Cluster Incl. Y10183:H.sapiens mRNA for MEMD protein /cds=(0,1748) /gb=Y10183 /gi=3183974 /ug=Hs.10247 /len=4193 | 0.096 | 0.215 | 3.415010384 | 38642_at |

FIG. 3C

| Label | Distinction | Distance | Desc | pearson corr Tumor | pearson corr Normal | Mean TN Ratio | Accession |
|---|---|---|---|---|---|---|---|
| 36491_at | tumor | 0.5482425 | Cluster Incl. D82345:Homo sapiens mRNA for NB thymosin beta, complete cds /cds=(97,234) /gb=D82345 /gi=1841339 /ug=Hs.56145 /len=639 | 0.053 | 0.492 | 8.707674891 | 36491_at |
| 33668_at | tumor | 0.5482019 | Cluster Incl. AF037643:Homo sapiens 60S ribosomal protein L12 (RPL12) pseudogene, partial sequence /cds=(85,474) /gb=AF037643 /gi=2746542 /ug=Hs.182979 /len=617 | 0.348 | 0.206 | 12.99908774 | 33668_at |
| 41485_at | tumor | 0.5474892 | Cluster Incl. X02152:Human mRNA for lactate dehydrogenase-A (LDH-A, EC 1.1.1.27) /cds=(97,1095) /gb=X02152 /gi=34312 /ug=Hs.2795 /len=1661 | 0.285 | -0.052 | 5.137440987 | 41485_at |
| 31568_at | tumor | 0.5424275 | Cluster Incl. U14972:Human ribosomal protein S10 mRNA, complete cds /cds=(16,513) /gb=U14972 /gi=550024 /ug=Hs.76230 /len=570 | 0.071 | 0.182 | 13.46711124 | 31568_at |
| 35119_at | tumor | 0.542408 | Cluster Incl. X56932:H.sapiens mRNA for 23 kD highly basic protein /cds=(17,628) /gb=X56932 /gi=23690 /ug=Hs.119122 /len=672 | 0.06 | 0.169 | 15.5691393 | 35119_at |
| 41732_at | tumor | 0.5418935 | Cluster Incl. AA310786:EST181572 Homo sapiens cDNA, 5 end /clone=ATCC-156790 /clone_end=5 /gb=AA310786 /gi=1963114 /ug=Hs.181634 /len=463 | -0.106 | -0.006 | 3.310246187 | 41732_at |
| 41106_at | tumor | 0.5399569 | Cluster Incl. AF022797:Homo sapiens intermediate conductance calcium-activated potassium channel (hKCa4) mRNA, complete cds /cds=(396,1679) /gb=AF022797 /gi=2674355 /ug=Hs.10082 /len=2238 | 0.121 | -0.04 | 2.723833049 | 41106_at |
| 33674_at | tumor | 0.5391359 | Cluster Incl. Z49148:H.sapiens mRNA for ribosomal protein L29 /cds=(29,508) /gb=Z49148 /gi=793842 /ug=Hs.183698 /len=630 | 0.289 | 0.308 | 12.58218259 | 33674_at |
| 36624_at | tumor | 0.5378093 | Cluster Incl. L33842:Homo sapiens (clone FFE-7) type II inosine monophosphate dehydrogenase (IMPDH2) gene, exons 1-13, complete cds /cds=(102,1646) /gb=L33842 /gi=602457 /ug=Hs.75432 /len=1688 | 0.178 | 0.168 | 3.834513722 | 36624_at |
| 256_s_at | tumor | 0.537187 | M14199 /FEATURE= /DEFINITION=HUMLAMR Human laminin receptor (2H5 epitope) mRNA, 5 end | 0.219 | 0.297 | 7.026035609 | 256_s_at |
| 36992_at | tumor | 0.5359647 | Cluster Incl. AI653621:tz21b11.x1 Homo sapiens cDNA, 3 end /clone=IMAGE-2289213 /clone_end=3 /gb=AI653621 /gi=4737600 /ug=Hs.76136 /len=598 | 0.212 | 0.274 | 5.331048467 | 36992_at |

FIG. 3D

| Label | Distinction | Distance | Desc | pearson corr Tumor | pearson corr Normal | Mean TN Ratio | Accession |
|---|---|---|---|---|---|---|---|
| 31509_at | tumor | 0.5352709 | Cluster Incl. X64707:H.sapiens BBC1 mRNA /cds=(51,686) /gb=X64707 /gi=29382 /ug=Hs.180842 /len=942 | -0.081 | 0.18 | 5.541504498 | 31509_at |
| 33415_at | tumor | 0.5352412 | Cluster Incl. X58965:H.sapiens RNA for nm23-H2 gene /cds=(72,530) /gb=X58965 /gi=35069 /ug=Hs.227823 /len=670 | 0.036 | -0.03 | 5.54903527 | 33415_at |
| 31907_at | tumor | 0.5346206 | Cluster Incl. D87735:Homo sapiens mRNA for ribosomal protein L14, complete cds /cds=(17,679) /gb=D87735 /gi=1620021 /ug=Hs.158675 /len=722 | 0.362 | 0.177 | 7.548531354 | 31907_at |
| 35814_at | tumor | 0.5341811 | Cluster Incl. AF064603:Homo sapiens GA17 protein mRNA, complete cds /cds=(51,1175) /gb=AF064603 /gi=3152659 /ug=Hs.69469 /len=1249 | 0.151 | 0.145 | 3.330711199 | 35814_at |
| 31545_at | tumor | 0.5314311 | Cluster Incl. AL031228:dJ1033B10.4 (40S ribosomal protein S18 (RPS18, KE-3)) /cds=(39,497) /gb=AL031228 /gi=3646023 /ug=Hs.75362 /len=541 | 0.248 | 0.357 | 26.59003924 | 31545_at |
| 38827_at | tumor | 0.5281344 | Cluster Incl. AF038451:Homo sapiens secreted cement gland protein XAG-2 homolog (hAG-2/R) mRNA, complete cds /cds=(58,585) /gb=AF038451 /gi=3779225 /ug=Hs.91011 /len=1059 | 0.234 | 0.089 | 8.280414736 | 38827_at |
| 41454_at | tumor | 0.5243815 | Cluster Incl. W27949.39h3 Homo sapiens cDNA /gb=W27949 /gi=1307897 /ug=Hs.111029 /len=735 | 0.13 | 0.519 | 4.663518186 | 41454_at |
| 40125_at | tumor | 0.5237051 | Cluster Incl. L10284:Homo sapiens integral membrane protein, calnexin, (IP90) mRNA, complete cds /cds=(89,1867) /gb=L10284 /gi=186522 /ug=Hs.155560 /len=4117 | 0.374 | 0.348 | 4.226066731 | 40125_at |
| 41214_at | tumor | 0.52333 | Cluster Incl. M58459:Human ribosomal protein (RPS4Y) isoform mRNA, complete cds /cds=(12,803) /gb=M58459 /gi=337511 /ug=Hs.180911 /len=860 | 0.03 | 0.188 | 6.238095674 | 41214_at |
| 34213_at | tumor | 0.521741 | Cluster Incl. AB020676:Homo sapiens mRNA for KIAA0869 protein, partial cds /cds=(0,2667) /gb=AB020676 /gi=4240226 /ug=Hs.21543 /len=3408 | 0.184 | 0.592 | 2.571297378 | 34213_at |
| 38604_at | tumor | 0.5163924 | Cluster Incl. AI198311:qi61f11.x1 Homo sapiens cDNA, 3 end /clone=IMAGE-1861005 /clone_end=3 /gb=AI198311 /gi=3750917 /ug=Hs.1832 /len=574 | 0.096 | 0.69 | 11.28532928 | 38604_at |

FIG. 3E

| Label | Distinction | Distance | Desc | pearson corr Tumor | pearson corr Normal | Mean TN Ratio | Accession |
|---|---|---|---|---|---|---|---|
| 31583_at | tumor | 0.5104084 | Cluster Incl. X67247:H.sapiens rpS8 gene for ribosomal protein S8 /cds=(23,649) /gb=X67247 /gi=36149 /ug=Hs.118690 /len=705 | 0.279 | 0.251 | 12.97671492 | 31583_at |
| 36203_at | tumor | 0.5102028 | Cluster Incl. X16277:Human gene for ornithine decarboxylase ODC (EC 4.1.1.17) /cds=(334,1719) /gb=X16277 /gi=35137 /ug=Hs.75212 /len=2062 | 0.203 | 0.123 | 8.310199172 | 36203_at |
| 39236_s_at | tumor | 0.5101478 | Cluster Incl. AL050372:Homo sapiens mRNA; cDNA DKFZp434A091 (from clone DKFZp434A091) /cds=UNKNOWN /gb=AL050372 /gi=4914608 /ug=Hs.227511 /len=1046 | 0.033 | 0.446 | 3.382060412 | 39236_s_at |
| 40093_at | tumor | 0.5088731 | Cluster Incl. X83425:H.sapiens LU gene for Lutheran blood group glycoprotein /cds=(22,1908) /gb=X83425 /gi=603559 /ug=Hs.155048 /len=2402 | -0.163 | 0.487 | 4.891447195 | 40093_at |
| 38684_at | tumor | 0.5041796 | Cluster Incl. AJ010953:Homo sapiens mRNA for putative Ca2+-transporting ATPase, partial /cds=(0,1491) /gb=AJ010953 /gi=3646133 /ug=Hs.106778 /len=2134 | 0.229 | 0.472 | 2.840698137 | 38684_at |
| 35766_at | tumor | 0.5035455 | Cluster Incl. M26326:Human keratin 18 mRNA, complete cds /cds=(51,1343) /gb=M26326 /gi=186690 /ug=Hs.65114 /len=1412 | 0.281 | 0.469 | 6.553892546 | 35766_at |
| 31952_at | tumor | 0.4968895 | Cluster Incl. X69391:H.sapiens mRNA for ribosomal protein L6 /cds=(26,892) /gb=X69391 /gi=36137 /ug=Hs.174131 /len=926 | -0.059 | 0.045 | 7.28839617 | 31952_at |
| 1513_at | tumor | 0.4966302 | Antigen, Prostate Specific, Alt. Splice Form 3 | 0.019 | 0.303 | 5.970261189 | 1513_at |
| 31505_at | tumor | 0.4958808 | Cluster Incl. Z28407:H.sapiens mRNA for ribosomal protein L8 /cds=(43,816) /gb=Z28407 /gi=433898 /ug=Hs.178551 /len=852 | 0.193 | 0.323 | 15.35999267 | 31505_at |
| 39798_at | tumor | 0.4940019 | Cluster Incl. R87876:yo45h01.r1 Homo sapiens cDNA, 5 end /clone=IMAGE-180913 /clone_end=5 /gb=R87876 /gi=946689 /ug=Hs.153177 /len=483 | -0.048 | 0.222 | 11.94128176 | 39798_at |
| 39740_g_at | tumor | 0.4934413 | Cluster Incl. AF054187:Homo sapiens alpha NAC mRNA, complete cds /cds=(309,956) /gb=AF054187 /gi=4092059 /ug=Hs.146763 /len=1059 | 0.293 | 0.299 | 7.865230431 | 39740_g_at |

FIG. 3F

| Label | Distinction | Distance | Desc | pearson corr Tumor | pearson corr Normal | Mean TN Ratio | Accession |
|---|---|---|---|---|---|---|---|
| 34646_at | tumor | 0.493342 | Cluster Incl. Z25749:H.sapiens gene for ribosomal protein S7 /cds=(81,665) /gb=Z25749 /gi=550116 /ug=Hs.75538 /len=687 | 0.225 | 0.172 | 6.485169626 | 34646_at |
| 39916_r_at | tumor | 0.4924037 | Cluster Incl. J02984:Human insulinoma rig-analog mRNA encoding DNA-binding protein, complete cds /cds=(29,466) /gb=J02984 /gi=184553 /ug=Hs.133230 /len=498 | 0.244 | 0.333 | 7.159387907 | 39916_r_at |
| 37141_at | tumor | 0.4922125 | Cluster Incl. U39840:Human hepatocyte nuclear factor-3 alpha (HNF-3 alpha) mRNA, complete cds /cds=(87,1508) /gb=U39840 /gi=1066121 /ug=Hs.105440 /len=2872 | 0.318 | 0.46 | 3.928787689 | 37141_at |
| 1173_g_at | tumor | 0.4916963 | Spermidine/Spermine N1-Acetyltransferase, Alt. Splice 2 | 0.196 | 0.35 | 7.164598172 | 1173_g_at |
| 33689_s_at | tumor | 0.4900845 | Cluster Incl. AF012434:untitled /cds=(38,394) /gb=AF012434 /gi=2352914 /ug=Hs.186570 /len=573 | 0.226 | 0.483 | 3.273345495 | 33689_s_at |
| 40910_at | tumor | 0.4892193 | Cluster Incl. U56637:Human capping protein alpha subunit isoform 1 mRNA, complete cds /cds=(0,860) /gb=U56637 /gi=1336098 /ug=Hs.184270 /len=2366 | 0.095 | 0.236 | 2.484094505 | 40910_at |
| 38435_at | tumor | 0.4867634 | Cluster Incl. U25182:Human antioxidant enzyme AOE37-2 mRNA, complete cds /cds=(43,858) /gb=U25182 /gi=799380 /ug=Hs.83383 /len=921 | 0.317 | 0.387 | 3.442959278 | 38435_at |
| 37955_at | tumor | 0.4866473 | Cluster Incl. AB015631:Homo sapiens mRNA for type II membrane protein, complete cds, clone-HP10390 /cds=(144,692) /gb=AB015631 /gi=4586839 /ug=Hs.8752 /len=814 | 0.148 | 0.387 | 4.026805772 | 37955_at |
| 39739_at | tumor | 0.4856721 | Cluster Incl. AF054187:Homo sapiens alpha NAC mRNA, complete cds /cds=(309,956) /gb=AF054187 /gi=4092059 /ug=Hs.146763 /len=1059 | 0.272 | 0.145 | 6.540731703 | 39739_at |
| 37017_at | tumor | 0.4856317 | Cluster Incl. M22430:Human RASF-A PLA2 mRNA, complete cds /cds=(135,569) /gb=M22430 /gi=190888 /ug=Hs.76422 /len=835 | 0.132 | 0.416 | 9.777195046 | 37017_at |
| 41868_at | tumor | 0.4853026 | Cluster Incl. J04131:Human gamma-glutamyl transpeptidase (GGT) protein mRNA, complete cds /cds=UNKNOWN /gb=J04131 /gi=183137 /ug=Hs.135 /len=2535 | 0.248 | 0.365 | 4.265692669 | 41868_at |

FIG. 3G

| Label | Distinction | Distance | Desc | pearson corr Tumor | pearson corr Normal | Mean TN Ratio | Accession |
|---|---|---|---|---|---|---|---|
| 37035_at | tumor | 0.4837498 | Cluster Incl. AI557272:PT2.1_15_G02.r Homo sapiens cDNA, 3 end /clone_end=3 /gb=AI557272 /gi=4489635 /ug=Hs.76698 /len=836 | 0.203 | 0.474 | 3.702973108 | 37035_at |
| 1740_g_at | tumor | 0.4829282 | M99487 /FEATURE= /DEFINITION=HUMPSM Human prostate-specific membrane antigen (PSM) mRNA, complete cds | 0.17 | 0.329 | 10.87695935 | 1740_g_at |
| 39056_at | tumor | 0.4792672 | Cluster Incl. X53793:H.sapiens ADE2H1 mRNA showing homologies to SAICAR synthetase and AIR carboxylase of the purine pathway (EC 6.3.2.6, EC 4.1.1.21) /cds=(24,1301) /gb=X53793 /gi=28383 /ug=Hs.117950 /len=1426 | 0.158 | -0.032 | 2.880260183 | 39056_at |
| 32432_f_at | tumor | 0.4790144 | Cluster Incl. L25899:Human ribosomal protein L10 mRNA, complete cds /cds=(16,633) /gb=L25899 /gi=414586 /ug=Hs.74267 /len=635 | 0.397 | 0.213 | 10.55187299 | 32432_f_at |
| 38780_at | tumor | 0.4784758 | Cluster Incl. J04794:Human aldehyde reductase mRNA, complete cds /cds=(60,1037) /gb=J04794 /gi=178480 /ug=Hs.89529 /len=1132 | 0.197 | 0.442 | 4.620953197 | 38780_at |
| 34608_at | tumor | 0.4775608 | Cluster Incl. M24194:Human MHC protein homologous to chicken B complex protein mRNA, complete cds /cds=UNKNOWN /gb=M24194 /gi=187701 /ug=Hs.5662 /len=1093 | 0.28 | 0.346 | 15.73966606 | 34608_at |
| 38456_s_at | tumor | 0.4758493 | Cluster Incl. AL049650:dJ734P14.2.2 (snRNP (small nuclear ribonucleoprotein particle) protein B) /cds=(129,851) /gb=AL049650 /gi=5123801 /ug=Hs.83753 /len=973 | -0.186 | 0.115 | 3.742950736 | 38456_s_at |
| 34316_at | tumor | 0.4753097 | Cluster Incl. W52024:zd13a03.s1 Homo sapiens cDNA, 3 end /clone=IMAGE-340492 /clone_end=3 /gb=W52024 /gi=1350030 /ug=Hs.2953 /len=531 | 0.163 | 0.143 | 3.053023569 | 34316_at |
| 40774_at | tumor | 0.4750823 | Cluster Incl. X74801:H.sapiens Cctg mRNA for chaperonin /cds=(0,1634) /gb=X74801 /gi=671526 /ug=Hs.1708 /len=1865 | 0.222 | 0.189 | 3.929530355 | 40774_at |
| 41163_at | tumor | 0.4741844 | Cluster Incl. AL109672:Homo sapiens mRNA full length insert cDNA clone EUROIMAGE 755868 /cds=(98,751) /gb=AL109672 /gi=5689836 /ug=Hs.179516 /len=1378 | 0.001 | 0.428 | 6.307686045 | 41163_at |

FIG. 3H

| Label | Distinction | Distance | Desc | pearson corr Tumor | pearson corr Normal | Mean TN Ratio | Accession |
|---|---|---|---|---|---|---|---|
| 38986_at | tumor | 0.4730182 | Cluster Incl. Z49835:H.sapiens mRNA for protein disulfide isomerase /cds=(106,1623) /gb=Z49835 /gi=860985 /ug=Hs.110029 /len=1954 | 0.389 | 0.395 | 4.583334647 | 38986_at |
| 1009_at | tumor | 0.4726387 | U51004 /FEATURE= /DEFINITION=HSU51004 Homo sapiens protein kinase C inhibitor (PKCI-1) mRNA, complete cds | 0.271 | 0.416 | 7.299521593 | 1009_at |
| 37000_at | tumor | 0.4708546 | Cluster Incl. AL035304:H.sapiens gene from PAC 295C6, similar to rat PO44 /cds=(159,542) /gb=AL035304 /gi=4200231 /ug=Hs.76285 /len=798 | 0.092 | 0.225 | 4.946918131 | 37000_at |
| 34791_at | tumor | 0.470392 | Cluster Incl. X52882:Human t-complex polypeptide 1 gene /cds=(21,1691) /gb=X52882 /gi=311380 /ug=Hs.4112 /len=2019 | 0.264 | 0.04 | 3.12172442 | 34791_at |
| 32412_at | tumor | 0.4703841 | Cluster Incl. M13934:Human ribosomal protein S14 gene, complete cds /cds=(2,457) /gb=M13934 /gi=337498 /ug=Hs.3491 /len=503 | 0.261 | 0.18 | 16.84175159 | 32412_at |
| 35307_at | tumor | 0.4695534 | Cluster Incl. Y13286:Homo sapiens mRNA for GDP dissociation inhibitor beta /cds=(152,1489) /gb=Y13286 /gi=2853173 /ug=Hs.56845 /len=2274 | 0.238 | 0.297 | 3.879058571 | 35307_at |
| 34592_at | tumor | 0.4674897 | Cluster Incl. M13932:Human ribosomal protein S17 mRNA, complete cds /cds=(25,432) /gb=M13932 /gi=337500 /ug=Hs.5174 /len=477 | 0.255 | 0.313 | 19.28560666 | 34592_at |
| 39353_at | tumor | 0.4672166 | Cluster Incl. AI912041:wd84b06.x1 Homo sapiens cDNA, 3 end /clone=IMAGE-2338259 /clone_end=3 /gb=AI912041 /gi=5631896 /ug=Hs.1197 /len=570 | 0.336 | 0.196 | 3.629899816 | 39353_at |
| 35793_at | tumor | 0.466097 | Cluster Incl. AB014560:Homo sapiens mRNA for KIAA0660 protein, complete cds /cds=(120,1568) /gb=AB014560 /gi=3327133 /ug=Hs.6727 /len=4210 | 0.232 | 0.368 | 3.332871921 | 35793_at |
| 32543_at | tumor | 0.4641014 | Cluster Incl. M84739:Human autoantigen calreticulin mRNA, complete cds /cds=(108,1361) /gb=M84739 /gi=179881 /ug=Hs.75525 /len=1937 | 0.126 | 0.184 | 5.216354605 | 32543_at |
| 32112_s_at | tumor | 0.4632421 | Cluster Incl. AI800499:tc11f11.x1 Homo sapiens cDNA, 3 end /clone=IMAGE-2063565 /clone_end=3 /gb=AI800499 /gi=5365971 /ug=Hs.161002 /len=403 | -0.088 | 0.701 | 3.895938165 | 32112_s_at |

FIG. 31

| Label | Distinction | Distance | Desc | pearson corr Tumor | pearson corr Normal | Mean TN Ratio | Accession |
|---|---|---|---|---|---|---|---|
| 36928_at | tumor | 0.4625941 | Cluster Incl. X70394:H.sapiens OZF mRNA /cds=(856,1734) /gb=X70394 /gi=468707 /ug=Hs.75471 /len=3186 | -0.486 | 0.079 | 2.669992625 | 36928_at |
| 33386_at | tumor | 0.4623681 | Cluster Incl. Z97630:Human DNA sequence from clone 466N1 on chromosome 22q12-13 Contains H1F0(H1 histone family, member 0) gene, 2-amino-3-ketobutyrate-CoA ligase(nuclear gene encoding mitochondrial protein), GALR3 (galanin receptor) gene, ESTs, GSSs an | 0.212 | 0.619 | 2.521543766 | 33386_at |
| 38679_g_at | tumor | 0.4622386 | Cluster Incl. AA733050:zg79b05.s1 Homo sapiens cDNA, 3 end /clone=399537 /clone_end=3 /gb=AA733050 /gi=2754409 /ug=Hs.1066 /len=706 | 0.033 | 0.16 | 3.988938094 | 38679_g_at |
| 36193_at | tumor | 0.4621878 | Cluster Incl. U52522:Human arfaptin 2, putative target protein of ADP-ribosylation factor, mRNA, complete cds /cds=(67,1092) /gb=U52522 /gi=1279762 /ug=Hs.75139 /len=1654 | 0.158 | 0.376 | 3.929796576 | 36193_at |
| 691_g_at | tumor | 0.4617025 | J02783 /FEATURE=mRNA /DEFINITION=HUMTHBP Human thyroid hormone binding protein (p55) mRNA, complete cds | 0.308 | 0.373 | 10.66765036 | 691_g_at |
| 32435_at | tumor | 0.461506 | Cluster Incl. X63527:H.sapiens mRNA for ribosomal protein L19 /cds=(28,618) /gb=X63527 /gi=36127 /ug=Hs.75879 /len=698 | 0.296 | 0.271 | 15.44216686 | 32435_at |
| 32437_at | tumor | 0.4595675 | Cluster Incl. U14970:Human ribosomal protein S5 mRNA, complete cds /cds=(37,651) /gb=U14970 /gi=550020 /ug=Hs.76194 /len=705 | 0.297 | 0.336 | 15.55948061 | 32437_at |
| 32315_at | tumor | 0.4560916 | Cluster Incl. M31520:Human ribosomal protein S24 mRNA /cds=(142,543) /gb=M31520 /gi=337504 /ug=Hs.180450 /len=620 | -0.057 | 0.166 | 9.902677982 | 32315_at |
| 36201_at | tumor | 0.4552856 | Cluster Incl. D13315:Human mRNA for lactoyl glutathione lyase /cds=(87,641) /gb=D13315 /gi=219663 /ug=Hs.75207 /len=1993 | 0.207 | 0.224 | 7.66691948 | 36201_at |
| 1470_at | tumor | 0.4552478 | U21090 /FEATURE= /DEFINITION=HSU21090 Human DNA polymerase delta small subunit mRNA, complete cds | 0.138 | 0.171 | 2.984455685 | 1470_at |
| 36529_at | tumor | 0.4549247 | Cluster Incl. AI885381:wi93b01.x1 Homo sapiens cDNA, 3 end /clone=IMAGE-2432425 /clone_end=3 /gb=AI885381 /gi=5590545 /ug=Hs.61273 /len=668 | -0.193 | 0.166 | 2.43729433 | 36529_at |

FIG. 3J

| Label | Distinction | Distance | Desc | pearson corr Tumor | pearson corr Normal | Mean TN Ratio | Accession |
|---|---|---|---|---|---|---|---|
| 34893_at | tumor | 0.4544144 | Cluster Incl. AI557064:PT2.1_13_A12.r Homo sapiens cDNA, 3 end /clone_end=3 /gb=AI557064 /gi=4489427 /ug=Hs.51299 /len=876 | 0.095 | 0.435 | 4.547293958 | 34893_at |
| 254_at | tumor | 0.4533134 | M11353 /FEATURE= /DEFINITION=HUMHISH3C Human H3.3 histone class C mRNA, complete cds | 0.172 | 0.218 | 5.65070281 | 254_at |
| 39830_at | tumor | 0.451657 | Cluster Incl. AA044823:zk72a10.s1 Homo sapiens cDNA, 3 end /clone=IMAGE-488346 /clone_end=3 /gb=AA044823 /gi=1523026 /ug=Hs.111611 /len=649 | 0.264 | 0.104 | 9.84444291 | 39830_at |
| 33820_g_at | tumor | 0.4509665 | Cluster Incl. X13794:H.sapiens lactate dehydrogenase B gene exon 1 and 2 (EC 1.1.1.27) (and joined CDS) /cds=(84,1088) /gb=X13794 /gi=34314 /ug=Hs.234489 /len=1272 | 0.287 | 0.039 | 5.233175186 | 33820_g_at |
| 35759_at | tumor | 0.4506224 | Cluster Incl. AF026166:Homo sapiens chaperonin-containing TCP-1 beta subunit homolog mRNA, complete cds /cds=(57,1664) /gb=AF026166 /gi=4090928 /ug=Hs.6456 /len=1925 | 0.271 | 0.192 | 3.920372562 | 35759_at |
| 41152_f_at | tumor | 0.4487239 | Cluster Incl. T89651:yd99a05.s1 Homo sapiens cDNA, 3 end /clone=IMAGE-116336 /clone_end=3 /gb=T89651 /gi=718164 /ug=Hs.178391 /len=559 | 0.054 | 0.061 | 7.402274709 | 41152_f_at |
| 40437_at | tumor | 0.4469954 | Cluster Incl. AL049944:Homo sapiens mRNA; cDNA DKFZp564G2022 (from clone DKFZp564G2022) /cds=(0,399) /gb=AL049944 /gi=4884189 /ug=Hs.16492 /len=1557 | 0.158 | 0.441 | 4.537534233 | 40437_at |
| 31546_at | tumor | 0.4469244 | Cluster Incl. L11566:Homo sapiens ribosomal protein L18 (RPL18) mRNA, complete cds /cds=(15,581) /gb=L11566 /gi=337492 /ug=Hs.75458 /len=630 | 0.282 | 0.32 | 10.43375658 | 31546_at |
| 34645_at | tumor | 0.4463106 | Cluster Incl. X55715:Human Hums3 mRNA for 40S ribosomal protein s3 /cds=(22,753) /gb=X55715 /gi=32531 /ug=Hs.75459 /len=833 | 0.27 | 0.291 | 18.98160745 | 34645_at |
| 32440_at | tumor | 0.444325 | Cluster Incl. X53777:Human L23 mRNA for putative ribosomal protein /cds=(138,692) /gb=X53777 /gi=34198 /ug=Hs.82202 /len=724 | 0.262 | 0.232 | 9.330535694 | 32440_at |
| 33912_at | tumor | 0.4424512 | Cluster Incl. Y13834:Homo sapiens mRNA for farnesylated-proteins converting enzyme 1 /cds=(33,1460) /gb=Y13834 /gi=5327058 /ug=Hs.25846 /len=2966 | 0.253 | 0.279 | 2.850042302 | 33912_at |

FIG. 3K

| Label | Distinction | Distance | Desc | pearson corr Tumor | pearson corr Normal | Mean TN Ratio | Accession |
|---|---|---|---|---|---|---|---|
| 35829_at | tumor | 0.4421895 | Cluster Incl. AL080181:Homo sapiens mRNA; cDNA DKFZp434O111 (from clone DKFZp434O111) /cds=UNKNOWN /gb=AL080181 /gi=5262657 /ug=Hs.70337 /len=1383 | 0.142 | -0.018 | 2.624863296 | 35829_at |
| 33660_at | tumor | 0.4420913 | Cluster Incl. U14966:Human ribosomal protein L5 mRNA, complete cds /cds=(30,923) /gb=U14966 /gi=550012 /ug=Hs.180946 /len=987 | 0.186 | 0.19 | 8.562331011 | 33660_at |
| 32786_at | tumor | 0.4415175 | Cluster Incl. X51345:Human jun-B mRNA for JUN-B protein /cds=(253,1296) /gb=X51345 /gi=34014 /ug=Hs.198951 /len=1797 | -0.039 | -0.348 | 5.69177785 | 32786_at |
| 36171_at | tumor | 0.4413365 | Cluster Incl. AI521453:tb60h07.x1 Homo sapiens cDNA, 3 end /clone=IMAGE-2122717 /clone_end=3 /gb=AI521453 /gi=4435588 /ug=Hs.74861 /len=622 | 0.01 | 0.191 | 3.272074425 | 36171_at |
| 33656_at | tumor | 0.4405951 | Cluster Incl. D23661:Human mRNA for ribosomal protein L37, complete cds /cds=(28,321) /gb=D23661 /gi=432361 /ug=Hs.179779 /len=369 | 0.246 | 0.127 | 6.514918091 | 33656_at |
| 34800_at | tumor | 0.4402603 | Cluster Incl. AL039458:DKFZp434N0910_s1 Homo sapiens cDNA, 3 end /clone=DKFZp434N0910 /clone_end=3 /gb=AL039458 /gi=5408506 /ug=Hs.4193 /len=849 | 0.37 | 0.546 | 4.156866191 | 34800_at |
| 32341_f_at | tumor | 0.4390408 | Cluster Incl. U37230:Human ribosomal protein L23a mRNA, complete cds /cds=(23,493) /gb=U37230 /gi=1574941 /ug=Hs.184776 /len=548 | 0.309 | 0.24 | 11.34738125 | 32341_f_at |
| 31906_at | tumor | 0.437977 | Cluster Incl. AF068754:Homo sapiens heat shock factor binding protein 1 HSBP1 mRNA, complete cds /cds=(54,284) /gb=AF068754 /gi=3283408 /ug=Hs.158675 /len=534 | -0.204 | 0.221 | 4.132456553 | 31906_at |
| 40881_at | tumor | 0.4379091 | Cluster Incl. X64330:H.sapiens mRNA for ATP-citrate lyase /cds=(84,3401) /gb=X64330 /gi=28934 /ug=Hs.174140 /len=4297 | 0.214 | 0.516 | 3.932361044 | 40881_at |
| 40297_at | tumor | 0.4371608 | Cluster Incl. AC005053:Homo sapiens BAC clone RG041D11 from 7q21 /cds=(0,1121) /gb=AC005053 /gi=3924666 /ug=Hs.61635 /len=1122 | 0.239 | 0.522 | 4.927111301 | 40297_at |
| 614_at | tumor | 0.4371447 | M22430 /FEATURE= /DEFINITION=HUMRASFAB Human RASF-A PLA2 mRNA, complete cds | 0.137 | 0.283 | 12.58700911 | 614_at |

FIG. 3L

| Label | Distinction | Distance | Desc | pearson corr Tumor | pearson corr Normal | Mean TN Ratio | Accession |
|---|---|---|---|---|---|---|---|
| 31330_at | tumor | 0.4367431 | Cluster Incl. M81757:H.sapiens S19 ribosomal protein mRNA, complete cds /cds=(22,459) /gb=M81757 /gi=337732 /ug=Hs.126701 /len=497 | 0.255 | 0.28 | 12.34998475 | 31330_at |
| 36933_at | tumor | 0.4358277 | Cluster Incl. D87953:Human mRNA for RTP, complete cds /cds=(122,1306) /gb=D87953 /gi=1596166 /ug=Hs.75789 /len=3014 | 0.134 | 0.58 | 3.781971464 | 36933_at |
| 38729_at | tumor | 0.4348072 | Cluster Incl. M88279:Human immunophilin (FKBP52) mRNA, complete cds /cds=(99,1478) /gb=M88279 /gi=186389 /ug=Hs.848 /len=2156 | 0.236 | 0.341 | 3.875727897 | 38729_at |
| 35810_at | tumor | 0.434638 | Cluster Incl. AI525393:PT1.1_07_A11.r Homo sapiens cDNA, 5 end /clone_end=5 /gb=AI525393 /gi=4439528 /ug=Hs.6895 /len=811 | 0.256 | 0.159 | 2.842711222 | 35810_at |
| 38754_at | tumor | 0.4345397 | Cluster Incl. AI557295:PT2.1_16_D02.r Homo sapiens cDNA, 3 end /clone_end=3 /gb=AI557295 /gi=4489658 /ug=Hs.8603 /len=847 | 0.153 | 0.29 | 5.676608654 | 38754_at |
| 895_at | tumor | 0.4343157 | L19686 /FEATURE=mRNA /DEFINITION=HUMMIF Homo sapiens macrophage migration inhibitory factor (MIF) gene, complete cds | 0.195 | 0.247 | 6.243400144 | 895_at |
| 35326_at | tumor | 0.4340225 | Cluster Incl. AF004876:Homo sapiens 54TMp (54tm) mRNA, complete cds /cds=(115,996) /gb=AF004876 /gi=4101573 /ug=Hs.5809 /len=1053 | 0.116 | 0.163 | 2.466963494 | 35326_at |
| 40766_at | tumor | 0.4334103 | Cluster Incl. U24578:Human RP1 and complement C4B precursor (C4B) genes, partial cds /cds=(111,5210) /gb=U24578 /gi=1125049 /ug=Hs.170250 /len=5352 | -0.228 | -0.077 | 7.294319847 | 40766_at |
| 1798_at | tumor | 0.4330649 | U41060 /FEATURE= /DEFINITION=HSU41060 Human breast cancer, estrogen regulated LIV-1 protein (LIV-1) mRNA, partial cds | 0.078 | 0.647 | 5.732825893 | 1798_at |
| 2016_s_at | tumor | 0.4322862 | M64241 /FEATURE=/DEFINITION=HUMQM Human Wilms tumor-related protein (QM) mRNA, complete cds | 0.303 | 0.253 | 15.4237431 | 2016_s_at |
| 35628_at | tumor | 0.4316858 | Cluster Incl. AF023676:Homo sapiens lamin B receptor homolog TM7SF2 (TM7SF2) mRNA, complete cds /cds=(254,2023) /gb=AF023676 /gi=3211721 /ug=Hs.31130 /len=2084 | 0.105 | 0.412 | 5.686636582 | 35628_at |

FIG. 3M

| Label | Distinction | Distance | Desc | pearson corr Tumor | pearson corr Normal | Mean TN Ratio | Accession |
|---|---|---|---|---|---|---|---|
| 40803_at | tumor | 0.4303264 | Cluster Incl. AL050161:Homo sapiens mRNA; cDNA DKFZp586B0222 (from clone DKFZp586B0222) /cds=UNKNOWN /gb=AL050161 /gi=4884375 /ug=Hs.172089 /len=1573 | 0.059 | 0.2 | 2.676642185 | 40803_at |
| 33485_at | tumor | 0.4302381 | Cluster Incl. D23660:Human mRNA for ribosomal protein, complete cds /cds=(56,1339) /gb=D23660 /gi=432358 /ug=Hs.286 /len=1418 | 0.178 | 0.231 | 8.051223892 | 33485_at |
| 35823_at | tumor | 0.4301667 | Cluster Incl. M63573:Human secreted cyclophilin-like protein (SCYLP) mRNA, complete cds /cds=(21,671) /gb=M63573 /gi=337998 /ug=Hs.699 /len=893 | 0.082 | 0.266 | 8.785332494 | 35823_at |
| 41178_at | tumor | 0.4297155 | Cluster Incl. X79234:H.sapiens mRNA for ribosomal protein L11 /cds=(0,536) /gb=X79234 /gi=495125 /ug=Hs.179943 /len=591 | 0.268 | 0.234 | 14.5479072 | 41178_at |
| 33619_at | tumor | 0.4291499 | Cluster Incl. L01124:Human ribosomal protein S13 (RPS13) mRNA, complete cds /cds=(32,487) /gb=L01124 /gi=307390 /ug=Hs.165590 /len=530 | 0.309 | 0.138 | 7.235591659 | 33619_at |
| 36677_at | tumor | 0.4289148 | Cluster Incl. X70476:H.sapiens subunit of coatomer complex /cds=(68,2788) /gb=X70476 /gi=298096 /ug=Hs.75724 /len=3067 | 0.134 | 0.499 | 3.487330345 | 36677_at |
| 40637_at | tumor | 0.4258878 | Cluster Incl. Y00371:Human hsc70 gene for 71 kd heat shock cognate protein /cds=(83,2023) /gb=Y00371 /gi=32466 /ug=Hs.180414 /len=2024 | 0.351 | 0.212 | 4.819007605 | 40637_at |
| 409_at | tumor | 0.4253834 | X56468 /FEATURE=mRNA /DEFINITION=HS1433 Human mRNA for 14.3.3 protein, a protein kinase regulator | 0.301 | 0.294 | 3.743015051 | 409_at |
| 35710_s_at | tumor | 0.4253767 | Cluster Incl. U95006:Human D9 splice variant A mRNA, complete cds /cds=(3,194) /gb=U95006 /gi=2071992 /ug=Hs.37616 /len=697 | 0.075 | 0.486 | 3.377507231 | 35710_s_at |
| 36686_at | tumor | 0.4232364 | Cluster Incl. U07919:Human aldehyde dehydrogenase 6 mRNA, complete cds /cds=(52,1590) /gb=U07919 /gi=995897 /ug=Hs.75746 /len=3442 | 0.263 | -0.016 | 4.157430602 | 36686_at |
| 36658_at | tumor | 0.4226676 | Cluster Incl. D13643:Human mRNA for KIAA0018 gene, complete cds /cds=(38,1210) /gb=D13643 /gi=285996 /ug=Hs.75616 /len=4186 | 0.293 | 0.293 | 6.632539212 | 36658_at |

FIG. 3N

| Label | Distinction | Distance | Desc | pearson corr Tumor | pearson corr Normal | Mean TN Ratio | Accession |
|---|---|---|---|---|---|---|---|
| 32394_s_at | tumor | 0.4224276 | Cluster Incl. X55954:Human mRNA for HL23 ribosomal protein homologue /cds=(12,434) /gb=X55954 /gi=34193 /ug=Hs.234518 /len=479 | 0.264 | 0.3 | 8.192700057 | 32394_s_at |
| 38061_at | tumor | 0.4221511 | Cluster Incl. AI541256:pec1.2-3.F11.r Homo sapiens cDNA, 5 end /clone_end=5 /gb=AI541256 /gi=4458629 /ug=Hs.80617 /len=717 | 0.229 | 0.247 | 18.7099029 | 38061_at |
| 31902_at | tumor | 0.4201596 | Cluster Incl. AF093774:Homo sapiens type 2 iodothyronine deiodinase mRNA, complete cds and 3UTR /cds=(134,976) /gb=AF093774 /gi=4009516 /ug=Hs.154424 /len=6161 | -0.17 | -0.232 | 2.371604345 | 31902_at |
| 1179_at | tumor | 0.4191549 | Heat Shock Protein, 70 Kda | 0.343 | 0.2 | 5.664271282 | 1179_at |
| 41765_at | tumor | 0.4191184 | Cluster Incl. AI541285:pec1.2-4.D10.r Homo sapiens cDNA, 5 end /clone_end=5 /gb=AI541285 /gi=4458658 /ug=Hs.182825 /len=617 | 0.166 | 0.215 | 6.580338458 | 41765_at |
| 33677_at | tumor | 0.4183493 | Cluster Incl. M94314:Homo sapiens ribosomal protein L30 mRNA, complete cds /cds=(39,512) /gb=M94314 /gi=292436 /ug=Hs.184582 /len=556 | 0.207 | 0.089 | 10.6518226 | 33677_at |
| 41721_at | tumor | 0.4177343 | Cluster Incl. AA658877:nt84c12.s1 Homo sapiens cDNA /clone=IMAGE-1205206 /gb=AA658877 /gi=2595031 /ug=Hs.181350 /len=897 | 0.254 | 0.707 | 19.34935917 | 41721_at |
| 1356_at | tumor | 0.41723 | U18321 /FEATURE= /DEFINITION=HSU18321 Human ionizing radiation resistance conferring protein mRNA, complete cds | 0.093 | -0.028 | 2.852479188 | 1356_at |
| 36786_at | tumor | 0.4169288 | Cluster Incl. AL022721:dJ109F14.2 (60S Ribosomal Protein RPL10A) /cds=(15,668) /gb=AL022721 /gi=3367610 /ug=Hs.76067 /len=703 | 0.294 | 0.284 | 10.91751082 | 36786_at |
| 41867_at | tumor | 0.4167136 | Cluster Incl. AF055009:Homo sapiens clone 24747 mRNA sequence /cds=UNKNOWN /gb=AF055009 /gi=3005731 /ug=Hs.13456 /len=1800 | 0.239 | 0.143 | 5.385812991 | 41867_at |
| 263_g_at | tumor | 0.4164362 | M21154 /FEATURE=mRNA /DEFINITION=HUMAMD Human S-adenosylmethionine decarboxylase mRNA, complete cds | 0.281 | 0.263 | 5.343027613 | 263_g_at |
| 36847_r_at | tumor | 0.4155153 | Cluster Incl. AA121509:zk88c10.s1 Homo sapiens cDNA, 3 end /clone=IMAGE-489906 /clone_end=3 /gb=AA121509 /gi=1679123 /ug=Hs.70830 /len=593 | -0.144 | 0.253 | 2.60269437 | 36847_r_at |

FIG. 30

| Label | Distinction | Distance | Desc | pearson corr Tumor | pearson corr Normal | Mean TN Ratio | Accession |
|---|---|---|---|---|---|---|---|
| 32051_at | tumor | 0.4147166 | Cluster Incl. AJ224875:Homo sapiens mRNA for putative glucosyltransferase, partial cds /cds=(0,1599) /gb=AJ224875 /gi=2996577 /ug=Hs.155356 /len=1622 | -0.396 | 0.566 | 2.40661278 | 32051_at |
| 1312_at | tumor | 0.4146724 | D38047 /FEATURE= /DEFINITION=HUMPSP31 Human mRNA for 26S proteasome subunit p31, complete cds | 0.319 | 0.334 | 4.16178386 | 1312_at |
| 40546_s_at | tumor | 0.4146132 | Cluster Incl. AF047185:Homo sapiens NADH-ubiquinone oxidoreductase subunit CI-B8 mRNA, complete cds /cds=(56,355) /gb=AF047185 /gi=2909861 /ug=Hs.163867 /len=575 | 0.002 | 0.35 | 3.144189455 | 40546_s_at |
| 39876_at | tumor | 0.4133416 | Cluster Incl. AL035252:Human DNA sequence from clone 738P15 on chromosome 20p11.2-11.22. Contains a putative new gene, the CD39L2 for nucleoside phosphatase D39-like 2, and the (putative?) IL-6SAG gene in the CD39L2 3 UTR. Contains ESTs, an STS, GSSs and | 0.279 | 0.552 | 2.673362705 | 39876_at |
| 39424_at | tumor | 0.4128952 | Cluster Incl. U70321:Human herpesvirus entry mediator mRNA, complete cds /cds=(293,1144) /gb=U70321 /gi=2138189 /ug=Hs.130227 /len=1698 | -0.107 | 0.54 | 2.620337594 | 39424_at |
| 38469_at | tumor | 0.4088627 | Cluster Incl. M35252:Human CO-029 /cds=(137,850) /gb=M35252 /gi=180925 /ug=Hs.84072 /len=1083 | -0.079 | 0.218 | 6.851780729 | 38469_at |
| 34570_at | tumor | 0.4087165 | Cluster Incl. S79522: ubiquitin carboxyl extension protein [human, mRNA, 540 nt] /cds=(38,508) /gb=S79522 /gi=243887 /ug=Hs.3297 /len=540 | 0.066 | 0.141 | 7.17222538 | 34570_at |
| 34609_g_at | tumor | 0.4086918 | Cluster Incl. M24194:Human MHC protein homologous to chicken B complex protein mRNA, complete cds /cds=UNKNOWN /gb=M24194 /gi=187701 /ug=Hs.5662 /len=1093 | 0.292 | 0.304 | 8.263039604 | 34609_g_at |
| 1199_at | tumor | 0.4085791 | D13748 /FEATURE= /DEFINITION=HUM4AI Human mRNA for eukaryotic initiation factor 4AI | 0.278 | 0.086 | 4.641673692 | 1199_at |
| 31584_at | tumor | 0.4070587 | Cluster Incl. X16064:Human mRNA for translationally controlled tumor protein /cds=(94,612) /gb=X16064 /gi=37495 /ug=Hs.119252 /len=830 | 0.313 | 0.201 | 10.45351969 | 31584_at |
| 38708_at | tumor | 0.4057463 | Cluster Incl. AF054183:Homo sapiens GTP binding protein mRNA, complete cds /cds=(114,764) /gb=AF054183 /gi=4092053 /ug=Hs.10842 /len=1119 | 0.254 | 0.065 | 4.398403397 | 38708_at |

FIG. 3P

| Label | Distinction | Distance | Desc | pearson corr Tumor | pearson corr Normal | Mean TN Ratio | Accession |
|---|---|---|---|---|---|---|---|
| 37725_at | tumor | 0.4027161 | Cluster Incl. X74008:H.sapiens mRNA for protein phosphatase 1 gamma /cds=(154,1125) /gb=X74008 /gi=402777 /ug=Hs.79081 /len=2263 | 0.209 | 0.072 | 2.740506596 | 37725_at |
| 296_at | tumor | 0.4015064 | Tubulin, Beta | 0.072 | 0.079 | 4.395529103 | 296_at |
| 36060_at | tumor | 0.4008856 | Cluster Incl. U51920:Human signal recognition particle (SRP54) mRNA, complete cds /cds=(71,1585) /gb=U51920 /gi=1256819 /ug=Hs.49346 /len=2000 | 0.185 | 0.524 | 2.982294368 | 36060_at |
| 33709_at | tumor | 0.3988998 | Cluster Incl. AF067224:Homo sapiens cGMP phosphodiesterase A2 (PDE9A) mRNA, complete cds /cds=(11,1612) /gb=AF067224 /gi=3327969 /ug=Hs.18953 /len=1826 | -0.06 | 0.257 | 2.184576406 | 33709_at |
| 32744_at | tumor | 0.3988082 | Cluster Incl. AI526078:DU3.2-7.G08.r Homo sapiens cDNA, 5 end /clone_end=5 /gb=AI526078 /gi=4440196 /ug=Hs.1948 /len=560 | 0.248 | 0.195 | 22.87853436 | 32744_at |
| 40167_s_at | tumor | 0.3981612 | Cluster Incl. AF038187:Homo sapiens clone 23714 mRNA sequence /cds=UNKNOWN /gb=AF038187 /gi=2795907 /ug=Hs.136644 /len=1642 | 0.248 | -0.002 | 2.391768288 | 40167_s_at |
| 32521_at | tumor | 0.3975499 | Cluster Incl. AF056087:Homo sapiens secreted frizzled related protein mRNA, complete cds /cds=(302,1243) /gb=AF056087 /gi=3033550 /ug=Hs.7306 /len=4458 | 0.019 | 0.377 | 3.977806546 | 32521_at |
| 2035_s_at | tumor | 0.3959207 | M55914 /FEATURE= /DEFINITION=HUMCMYCQ Human c-myc binding protein (MBP-1) mRNA, complete cds | 0.245 | -0.011 | 3.868624316 | 2035_s_at |
| 31385_at | tumor | 0.395815 | Cluster Incl. U14969:Human ribosomal protein L28 mRNA, complete cds /cds=(27,440) /gb=U14969 /gi=550018 /ug=Hs.4437 /len=485 | 0.232 | 0.313 | 18.86734259 | 31385_at |
| 32330_at | tumor | 0.395417 | Cluster Incl. X06617:Human mRNA for ribosomal protein S11 /cds=(15,491) /gb=X06617 /gi=36143 /ug=Hs.182740 /len=543 | 0.3 | 0.191 | 12.84708995 | 32330_at |
| 32436_at | tumor | 0.39411 | Cluster Incl. U14968:Human ribosomal protein L27a mRNA, complete cds /cds=(16,462) /gb=U14968 /gi=550016 /ug=Hs.76064 /len=507 | 0.241 | 0.08 | 16.68956162 | 32436_at |
| 1585_at | tumor | 0.3940217 | M34309 /FEATURE= /DEFINITION=HUMHER3A Human epidermal growth factor receptor (HER3) mRNA, complete cds | 0.166 | 0.217 | 2.445588165 | 1585_at |

FIG. 3Q

| Label | Distinction | Distance | Desc | pearson corr Tumor | pearson corr Normal | Mean TN Ratio | Accession |
|---|---|---|---|---|---|---|---|
| 729_i_at | tumor | 0.3939644 | Mucin 3, Intestinal | 0.268 | 0.149 | 3.298707822 | 729_i_at |
| 35771_at | tumor | 0.3937838 | Cluster Incl. AF049460:Homo sapiens nuclear DEAF-1 related transcriptional regulator protein 8 mRNA, complete cds /cds=(356,2011) /gb=AF049460 /gi=3309564 /ug=Hs.6574 /len=2329 | -0.368 | -0.042 | 2.060006494 | 35771_at |
| 39060_at | tumor | 0.3936828 | Cluster Incl. D38048:Human mRNA for proteasome subunit z, complete cds /cds=(14,847) /gb=D38048 /gi=1531532 /ug=Hs.118065 /len=980 | -0.07 | 0.249 | 2.544541712 | 39060_at |
| 32893_s_at | tumor | 0.3930804 | Cluster Incl. M30474:Human kidney gamma-glutamyl transpeptidase type II mRNA, 3 end /cds=(0,596) /gb=M30474 /gi=183139 /ug=Hs.211824 /len=762 | 0.231 | 0.261 | 3.889047789 | 32893_s_at |
| 40082_at | tumor | 0.392649 | Cluster Incl. D10040:Homo sapiens mRNA for long-chain acyl-CoA synthetase, complete cds /cds=(13,2109) /gb=D10040 /gi=219899 /ug=Hs.154890 /len=3634 | 0.2 | 0.283 | 2.952693137 | 40082_at |
| 40060_r_at | tumor | 0.3924148 | Cluster Incl. AF061258:Homo sapiens LIM protein mRNA, complete cds /cds=(83,1873) /gb=AF061258 /gi=3108092 /ug=Hs.154103 /len=3287 | 0.384 | -0.093 | 5.674432709 | 40060_r_at |
| 38683_s_at | tumor | 0.3916033 | Cluster Incl. AB029008:Homo sapiens mRNA for KIAA1085 protein, partial cds /cds=(0,1755) /gb=AB029008 /gi=5689506 /ug=Hs.106711 /len=5455 | 0.128 | 0.457 | 2.946927135 | 38683_s_at |
| 39415_at | tumor | 0.3914697 | Cluster Incl. X72727:H.sapiens tunp mRNA for transformation upregulated nuclear protein /cds=(209,1603) /gb=X72727 /gi=460788 /ug=Hs.129548 /len=2830 | 0.264 | 0.205 | 3.338974502 | 39415_at |
| 33267_at | tumor | 0.3905613 | Cluster Incl. AF035315:Homo sapiens clone 23664 and 23905 mRNA sequence /cds=UNKNOWN /gb=AF035315 /gi=2661077 /ug=Hs.180737 /len=1331 | 0.015 | 0.517 | 2.570074675 | 33267_at |
| 37713_at | tumor | 0.3902019 | Cluster Incl. L07548:Human aminoacylase-1 (ACY1) mRNA, complete cds /cds=(61,1287) /gb=L07548 /gi=178070 /ug=Hs.79 /len=1415 | 0.147 | 0 | 2.184175153 | 37713_at |
| 36131_at | tumor | 0.3901381 | Cluster Incl. AJ012008:Homo sapiens genes encoding RNCC protein, DDAH protein, Ly6-C protein, Ly6-D protein and immunoglobulin receptor /cds=(218,943) /gb=AJ012008 /gi=5304874 /ug=Hs.74276 /len=1200 | 0.216 | 0.383 | 7.29812305 | 36131_at |

FIG. 3R

| Label | Distinction | Distance | Desc | pearson corr Tumor | pearson corr Normal | Mean TN Ratio | Accession |
|---|---|---|---|---|---|---|---|
| 33332_at | tumor | 0.3896918 | Cluster Incl. Z93241:dJ222E13.1a.1 (C-terminal part of novel protein dJ222E13.1) (partial isoform 1) /cds=(0,406) /gb=Z93241 /gi=4826450 /ug=Hs.185057 /len=734 | -0.005 | -0.201 | 5.120118560 | 33332_at |
| 31948_at | tumor | 0.388877 | Cluster Incl. X79563:H.sapiens 8.2kDa differentiation factor mRNA /cds=(60,353) /gb=X79563 /gi=499069 /ug=Hs.169301 /len=465 | 0.031 | -0.024 | 2.233808445 | 31948_at |
| 34348_at | tumor | 0.3888636 | Cluster Incl. U78095:Homo sapiens placental bikunin mRNA, complete cds /cds=(300,1058) /gb=U78095 /gi=2065528 /ug=Hs.31439 /len=1525 | 0.244 | 0.549 | 5.741468775 | 34348_at |
| 461_at | tumor | 0.3877752 | U70063 /FEATURE= /DEFINITION=HSU70063 Human acid ceramidase mRNA, complete cds | -0.022 | 0.365 | 2.975299655 | 461_at |
| 1313_at | tumor | 0.3875693 | D38048 /FEATURE= /DEFINITION=D38048 Human mRNA for proteasome subunit z, complete cds | 0.228 | 0.135 | 2.461968825 | 1313_at |
| 1890_at | tumor | 0.3875513 | AB000584 /FEATURE= /DEFINITION=AB000584 Homo sapiens mRNA for TGF-beta superfamily protein, complete cds | 0.182 | 0.016 | 6.862314546 | 1890_at |
| 1985_s_at | tumor | 0.3873661 | X73066 /FEATURE=cds /DEFINITION=HSNM23H1A H.sapiens NM23-H1 mRNA | 0.014 | -0.098 | 3.417745333 | 1985_s_at |
| 1180_g_at | tumor | 0.386874 | Heat Shock Protein, 70 Kda | 0.299 | 0.103 | 6.316278157 | 1180_g_at |
| 1840_g_at | tumor | 0.3866314 | Ras-Like Protein Tc4 | 0.185 | 0.173 | 4.037992463 | 1840_g_at |
| 39073_at | tumor | 0.3850662 | Cluster Incl. AL038662:DKFZp566I0346_r1 Homo sapiens cDNA, 5 end /clone=DKFZp566I0346 /clone_end=5 /gb=AL038662 /gi=5407828 /uc=Hs.118638 /len=764 | 0.195 | 0.043 | 2.631394667 | 39073_at |
| 31950_at | tumor | 0.3846685 | Cluster Incl. Y00345:Human mRNA for polyA binding protein /cds=(502,2403) /gb=Y00345 /gi=35569 /ug=Hs.172182 /len=2848 | 0.266 | 0.214 | 4.666766583 | 31950_at |
| 36972_at | tumor | 0.3841428 | Cluster Incl. X92098:H.sapiens mRNA for transmembrane protein rnp24 /cds=(27,632) /gb=X92098 /gi=1212964 /ug=Hs.75914 /len=780 | -0.042 | 0.388 | 4.661581098 | 36972_at |
| 32573_at | tumor | 0.3841082 | Cluster Incl. AL021546:Human DNA sequence from BAC 15E1 on chromosome 12. Contains Cytochrome C Oxidase Polypeptide Vla-liver precursor gene, 60S ribosomal protein L31 pseudogene, pre-mRNA splicing factor SRp30c gene, two putative genes, ESTs, STSs and pu | 0.158 | 0.403 | 3.391398068 | 32573_at |

FIG. 3S

| Label | Distinction | Distance | Desc | pearson corr Tumor | pearson corr Normal | Mean TN Ratio | Accession |
|---|---|---|---|---|---|---|---|
| 820_at | tumor | 0.3840772 | U77604 /FEATURE= /DEFINITION=HSU77604 Homo sapiens microsomal glutathione S-transferase 2 (MGST2) mRNA, complete cds | 0.228 | 0.181 | 3.208715148 | 820_at |
| 442_at | tumor | 0.3839712 | X15187 /FEATURE=cds /DEFINITION=HSTRA1 Human tra1 mRNA for human homologue of murine tumor rejection antigen gp96 | 0.334 | 0.352 | 5.871980525 | 442_at |
| 39169_at | tumor | 0.3832234 | Cluster Incl. AF054184:Homo sapiens Sec61 gamma mRNA, complete cds /cds=(90,296) /gb=AF054184 /gi=4092055 /ug=Hs.9950 /len=452 | 0.186 | 0.478 | 3.193270638 | 39169_at |
| 33117_r_at | tumor | 0.3829818 | Cluster Incl. AA977163:oq25a04.s1 Homo sapiens cDNA, 3 end /clone=IMAGE-1587342 /clone_end=3 /gb=AA977163 /gi=3154609 /ug=Hs.82148 /len=524 | 0.242 | 0.294 | 12.94994484 | 33117_r_at |
| 37668_at | tumor | 0.3828614 | Cluster Incl. M69039:Human pre-mRNA splicing factor SF2p32, complete sequence /cds=(0,836) /gb=M69039 /gi=338042 /ug=Hs.78614 /len=1226 | 0.188 | 0.148 | 2.574922076 | 37668_at |
| 32878_f_at | tumor | 0.3825053 | Cluster Incl. AA524802:nh33h11.s1 Homo sapiens cDNA /clone=IMAGE-954213 /gb=AA524802 /gi=2265730 /ug=Hs.203907 /len=500 | 0.085 | 0.441 | 4.051296596 | 32878_f_at |
| 36104_at | tumor | 0.3814112 | Cluster Incl. AA526497:ni96d07.s1 Homo sapiens cDNA, 3 end /clone=IMAGE-984685 /clone_end=3 /gb=AA526497 /gi=2268566 /ug=Hs.73818 /len=582 | 0.134 | 0.18 | 3.764566372 | 36104_at |
| 33821_at | tumor | 0.3807337 | Cluster Incl. AL034374:Human DNA sequence from clone 483K16 on chromosome 6p12.1-21.1. Contains (parts of) two novel genes, 40S Ribosomal protein S16 and 60S Ribosomal protein L31 pseudogenes, ESTs, STSs, GSSs and a putative CpG island /cds=(0,703) /gb=AL | 0.162 | 0.585 | 5.702736152 | 33821_at |
| 33116_f_at | tumor | 0.3804647 | Cluster Incl. AA977163:oq25a04.s1 Homo sapiens cDNA, 3 end /clone=IMAGE-1587342 /clone_end=3 /gb=AA977163 /gi=3154609 /ug=Hs.82148 /len=524 | 0.282 | 0.161 | 19.53398824 | 33116_f_at |
| 34317_g_at | tumor | 0.3801189 | Cluster Incl. W52024:zd13a03.s1 Homo sapiens cDNA, 3 end /clone=IMAGE-340492 /clone_end=3 /gb=W52024 /gi=1350030 /ug=Hs.2953 /len=531 | 0.277 | 0.165 | 16.63336377 | 34317_g_at |
| 31932_f_at | tumor | 0.3795915 | Cluster Incl. M90357:Human basic transcription factor 3a (BTF3a) gene /cds=(0,476) /gb=M90357 /gi=457435 /ug=Hs.166033 /len=487 | 0.278 | 0.25 | 3.074534647 | 31932_f_at |

FIG. 3T

| Label | Distinction | Distance | Desc | pearson corr Tumor | pearson corr Normal | Mean TN Ratio | Accession |
|---|---|---|---|---|---|---|---|
| 39331_at | tumor | 0.3794093 | Cluster Incl. X79535:H.sapiens mRNA for beta tubulin, clone nuk_278 /cds=(63,1400) /gb=X79535 /gi=496886 /ug=Hs.119076 /len=1594 | 0.054 | 0.072 | 2.938805926 | 39331_at |
| 34593_g_at | tumor | 0.3792694 | Cluster Incl. M13932:Human ribosomal protein S17 mRNA, complete cds /cds=(25,432) /gb=M13932 /gi=337500 /ug=Hs.5174 /len=477 | -0.03 | 0.065 | 26.69643889 | 34593_g_at |
| 36821_at | tumor | 0.3792585 | Cluster Incl. AL050367:Homo sapiens mRNA; cDNA DKFZp564A026 (from clone DKFZp564A026) /cds=UNKNOWN /gb=AL050367 /gi=4914600 /ug=Hs.66762 /len=3938 | -0.223 | -0.05 | 2.047560654 | 36821_at |
| 41235_at | tumor | 0.3775312 | Cluster Incl. AL022312:dJ1104E15.2 (activating transcription factor 4 (tax-responsive enhancer element B67)) /cds=(882,1937) /gb=AL022312 /gi=4914501 /ug=Hs.181243 /len=2016 | 0.184 | 0.226 | 4.058312453 | 41235_at |
| 38681_at | tumor | 0.3772356 | Cluster Incl. U62962:Human Int-6 mRNA, complete cds /cds=(22,1359) /gb=U62962 /gi=2114362 /ug=Hs.106673 /len=1510 | 0.184 | 0.113 | 3.45664036 | 38681_at |
| 35298_at | tumor | 0.3771401 | Cluster Incl. U54558:Homo sapiens translation initiation factor eIF3 p66 subunit mRNA, complete cds /cds=(84,1730) /gb=U54558 /gi=2351377 /ug=Hs.55682 /len=1863 | -0.154 | 0.067 | 3.479691335 | 35298_at |
| 39154_at | tumor | 0.3771229 | Cluster Incl. AI952982:wp98b06.x1 Homo sapiens cDNA, 3 end /clone=IMAGE-2469779 /clone_end=3 /gb=AI952982 /gi=5745292 /ug=Hs.9701 /len=816 | 0.173 | 0.214 | 5.55953557 | 39154_at |
| 41772_at | tumor | 0.3769324 | Cluster Incl. M68840:Human monoamine oxidase A (MAOA) mRNA, complete cds /cds=(73,1656) /gb=M68840 /gi=187352 /ug=Hs.183109 /len=1949 | 0.079 | 0.046 | 2.277319943 | 41772_at |
| 34643_at | tumor | 0.3756595 | Cluster Incl. M58458:Human ribosomal protein S4 (RPS4X) isoform mRNA, complete cds /cds=(35,826) /gb=M58458 /gi=337509 /ug=Hs.75344 /len=888 | 0.262 | 0.323 | 4.372274258 | 34643_at |
| 39339_at | tumor | 0.3745244 | Cluster Incl. AB018335:Homo sapiens mRNA for KIAA0792 protein, complete cds /cds=(250,2673) /gb=AB018335 /gi=3882304 /ug=Hs.119387 /len=4074 | -0.189 | 0.262 | 1.885837917 | 39339_at |

FIG. 3U

| Label | Distinction | Distance | Desc | pearson corr Tumor | pearson corr Normal | Mean TN Ratio | Accession |
|---|---|---|---|---|---|---|---|
| 31573_at | tumor | 0.3742524 | Cluster Incl. M64716:Human ribosomal protein S25 mRNA, complete cds /cds=(71,448) /gb=M64716 /gi=337507 /ug=Hs.113029 /len=497 | 0.012 | 0.198 | 12.01203742 | 31573_at |
| 31722_at | tumor | 0.3731095 | Cluster Incl. AL022326:dJ333H23.1.1 (60S Ribosomal Protein L3) /cds=(6,1217) /gb=AL022326 /gi=3550039 /ug=Hs.119598 /len=1274 | 0.288 | 0.269 | 12.47944544 | 31722_at |
| 36676_at | tumor | 0.3729933 | Cluster Incl. AL031659:dJ343K2.2.1 (ribophorin II (isoform 1)) /cds=(284,2179) /gb=AL031659 /gi=4468296 /ug=Hs.75722 /len=2488 | -0.109 | 0.538 | 4.477573064 | 36676_at |
| 37068_at | tumor | 0.3728833 | Cluster Incl. U24577:Human LDL-phospholipase A2 mRNA, complete cds /cds=(216,1541) /gb=U24577 /gi=1314245 /ug=Hs.93304 /len=1561 | 0.138 | -0.124 | 2.616985842 | 37068_at |
| 35125_at | tumor | 0.3715125 | Cluster Incl. X67309:H.sapiens gene for ribosomal protein S6 /cds=(42,791) /gb=X67309 /gi=36147 /ug=Hs.120856 /len=829 | 0.332 | 0.225 | 11.50949625 | 35125_at |
| 33676_at | tumor | 0.3697996 | Cluster Incl. X15940:Human mRNA for ribosomal protein L31 /cds=(7,384) /gb=X15940 /gi=36129 /ug=Hs.184014 /len=414 | 0.293 | 0.264 | 16.71510029 | 33676_at |
| 32276_at | tumor | 0.3695736 | Cluster Incl. X03342:Human mRNA for ribosomal protein L32 /cds=(34,441) /gb=X03342 /gi=36131 /ug=Hs.169793 /len=505 | 0.285 | 0.154 | 13.21268696 | 32276_at |
| 1653_at | tumor | 0.3693465 | M84711 /FEATURE= /DEFINITION=HUMFTE1A Human v-fos transformation effector protein (Fte-1), mRNA complete cds | 0.29 | 0.27 | 16.38712274 | 1653_at |
| 33824_at | tumor | 0.3685238 | Cluster Incl. X74929:H.sapiens KRT8 mRNA for keratin 8 /cds=(59,1510) /gb=X74929 /gi=400415 /ug=Hs.234705 /len=1752 | 0.111 | 0.424 | 4.505763863 | 33824_at |
| 36660_at | tumor | 0.3678429 | Cluster Incl. AF000231:Homo sapiens rab11a GTPase mRNA, complete cds /cds=(67,717) /gb=AF000231 /gi=2149974 /ug=Hs.75618 /len=2333 | 0.296 | 0.233 | 2.483950954 | 36660_at |
| 35342_at | tumor | 0.3675957 | Cluster Incl. AF052159:Homo sapiens clone 24416 mRNA sequence /cds=UNKNOWN /gb=AF052159 /gi=3360470 /ug=Hs.5957 /len=1277 | -0.208 | 0.064 | 2.862626776 | 35342_at |

FIG. 3V

| Label | Distinction | Distance | Desc | pearson corr Tumor | pearson corr Normal | Mean TN Ratio | Accession |
|---|---|---|---|---|---|---|---|
| 35748_at | tumor | 0.3675866 | Cluster Incl. X60489:Human mRNA for elongation factor-1-beta /cds=(235,912) /gb=X60489 /gi=31099 /ug=Hs.63552 /len=964 | -0.006 | -0.022 | 4.529328198 | 35748_at |
| 32530_at | tumor | 0.3663831 | Cluster Incl. X56468:Human mRNA for 14.3.3 protein, a protein kinase regulator /cds=(125,862) /gb=X56468 /gi=23221 /ug=Hs.74405 /len=1862 | -0.022 | 0.218 | 4.221699294 | 32530_at |
| 36685_at | tumor | 0.3660444 | Cluster Incl. W63793:zc55a10.r1 Homo sapiens cDNA, 5 end /clone=IMAGE-326202 /clone_end=5 /gb=W63793 /gi=1371127 /ug=Hs.75744 /len=597 | -0.274 | 0.402 | 3.329824121 | 36685_at |
| 32485_at | tumor | 0.3656924 | Cluster Incl. X00371:Human myoglobin gene (exon 1) (and joined CDS) /cds=(70,534) /gb=X00371 /gi=34607 /ug=Hs.118836 /len=1066 | 0.137 | -0.1 | 2.321165607 | 32485_at |
| 41403_at | tumor | 0.3656602 | Cluster Incl. AI032612:ow17e07.x1 Homo sapiens cDNA, 3 end /clone=IMAGE-1647108 /clone_end=3 /gb=AI032612 /gi=3253738 /ug=Hs.105465 /len=582 | 0.082 | 0.13 | 2.589890843 | 41403_at |
| 324_f_at | tumor | 0.3654817 | Transcription Factor Btf3b | 0.261 | 0.167 | 4.159637716 | 324_f_at |
| 41140_at | tumor | 0.3654315 | Cluster Incl. U05875:Human clone pSK1 interferon gamma receptor accessory factor-1 (AF-1) mRNA, complete cds /cds=(648,1661) /gb=U05875 /gi=463549 /ug=Hs.177559 /len=2214 | 0.224 | 0.447 | 3.88676749 | 41140_at |
| 37364_at | tumor | 0.3651259 | Cluster Incl. U72511:Human B-cell receptor associated protein (hBAP) mRNA, partial cds /cds=(0,637) /gb=U72511 /gi=1673513 /ug=Hs.7771 /len=969 | 0.269 | 0.182 | 4.010515654 | 37364_at |
| 38542_at | tumor | 0.362848 | Cluster Incl. U89322:Homo sapiens nucleophosmin phosphoprotein/B23 (NPM) gene /cds=(96,980) /gb=U89322 /gi=2745722 /ug=Hs.173205 /len=1300 | 0.297 | 0.098 | 6.805234346 | 38542_at |
| 36358_at | tumor | 0.3609304 | Cluster Incl. U09953:Human ribosomal protein L9 mRNA, complete cds /cds=(29,607) /gb=U09953 /gi=1323732 /ug=Hs.157850 /len=712 | 0.245 | 0.259 | 14.777569024 | 36358_at |
| 35055_at | tumor | 0.3608571 | Cluster Incl. X53281:H.sapiens BTF3b mRNA /cds=(239,727) /gb=X53281 /gi=29506 /ug=Hs.101025 /len=952 | 0.127 | 0.04 | 5.949070307 | 35055_at |

FIG. 3w

| Label | Distinction | Distance | Desc | pearson corr Tumor | pearson corr Normal | Mean TN Ratio | Accession |
|---|---|---|---|---|---|---|---|
| 36846_s_at | tumor | 0.3591617 | Cluster Incl. AA121509:zk88c10.s1 Homo sapiens cDNA, 3 end /clone=IMAGE-489906 /clone_end=3 /gb=AA121509 /gi=1679123 /ug=Hs.70830 /len=593 | 0.183 | 0.129 | 2.518916778 | 36846_s_at |
| 35631_at | tumor | 0.3591142 | Cluster Incl. U37689:Human RNA polymerase II subunit (hsRPB8) mRNA, complete cds /cds=(165,617) /gb=U37689 /gi=1017822 /ug=Hs.3128 /len=867 | 0.05 | -0.019 | 2.298430204 | 35631_at |
| 34307_at | tumor | 0.3584586 | Cluster Incl. U81006:Human p76 mRNA, complete cds /cds=(133,2124) /gb=U81006 /gi=1737489 /ug=Hs.28757 /len=2391 | 0.279 | 0.542 | 3.630474292 | 34307_at |
| 37311_at | tumor | 0.3576932 | Cluster Incl. AF010400:untitled /cds=(50,1063) /gb=AF010400 /gi=2612878 /ug=Hs.77290 /len=1242 | 0.116 | 0.381 | 3.417049203 | 37311_at |
| 41526_at | tumor | 0.3574864 | Cluster Incl. AF072836:Homo sapiens Sox-like transcriptional factor mRNA, complete cds /cds=(18,1043) /gb=AF072836 /gi=3329481 /ug=Hs.32317 /len=1232 | 0.07 | 0.221 | 2.657320297 | 41526_at |
| 39089_at | tumor | 0.3558676 | Cluster Incl. Y07604:H.sapiens mRNA for nucleoside-diphosphate kinase /cds=(11,574) /gb=Y07604 /gi=1945761 /ug=Hs.9235 /len=879 | 0.111 | 0.462 | 4.271903719 | 39089_at |
| 41696_at | tumor | 0.3557874 | Cluster Incl. AI620381:tu94d05.x1 Homo sapiens cDNA, 3 end /clone=IMAGE-2258697 /clone_end=3 /gb=AI620381 /gi=4629507 /ug=Hs.12770 /len=652 | 0.195 | 0.072 | 2.598160606 | 41696_at |
| 39032_at | tumor | 0.3557684 | Cluster Incl. AJ222700:Homo sapiens mRNA for TSC-22 protein /cds=(191,625) /gb=AJ222700 /gi=2665384 /ug=Hs.114360 /len=1725 | -0.219 | 0.143 | 3.238221638 | 39032_at |
| 39767_at | tumor | 0.3541991 | Cluster Incl. D13627:Human mRNA for KIAA0002 gene, complete cds /cds=(28,1674) /gb=D13627 /gi=286010 /ug=Hs.15071 /len=1821 | 0.085 | 0.3 | 3.376977214 | 39767_at |
| 429_f_at | tumor | 0.3537521 | X00734 /FEATURE=cds /DEFINITION=HSREP10 Human beta-tubulin gene (5-beta) with ten Alu family members | 0.172 | 0.277 | 3.361363543 | 429_f_at |
| 33679_f_at | tumor | 0.353048 | Cluster Incl. X02344:Homo sapiens beta 2 gene /cds=(0,1337) /gb=X02344 /gi=37493 /ug=Hs.184582 /len=1338 | 0.294 | 0.339 | 3.772352023 | 33679_f_at |
| 38084_at | tumor | 0.3527254 | Cluster Incl. AA648295:ns20e08.s1 Homo sapiens cDNA, 3 end /clone=IMAGE-1184198 /clone_end=3 /gb=AA648295 /gi=2574724 /ug=Hs.8123 /len=723 | 0.161 | 0.268 | 4.228831566 | 38084_at |

FIG. 3X

| Label | Distinction | Distance | Desc | pearson corr Tumor | pearson corr Normal | Mean TN Ratio | Accession |
|---|---|---|---|---|---|---|---|
| 38455_at | tumor | 0.3505016 | Cluster Incl. AL049650:dJ734P14.2.1 (snRNP (small nuclear ribonucleoprotein particle) protein B) /cds=(129,824) /gb=AL049650 /gi=5123801 /ug=Hs.83753 /len=1119 | 0.179 | 0.308 | 3.860770183 | 38455_at |
| 40782_at | tumor | 0.3504959 | Cluster Incl. AF061741:Homo sapiens retinal short-chain dehydrogenase/reductase retSDR1 mRNA, complete cds /cds=(54,962) /gb=AF061741 /gi=3450827 /ug=Hs.17144 /len=1401 | 0.128 | 0.342 | 3.449768695 | 40782_at |
| 1739_at | tumor | 0.3499207 | M99487 /FEATURE= /DEFINITION=HUMPSM Human prostate-specific membrane antigen (PSM) mRNA, complete cds | 0.195 | 0.158 | 7.185385537 | 1739_at |
| 34400_at | tumor | 0.3496588 | Cluster Incl. AI540957:PEC1.2_15_G03.r Homo sapiens cDNA, 5 end /clone_end=5 /gb=AI540957 /gi=4458330 /ug=Hs.3709 /len=778 | 0.164 | 0.346 | 6.921111193 | 34400_at |
| 40189_at | tumor | 0.3495235 | Cluster Incl. M93651:Human set gene, complete cds /cds=(3,836) /gb=M93651 /gi=338038 /ug=Hs.145279 /len=2562 | 0.335 | 0.31 | 3.071882349 | 40189_at |
| 1081_at | tumor | 0.3492451 | M33764 /FEATURE=cds /DEFINITION=HUMSODB Human ornithine decarboxylase gene, complete cds | 0.173 | 0.049 | 2.879930157 | 1081_at |
| 35622_at | tumor | 0.3486272 | Cluster Incl. AB001451:Homo sapiens mRNA for Sck, partial cds /cds=(0,1622) /gb=AB001451 /gi=3080543 /ug=Hs.30965 /len=2358 | 0.038 | 0.187 | 1.811790207 | 35622_at |
| 41750_at | tumor | 0.3483896 | Cluster Incl. D49489:Human mRNA for protein disulfide isomerase-related protein P5, complete cds /cds=(94,1416) /gb=D49489 /gi=1136742 /ug=Hs.182429 /len=1862 | 0.355 | 0.311 | 3.775130584 | 41750_at |
| 38791_at | tumor | 0.3479714 | Cluster Incl. D29643:Human mRNA for KIAA0115 gene, complete cds /cds=(106,1476) /gb=D29643 /gi=473936 /ug=Hs.89674 /len=1668 | 0.341 | 0.153 | 4.187784619 | 38791_at |
| 38840_s_at | tumor | 0.3475054 | Cluster Incl. L10678:Human profilin II mRNA, complete cds /cds=(13,435) /gb=L10678 /gi=190387 /ug=Hs.91747 /len=1693 | 0.013 | 0.376 | 2.723725596 | 38840_s_at |
| 36160_s_at | tumor | 0.3465356 | Cluster Incl. U81561:Human protein tyrosine phosphatase receptor pi (PTPRP) mRNA, complete cds /cds=(42,3038) /gb=U81561 /gi=2351575 /ug=Hs.74624 /len=4699 | 0.17 | 0.352 | 2.233111518 | 36160_s_at |

FIG. 3Y

| Label | Distinction | Distance | Desc | pearson corr Tumor | pearson corr Normal | Mean TN Ratio | Accession |
|---|---|---|---|---|---|---|---|
| 38482_at | tumor | 0.346188 | Cluster Incl. AJ011497:Homo sapiens mRNA for Claudin-7 /cds=(334,969) /gb=AJ011497 /gi=4128014 /ug=Hs.84359 /len=1207 | 0.127 | -0.137 | 2.971901936 | 38482_at |
| 36135_at | tumor | 0.3460066 | Cluster Incl. U86602:Human nucleolar protein p40 mRNA, complete cds /cds=(142,1062) /gb=U86602 /gi=1835785 /ug=Hs.74407 /len=1325 | -0.124 | 0.196 | 2.178186462 | 36135_at |
| 34310_at | tumor | 0.3458404 | Cluster Incl. Y00486:Human APRT gene for adenine phosphoribosyltransferase /cds=(71,613) /gb=Y00486 /gi=28818 /ug=Hs.28914 /len=841 | 0.185 | 0.212 | 2.874784249 | 34310_at |
| 262_at | tumor | 0.3455422 | M21154 /FEATURE=mRNA /DEFINITION=HUMAMD Human S-adenosylmethionine decarboxylase mRNA, complete cds | 0.294 | 0.262 | 3.562333688 | 262_at |
| 38589_i_at | tumor | 0.3441889 | Cluster Incl. M14630:Human prothymosin alpha mRNA, complete cds /cds=UNKNOWN /gb=M14630 /gi=339690 /ug=Hs.182371 /len=1200 | 0.148 | 0.1 | 3.976041314 | 38589_i_at |
| 36093_at | tumor | 0.3439161 | Cluster Incl. AB014514:Homo sapiens mRNA for KIAA0614 protein, partial cds /cds=(0,4893) /gb=AB014514 /gi=3327041 /ug=Hs.7314 /len=7084 | 0.125 | 0.522 | 2.073962106 | 36093_at |
| 37306_at | tumor | 0.3432021 | Cluster Incl. D38549:Human mRNA for KIAA0068 gene, partial cds /cds=(0,3816) /gb=D38549 /gi=559702 /ug=Hs.77257 /len=4379 | 0.225 | 0.267 | 2.395640079 | 37306_at |
| 33667_at | tumor | 0.3431543 | Cluster Incl. X52851:Human cyclophilin gene for cyclophilin (EC 5.2.1.8) /cds=(44,541) /gb=X52851 /gi=30167 /ug=Hs.182937 /len=753 | -0.071 | 0.066 | 2.949504503 | 33667_at |
| 32434_at | tumor | 0.3431265 | Cluster Incl. D10522:Homo sapiens mRNA for 80K-L protein, complete cds /cds=(369,1367) /gb=D10522 /gi=219893 /ug=Hs.75607 /len=2589 | 0.038 | 0.32 | 2.744900393 | 32434_at |
| 33845_at | tumor | 0.3424653 | Cluster Incl. W28483:W28483.47e11 Homo sapiens cDNA /gb=W28483 /gi=1308431 /ug=Hs.238542 /len=926 | 0.267 | 0.205 | 3.809194987 | 33845_at |
| 39113_at | tumor | 0.3424093 | Cluster Incl. AI262789:qk35e02.x1 Homo sapiens cDNA, 3 end /clone=IMAGE-1870970 /clone_end=3 /gb=AI262789 /gi=3870992 /ug=Hs.93659 /len=614 | 0.314 | 0.246 | 3.583660645 | 39113_at |

FIG. 3Z

| Label | Distinction | Distance | Desc | pearson corr Tumor | pearson corr Normal | Mean TN Ratio | Accession |
|---|---|---|---|---|---|---|---|
| 38473_at | tumor | 0.3423658 | Cluster Incl. M63180:Human threonyl-tRNA synthetase mRNA, complete cds /cds=(138,2276) /gb=M63180 /gi=339679 /ug=Hs.84131 /len=2644 | 0.026 | 0.048 | 2.292500133 | 38473_at |
| 37040_at | tumor | 0.3422888 | Cluster Incl. D42041:Human mRNA for KIAA0088 gene, partial cds /cds=(0,2832) /gb=D42041 /gi=577294 /ug=Hs.76847 /len=3820 | -0.039 | 0.325 | 3.350713741 | 37040_at |
| 34865_at | tumor | 0.3417016 | Cluster Incl. AI360249:qy84f07.x1 Homo sapiens cDNA, 3 end /clone=IMAGE-2018725 /clone_end=3 /gb=AI360249 /gi=4111870 /ug=Hs.49767 /len=530 | -0.28 | 0.062 | 2.155781791 | 34865_at |
| 34050_at | tumor | 0.3415101 | Cluster Incl. AC003034:Homo sapiens Chromosome 16 BAC clone CIT987SK-A-923A4 /cds=(27,713) /gb=AC003034 /gi=3219338 /ug=Hs.98732 /len=965 | 0.063 | -0.201 | 4.985328073 | 34050_at |
| 40160_at | tumor | 0.3413308 | Cluster Incl. AL080109:Homo sapiens mRNA; cDNA DKFZp586G1822 (from clone DKFZp586G1822) /cds=(0,303) /gb=AL080109 /gi=5262535 /ug=Hs.15832 /len=2362 | 0.29 | 0.184 | 2.015136448 | 40160_at |
| 36614_at | tumor | 0.3405289 | Cluster Incl. X87949:H.sapiens mRNA for BiP protein /cds=(222,2183) /gb=X87949 /gi=1143491 /ug=Hs.75410 /len=2537 | 0.253 | 0.47 | 6.536962688 | 36614_at |
| 32316_s_at | tumor | 0.3402734 | Cluster Incl. X15183:Human mRNA for 90-kDa heat-shock protein /cds=(60,2258) /gb=X15183 /gi=32487 /ug=Hs.180532 /len=2912 | 0.19 | 0.292 | 6.345104559 | 32316_s_at |
| 34797_at | tumor | 0.3399872 | Cluster Incl. AF014402:Homo sapiens type-2 phosphatidic acid phosphatase alpha-1 (PAP2-a1) mRNA, complete cds /cds=(341,1195) /gb=AF014402 /gi=3123847 /ug=Hs.41569 /len=1545 | 0.297 | 0.488 | 4.110541979 | 34797_at |
| 35175_f_at | tumor | 0.3399449 | Cluster Incl. X70940:H.sapiens mRNA for elongation factor 1 alpha-2 /cds=(83,1474) /gb=X70940 /gi=38455 /ug=Hs.2642 /len=1755 | 0.202 | 0.323 | 5.510788963 | 35175_f_at |
| 36965_at | tumor | 0.3396931 | Cluster Incl. U13616:Human ankyrin G (ANK-3) mRNA, complete cds /cds=(192,13325) /gb=U13616 /gi=608024 /ug=Hs.75893 /len=14770 | -0.18 | 0.163 | 3.450881364 | 36965_at |
| 35127_at | tumor | 0.3395998 | Cluster Incl. AI039144:ox31b09.s1 Homo sapiens cDNA, 3 end /clone=IMAGE-1657913 /clone_end=3 /gb=AI039144 /gi=3278338 /ug=Hs.121017 /len=527 | -0.026 | 0.411 | 3.892542355 | 35127_at |

FIG. 3A2

| Label | Distinction | Distance | Desc | pearson corr Tumor | pearson corr Normal | Mean TN Ratio | Accession |
|---|---|---|---|---|---|---|---|
| 347_s_at | tumor | 0.3390279 | D14530 /FEATURE= /DEFINITION=HUMRSPT Human homolog of yeast ribosomal protein S28, complete cds | 0.26 | 0.238 | 22.29926093 | 347_s_at |
| 38763_at | tumor | 0.3390262 | Cluster Incl. L29254:Human (clone P1-5) L-iditol-2 dehydrogenase gene /cds=(137,1210) /gb=L29254 /gi=808013 /ug=Hs.878 /len=2519 | 0.243 | 0.72 | 7.731741394 | 38763_at |
| 39814_s_at | tumor | 0.3381852 | Cluster Incl. AI052724:oz27a12.x1 Homo sapiens cDNA, 3 end /clone=IMAGE-1676542 /clone_end=3 /gb=AI052724 /gi=3308715 /ug=Hs.109201 /len=682 | -0.072 | 0.586 | 9.379391229 | 39814_s_at |
| 39817_s_at | tumor | 0.3379631 | Cluster Incl. AF040105:Homo sapiens RCL (Rcl) mRNA, complete cds /cds=(17,541) /gb=AF040105 /gi=2773296 /ug=Hs.109752 /len=644 | 0.21 | -0.021 | 2.707097863 | 39817_s_at |
| 37761_at | tumor | 0.3379301 | Cluster Incl. AB015020:Homo sapiens mRNA for BAP2-beta protein, complete cds /cds=(93,1655) /gb=AB015020 /gi=4126476 /ug=Hs.7936 /len=2129 | 0.172 | 0.343 | 2.249984546 | 37761_at |
| 34381_at | tumor | 0.3374647 | Cluster Incl. AI708889:as86g01.x1 Homo sapiens cDNA, 3 end /clone=IMAGE-2335632 /clone_end=3 /gb=AI708889 /gi=4998665 /ug=Hs.3462 /len=533 | -0.038 | 0.146 | 6.04597883 | 34381_at |
| 40966_at | tumor | 0.3369613 | Cluster Incl. AF099989:Homo sapiens Ste-20 related kinase SPAK mRNA, complete cds /cds=(173,1816) /gb=AF099989 /gi=3851170 /ug=Hs.199263 /len=3293 | 0.255 | 0.456 | 2.781204316 | 40966_at |
| 39127_f_at | tumor | 0.336122 | Cluster Incl. X73478:H.sapiens hPTPA mRNA /cds=(189,1160) /gb=X73478 /gi=509242 /ug=Hs.94466 /len=2637 | -0.307 | 0.185 | 4.074326718 | 39127_f_at |
| 38441_s_at | tumor | 0.3356962 | Cluster Incl. X59408:H.sapiens, gene for Membrane cofactor protein /cds=UNKNOWN /gb=X59408 /gi=34511 /ug=Hs.83532 /len=3212 | 0.272 | 0.604 | 3.504204287 | 38441_s_at |
| 33431_at | tumor | 0.3353149 | Cluster Incl. U05291:Human fibromodulin mRNA, partial cds /cds=(0,177) /gb=U05291 /gi=450854 /ug=Hs.230 /len=1892 | 0.064 | 0.187 | 2.886202233 | 33431_at |
| 33631_at | tumor | 0.3347965 | Cluster Incl. AF023612:Homo sapiens Dim1p homolog mRNA, complete cds /cds=(126,401) /gb=AF023612 /gi=2565276 /ug=Hs.166152 /len=909 | -0.238 | 0.261 | 1.987081397 | 33631_at |

FIG. 3B2

| Label | Distinction | Distance | Desc | pearson corr Tumor | pearson corr Normal | Mean TN Ratio | Accession |
|---|---|---|---|---|---|---|---|
| 39023_at | tumor | 0.3344533 | Cluster Incl. AF020038:Homo sapiens NADP-dependent isocitrate dehydrogenase (IDH) mRNA, complete cds /cds=(249,1493) /gb=AF020038 /gi=3641397 /ug=Hs.11223 /len=2343 | 0.258 | 0.542 | 4.181921026 | 39023_at |
| 34850_at | tumor | 0.3341891 | Cluster Incl. AB017644:Homo sapiens mRNA for ubiquitin-conjugating enzyme E2, complete cds /cds=(61,684) /gb=AB017644 /gi=4586929 /ug=Hs.4890 /len=1216 | -0.232 | 0.03 | 2.116344454 | 34850_at |
| 32444_at | tumor | 0.3335782 | Cluster Incl. X69392:H.sapiens mRNA for ribosomal protein L26 /cds=(6,443) /gb=X69392 /gi=36114 /ug=Hs.91379 /len=773 | 0.005 | 0.09 | 4.640988303 | 32444_at |
| 40425_at | tumor | 0.3335153 | Cluster Incl. M57730:Human B61 mRNA, complete cds /cds=(73,690) /gb=M57730 /gi=179320 /ug=Hs.1624 /len=1480 | 0.265 | 0.378 | 4.193128117 | 40425_at |
| 41834_g_at | tumor | 0.3334989 | Cluster Incl. AB016492:Homo sapiens hJTB gene, complete cds /cds=(464,904) /gb=AB016492 /gi=3721895 /ug=Hs.6396 /len=1072 | 0.307 | 0.453 | 3.874650229 | 41834_g_at |
| 32395_r_at | tumor | 0.333207 | Cluster Incl. X55954:Human mRNA for HL23 ribosomal protein homologue /cds=(12,434) /gb=X55954 /gi=34193 /ug=Hs.234518 /len=479 | 0.191 | 0.329 | 10.84319336 | 32395_r_at |
| 38789_at | tumor | 0.3330431 | Cluster Incl. L12711:Homo sapiens transketolase (tk) mRNA, complete cds /cds=(98,1969) /gb=L12711 /gi=388890 /ug=Hs.89643 /len=2069 | 0.065 | 0.108 | 1.856348832 | 38789_at |

FIG. 3C2

|  | Raw Data | | | Normalized Data | | |
|---|---|---|---|---|---|---|
|  | Prediction Results | | Success Rate | Prediction Results | | Success Rate |
| 4 Gene | | TT TN | 85.7% (30/35) p = 0.006* | | TT TN | 77.2% (27/35) p = 0.0005 |
|  | PT | 26  4 |  | PT | 19  0 |  |
|  | PN | 1   4 |  | PN | 8   8 |  |
| 16 Gene | | TT TN | 82.9% (29/35) p = 0.047 | | TT TN | 85.7% (30/35) p = 0.0001 |
|  | PT | 27  6 |  | PT | 22  0 |  |
|  | PN | 0   2 |  | PN | 5   8 |  |

TT = True Tumor
TN = True Normal
PT = Predicted Tumor
PN = Predicted Normal
*All p values calculated by Fisher's Exact Test

FIG. 6

| | n | Median (%) | Range (%) | Mean (%) | Std Dev (%) | P for Difference |
|---|---|---|---|---|---|---|
| Tumors | 52 | 81.25 | 30 – 100 | 78.65 | 14.27 | <0.0001 |
| Normals | 47 | 20 | 0 – 80 | 27.02 | 20.76 | |
| Gleason 6 | 26 | 81.25 | 30 – 95 | 78.65 | 13.95 | 6 vs 7: 0.80 |
| Gleason 7 | 20 | 82.5 | 45 – 100 | 79.50 | 14.57 | 6 vs >7: 0.81 |
| Gleason >7 | 6 | 82.5 | 50 – 90 | 75.83 | 16.86 | 7 vs >7: 0.81 |
| Recurred (Tumors) | 8 | 82.5 | 45 – 90 | 77.50 | 16.48 | 0.77 |
| Did not Recur (Tumors) | 13 | 80 | 55 – 95 | 78.65 | 11.75 | |

FIG. 7A

| 1% Perm | Description |
|---|---|
| 608_at | Hs.169401 gnl|UG|Hs#S1860 Human apolipoprotein E mRNA, complete cds |
| 36659_at | Hs.75617 gnl|UG|Hs#S5971 Human mRNA for type IV collagen alpha (2) chain |
| 38750_at | Hs.8546 gnl|UG|Hs#S952721 Homo sapiens Notch3 (NOTCH3) mRNA, complete cds |
| 38111_at | Hs.81800 gnl|UG|Hs#S5591 H.sapiens mRNA for the chondroitin sulphate proteoglycan versican, V1 splice-variant; precursor peptide |
| 32305_at | Hs.179573 gnl|UG|Hs#S1908 Human collagen alpha-2 type I mRNA, complete cds, clone pHCOL2A1 |
| 1385_at | Hs.118787 gnl|UG|Hs#S3389 Human transforming growth factor-beta induced gene product (BIGH3) mRNA, complete cds |
| 40161_at | Hs.1584 gnl|UG|Hs#S2453 Human germline oligomeric matrix protein (COMP) mRNA, complete cds |
| 32488_at | Hs.119571 gnl|UG|Hs#S3950 Human mRNA for pro-alpha-1 type 3 collagen |
| 32761_at | Hs.197114 gnl|UG|Hs#S816221 Homo sapiens mRNA for KIAA0324 protein, partial cds |
| 897_at | Hs.75813 gnl|UG|Hs#S6082 Homo sapiens polycystic kidney disease 1 protein (PKD1) mRNA, complete cds |
| 37027_at | Hs.76549 gnl|UG|Hs#S5945 Human novel protein AHNAK mRNA, partial sequence |
| 38808_at | Hs.90107 gnl|UG|Hs#S669401 Human mRNA for Mr 110,000 antigen, complete cds |
| 34403_at | Hs.3745 gnl|UG|Hs#S417477 Human breast epithelial antigen BA46 mRNA, complete cds |
| 32562_at | Hs.76753 gnl|UG|Hs#S4651 H.sapiens end mRNA for endoglin |
| 33390_at | Hs.252889 gnl|UG|Hs#S572086 zx53d03.r1 Homo sapiens cDNA, 5' end |
| 1394_at | Hs.218403 gnl|UG|Hs#S268597 Homo sapiens oncomodulin gene |
| 39010_at | Hs.111680 gnl|UG|Hs#S1369068 tu06g05.x1 Homo sapiens cDNA, 3' end |

FIG. 9A

| | |
|---|---|
| 35832_at | Hs.70823 gnl|UG|Hs#S1569537 Homo sapiens mRNA for KIAA1077 protein, partial cds |
| 37311_at | Hs.77290 gnl|UG|Hs#S891943 untitled |
| 38379_at | Hs.82226 gnl|UG|Hs#S5148 H.sapiens NMB mRNA |
| 31719_at | Hs.118162 gnl|UG|Hs#S4692 Human mRNA for fibronectin (FN precursor) |
| 38077_at | Hs.80988 gnl|UG|Hs#S552863 H.sapiens RNA for type VI collagen alpha3 chain |
| 39420_at | Hs.129872 gnl|UG|Hs#S998699 Homo sapiens mRNA for KIAA0516 protein, partial cds |
| 32307_s_at | Hs.179573 gnl|UG|Hs#S5925 Human mRNA encoding Pro-alpha-2 chain of type I procollagen. (major part) |
| 31505_at | Hs.178551 gnl|UG|Hs#S5314 H.sapiens mRNA for ribosomal protein L8 |
| 41160_at | Hs.178728 gnl|UG|Hs#S1263645 Homo sapiens chromosome 19, cosmid R30538 |
| 39710_at | Hs.142827 gnl|UG|Hs#S226153 Human P311 HUM (3.1) mRNA, complete cds |
| 31610_at | Hs.271473 gnl|UG|Hs#S269375 Human DD96 mRNA, complete cds |
| 37294_at | Hs.77054 gnl|UG|Hs#S4498 Human BTG1 mRNA |
| 32610_at | Hs.79691 gnl|UG|Hs#S270491 H.sapiens mRNA for 37 kDa LIM domain protein |
| 31902_at | Hs.154424 gnl|UG|Hs#S1368273 Homo sapiens type 2 iodothyronine deiodinase mRNA, complete cds and 3'UTR |
| 36952_at | Hs.75860 gnl|UG|Hs#S5793 Homo sapiens mRNA for mitochondrial enoyl-CoA hydratase |
| 38418_at | Hs.82932 gnl|UG|Hs#S5259 Human PRAD1 mRNA for cyclin |
| 37628_at | Hs.82163 gnl|UG|Hs#S2823 Human monoamine oxidase B (MAOB) mRNA, complete cds |
| 1315_at | Hs.125078 gnl|UG|Hs#S569476 Human mRNA for ornithine decarboxylase antizyme, ORF 1 and ORF 2 |
| 38743_f_at | Hs.85181 gnl|UG|Hs#S552869 Human mRNA fragment for activated c-raf-1 (exons 8-17) |

FIG. 9B

| | |
|---|---|
| 35164_at | Hs.26077 gnl|UG|Hs#S1263452 Homo sapiens transmembrane protein (WFS1) mRNA, complete cds |
| 39397_at | Hs.1255 gnl|UG|Hs#S1871 Human apolipoprotein AI regulatory protein (ARP-1) mRNA, complete cds |
| 37713_at | Hs.79 gnl|UG|Hs#S157 Human aminoacylase-1 (ACY1) mRNA, complete cds |
| 38069_at | Hs.80768 gnl|UG|Hs#S552767 H.sapiens mRNA for CLC-7 chloride channel protein |
| 38794_at | Hs.89781 gnl|UG|Hs#S4896 Human mRNA for upstream binding factor (hUBF) |
| 36973_at | Hs.75916 gnl|UG|Hs#S305521 Human spliceosome associated protein (SAP 145) mRNA, complete cds |
| 32260_at | Hs.194673 gnl|UG|Hs#S5748 H.sapiens mRNA for major astrocytic phosphoprotein PEA-15 |
| 32529_at | Hs.74368 gnl|UG|Hs#S5189 H.sapiens p63 mRNA for transmembrane protein |
| 38465_at | Hs.83920 gnl|UG|Hs#S1390 Human peptidylglycine alpha-amidating monooxygenase mRNA, complete cds |
| 40923_at | Hs.18593 gnl|UG|Hs#S759069 zs45d07.r1 Homo sapiens cDNA, 5' end |
| 39738_at | Hs.146550 gnl|UG|Hs#S1972037 Human DNA sequence from clone RP1-68O2 on chromosome 22 Contains the 5' end of the APOL2 gene for apolipoprotein L 2, the APOL gene for apolipoprotein L, the MYH9 gene for nonmuscle type myosin heavy chain 9. ESTs, STSs and GS |
| 32378_at | Hs.198281 gnl|UG|Hs#S1608 Human TCB gene encoding cytosolic thyroid hormone-binding protein, complete cds |
| 38096_f_at | Hs.814 gnl|UG|Hs#S2942 Human MHC class II lymphocyte antigen (HLA-DP) beta chain mRNA, complete cds |
| 38642_at | Hs.10247 gnl|UG|Hs#S1055406 H.sapiens mRNA for MEMD protein |
| 36179_at | Hs.75074 gnl|UG|Hs#S637 Human MAP kinase activated protein kinase 2 mRNA, complete cds |
| 34091_s_at | Hs.2064 gnl|UG|Hs#S269781 H.sapiens vimentin gene |
| 32211_at | Hs.279554 gnl|UG|Hs#S1263112 Homo sapiens mRNA for 26S proteasome subunit p40.5, complete cds |

FIG. 9C

| | |
|---|---|
| 37043_at | Hs.76884 gnl\|UG\|Hs#S1090351 Homo sapiens DNA sequence from PAC 150O5 on chromosome 1p36.13-36.22. Contains the E2F2 gene for transcription factor E2F-2 and the ID3 gene for Inhibitor of DNA binding 3 (dominant negative helix-loop-helix protein, IR21, HEIR) |
| 39345_at | Hs.119529 gnl\|UG\|Hs#S1313803 PT1.3_06_D01.r Homo sapiens cDNA, 5' end |
| 1468_at | Hs.182366 gnl\|UG\|Hs#S3718 Human tumor necrosis factor type 1 receptor associated protein (TRAP1) mRNA, partial cds |

FIG. 9D

| 1% neg | Description |
|---|---|
| 272_at | Hs.1473 gnl\|UG\|Hs#S2260 Human gastrin-releasing peptide mRNA, complete cds |
| 31417_at | Hs.158348 gnl\|UG\|Hs#S998166 Homo sapiens prepro-orexin mRNA, complete cds |
| 494_at | Hs.845 gnl\|UG\|Hs#S553388 Human interleukin-13 (IL-13) precursor gene, complete cds |
| 35918_at | Hs.200188 gnl\|UG\|Hs#S1569242 Homo sapiens DLEC1 (deleted in lung and esophageal cancer 1; DLEC1 alias DLC1) mRNA, complete cds |
| 37779_at | Hs.123659 gnl\|UG\|Hs#S472863 H.sapiens mRNA for ASM-like phosphodiesterase 3b |
| 35403_at | Hs.161166 gnl\|UG\|Hs#S1569554 Homo sapiens mRNA for KIAA1094 protein, complete cds |
| 2075_s_at | Hs.180533 gnl\|UG\|Hs#S3607 Homo sapiens MAP kinase kinase 3 (MKK3) mRNA, complete cds |
| 38033_at | Hs.79844 gnl\|UG\|Hs#S1569753 Homo sapiens mRNA; cDNA DKFZp564M1416 (from clone DKFZp564M1416); partial cds |
| 32897_at | Hs.214142 gnl\|UG\|Hs#S1569683 Homo sapiens mRNA for methylenetetrahydrofolate reductase |
| 368_at | Hs.82128 gnl\|UG\|Hs#S269481 H.sapiens 5T4 gene for 5T4 Oncofetal antigen |
| 1903_at | Hs.79101 gnl\|UG\|Hs#S472624 H.sapiens mRNA for cyclin G1 |
| 32691_s_at | Hs.170917 gnl\|UG\|Hs#S705792 Human DNA for prostaglandin E receptor EP3 subtype |
| 37042_at | Hs.76873 gnl\|UG\|Hs#S376132 Homo sapiens lysosomal hyaluronidase (LUCA2) |

FIG. 9E

| | |
|---|---|
| 1547_at | Hs.99877 gnl|UG|Hs#S568 Human JAK family protein tyrosine kinase (JAK3) mRNA, complete cds |
| 230_s_at | Hs.36975 gnl|UG|Hs#S268600 Human follicle-stimulating hormone beta-subunit gene |
| 31685_at | Hs.234759 gnl|UG|Hs#S572501 H.sapiens mRNA for FEV protein |
| 41655_at | Hs.12256 gnl|UG|Hs#S1569601 Human DNA sequence from clone 191P20 on chromosome Xq23. Contains a pseudogene similar to Angiotensin |
| 605_at | Hs.194143 gnl|UG|Hs#S554446 Human BRCA1, Rho7 and vatI genes, complete cds, and ipf35 gene, partial cds |
| 41034_s_at | Hs.94581 gnl|UG|Hs#S592341 Homo sapiens hydroxysteroid sulfotransferase SULT2B1b (HSST2) mRNA, complete cds |
| 34588_i_at | Hs.46329 gnl|UG|Hs#S952882 Human Xp22 BAC CT-285I15 (from CalTech) |
| 970_r_at | Hs.77578 gnl|UG|Hs#S53771 H.sapiens mRNA for ubiquitin hydrolase |
| 35942_at | Hs.181202 gnl|UG|Hs#S1115452 qd24c11.x1 Homo sapiens cDNA, 3' end |
| 32560_s_at | Hs.76719 gnl|UG|Hs#S404009 zc65h10.r1 Homo sapiens cDNA, 5' end |
| 32287_s_at | Hs.258850 gnl|UG|Hs#S998433 Homo sapiens NKG2E gene |
| 33737_f_at | Hs.195484 gnl|UG|Hs#S1553151 wl81b11.x1 Homo sapiens cDNA, 3' end |
| 391_at | Hs.75180 gnl|UG|Hs#S5935 H.sapiens mRNA for protein phosphatase 5 |
| 1767_s_at | Hs.2025 gnl|UG|Hs#S553276 H.sapiens gene for transforming growth factor-beta 3 (TGF-beta 3) exon 1 (and joined CDS) |
| 37425_g_at | Hs.110746 gnl|UG|Hs#S1569431 Homo sapiens HCR (a-helix coiled-coil rod homologue) gene, complete cds |
| 32000_g_at | Hs.211562 gnl|UG|Hs#S1229327 qp09h03.x1 Homo sapiens cDNA, 3' end |
| 35200_at | Hs.2726 gnl|UG|Hs#S552774 H.sapiens mRNA for HMGI-C protein |

FIG. 9F

| | |
|---|---|
| 35283_at | Hs.5457 gnl|UG|Hs#S199382 yl76b12.s1 Homo sapiens cDNA, 3' end |
| 32492_g_at | Hs.121478 gnl|UG|Hs#S553535 Human dopamine D3 receptor (DRD3) gene, complete cds |
| 34648_at | Hs.250773 gnl|UG|Hs#S5442 H.sapiens mRNA for SSR alpha subunit |
| 33170_at | Hs.9059 gnl|UG|Hs#S1569337 Homo sapiens mRNA for KIAA0962 protein, partial cds |
| 33358_at | Hs.21894 gnl|UG|Hs#S514297 56b8 Homo sapiens cDNA |
| 41284_at | Hs.124029 gnl|UG|Hs#S1360802 wa02f11.x1 Homo sapiens cDNA, 3' end |
| 40565_at | Hs.169401 gnl|UG|Hs#S1240312 qy24a09.x1 Homo sapiens cDNA, 3' end |
| 37574_at | Hs.80261 gnl|UG|Hs#S377297 Homo sapiens enhancer of filamentation (HEF1) mRNA, complete cds |
| 37769_at | Hs.122575 gnl|UG|Hs#S952836 Homo sapiens G protein-coupled receptor Edg-4 mRNA, complete cds |
| 39402_at | Hs.126256 gnl|UG|Hs#S2699 Human interleukin 1-beta (IL1B) mRNA, complete cds |
| 39993_at | Hs.51 gnl|UG|Hs#S64 Homo sapiens mRNA for PIG-A protein, complete cds |
| 40513_at | Hs.278540 gnl|UG|Hs#S1999 Human calcineurin B mRNA, complete cds |
| 38012_at | Hs.79432 gnl|UG|Hs#S519 Human fibrillin-2 mRNA, complete cds |
| 35923_at | Hs.203 gnl|UG|Hs#S258 Human mRNA for brain cholecystokinin receptor |
| 1953_at | Hs.37501 gnl|UG|Hs#S952783 untitled |
| 2082_s_at | Hs.194657 gnl|UG|Hs#S3453 Human uvomorulin (E-cadherin) (UVO) mRNA, complete cds |
| 543_g_at | Hs.7678 gnl|UG|Hs#S553854 cellular retinoic acid-binding protein [human, skin, mRNA, 735 nt] |
| 39986_at | Hs.49378 gnl|UG|Hs#S1569790 Homo sapiens mRNA; cDNA DKFZp586D0919 (from clone DKFZp586D0919); partial cds |
| 33085_at | Hs.158297 gnl|UG|Hs#S705828 Human hPD-1 (hPD-1) mRNA, complete cds |
| 38317_at | Hs.95243 gnl|UG|Hs#S3145 Homo sapiens (pp21) mRNA, complete cds |

FIG. 9G

| | |
|---|---|
| 648_at | Hs.1372 gnl\|UG\|Hs#S4182 Homo sapiens vasopressin V3 receptor mRNA, complete cds |
| 35208_at | Hs.27973 gnl\|UG\|Hs#S1367634 Homo sapiens mRNA for KIAA0874 protein, partial cds |
| 34529_at | Hs.12513 gnl\|UG\|Hs#S1564617 wq32c11.x1 Homo sapiens cDNA, 3' end |
| 1506_at | Hs.84 gnl\|UG\|Hs#S102 Human mRNA for interleukin 2 receptor gamma chain |
| 38851_at | Hs.272951 gnl\|UG\|Hs#S569344 Human endogenous retrovirus envelope region mRNA (PL1) |
| 881_at | Hs.123125 gnl\|UG\|Hs#S1189 Human integrin B-6 mRNA, complete cds |
| 33947_at | Hs.66542 gnl\|UG\|Hs#S269788 Human GPR3 G protein-coupled receptor gene, complete cds |
| 40553_at | Hs.166361 gnl\|UG\|Hs#S1431459 wg38g10.x1 Homo sapiens cDNA, 3' end |
| 40527_at | Hs.156115 gnl\|UG\|Hs#S876339 Homo sapiens kidney and cardiac voltage dependent K+ channel (KvLQT1) mRNA, complete cds |
| 32788_at | Hs.199179 gnl\|UG\|Hs#S270018 Human mRNA for RanBP2 (Ran-binding protein 2), complete cds |
| 33459_at | Hs.24103 gnl\|UG\|Hs#S998337 Human Chromosome 16 BAC clone CIT987SK-A-363E6 |
| 33472_at | Hs.2664 gnl\|UG\|Hs#S4700 H.sapiens mRNA for flavin-containing monooxygenase 4 |
| 882_s_at | Hs.173894 gnl\|UG\|Hs#S2018 Human macrophage-specific colony-stimulating factor (CSF-1) mRNA, complete cds |
| 41274_at | Hs.23294 gnl\|UG\|Hs#S1031510 ol10d03.s1 Homo sapiens cDNA, 3' end |
| 36742_at | Hs.274295 gnl\|UG\|Hs#S1368570 Human putative zinc finger protein (ZNFB7) mRNA, complete cds |
| 34832_s_at | Hs.4764 gnl\|UG\|Hs#S1263822 Homo sapiens mRNA for KIAA0763 protein, complete cds |
| 38191_at | Hs.155987 gnl\|UG\|Hs#S1057819 ox42d12.s1 Homo sapiens cDNA, 3' end |
| 35692_at | Hs.35861 gnl\|UG\|Hs#S1570341 Homo sapiens mRNA; cDNA DKFZp586E1621 (from clone DKFZp586E1621) |

FIG. 9H

| | |
|---|---|
| 199_s_at | Hs.69171 gnl|UG|Hs#S226292 Human lipid-activated, protein kinase PRK2 mRNA, complete cds |
| 1177_at | Hs.80343 gnl|UG|Hs#S417593 Human MT2-MMP gene for matrix metalloprotein, complete cds |
| 37266_at | Hs.78765 gnl|UG|Hs#S472921 Human zinc finger protein mRNA, complete cds |
| 34618_at | Hs.69351 gnl|UG|Hs#S3557 Homo sapiens indian hedgehog protein (IHH) mRNA, 5' end |
| 33954_at | Hs.66774 gnl|UG|Hs#S472964 Human zinc finger protein zfp47 (zf47) mRNA, partial cds |
| 2005_s_at | Hs.99877 gnl|UG|Hs#S270085 Human JAK family tyrosine protein kinase splice variant (hJak3S) mRNA, partial cds |
| 307_at | Hs.89499 gnl|UG|Hs#S1243 Human lipoxygenase mRNA, complete cds |
| 41056_at | Hs.96744 gnl|UG|Hs#S1570002 Homo sapiens mRNA; cDNA DKFZp586D0823 (from clone DKFZp586D0823); partial cds |
| 38607_at | Hs.184194 gnl|UG|Hs#S891863 Homo sapiens putative tetraspan transmembrane protein L6H (TM4SF5) mRNA, complete cds |
| 41276_at | Hs.23964 gnl|UG|Hs#S512959 37d11 Homo sapiens cDNA |
| 1223_at | Hs.2994 gnl|UG|Hs#S5452 H.sapiens mRNA PCTAIRE-3 for serine |
| 34722_at | Hs.6441 gnl|UG|Hs#S472999 Human tissue inhibitor of metalloproteinases-2 (TIMP-2) gene |
| 38788_at | Hs.89633 gnl|UG|Hs#S5110 H.sapiens Myl (PML) mRNA |
| 36557_at | Hs.635 gnl|UG|Hs#S860 Human voltage-dependent calcium channel beta-1 subunit mRNA, complete cds |
| 38691_s_at | Hs.1074 gnl|UG|Hs#S268815 Human pulmonary surfactant protein (SP5) mRNA, complete cds |
| 35598_at | Hs.143522 gnl|UG|Hs#S1049908 ol26b03.s1 Homo sapiens cDNA, 3' end |
| 31379_at | Hs.137570 gnl|UG|Hs#S1090500 Homo sapiens HSFF-1 mRNA, partial cds |
| 34150_at | Hs.227473 gnl|UG|Hs#S1569581 Homo sapiens hGnT-IV-H mRNA for alpha-1,3-D-mannoside beta-1,4-N-acetylglucosaminyltransferase IV-homologue, complete cds |

FIG. 9I

| | |
|---|---|
| 34538_at | Hs.23777 gnl\|UG\|Hs#S1570557 Homo sapiens mRNA full length insert cDNA clone EUROIMAGE 35394 |
| 40594_r_at | Hs.172670 gnl\|UG\|Hs#S4405 H.sapiens ALK-1 mRNA |
| 36359_at | Hs.158029 gnl\|UG\|Hs#S1458 Human testis-specific protein kinase gamma-subunit mRNA, complete cds |
| 1988_at | Hs.166074 gnl\|UG\|Hs#S569460 H.sapiens mRNA for platelet derived growth factor alpha receptor |
| 35187_at | Hs.26837 gnl\|UG\|Hs#S1570331 Homo sapiens mRNA; cDNA DKFZp586K1123 (from clone DKFZp586K1123) |
| 35227_at | Hs.29287 gnl\|UG\|Hs#S554538 Homo sapiens CtBP interacting protein CtIP (CtIP) mRNA, complete cds |
| 1492_f_at | Hs.250615 gnl\|UG\|Hs#S2037 Human cytochrome P450IIA4 (CYP2A4) mRNA, complete cds |
| 32716_at | Hs.172690 gnl\|UG\|Hs#S4620 H.sapiens mRNA for diacylglycerol kinase |
| 41183_at | Hs.180034 gnl\|UG\|Hs#S3496 Human cleavage stimulation factor 77kDa subunit mRNA, complete cds |
| 40253_at | Hs.154846 gnl\|UG\|Hs#S1263299 Homo sapiens mRNA for phosphatidylinositol 4-kinase (NPIK-C) |
| 31694_at | Hs.239459 gnl\|UG\|Hs#S472987 H.sapiens Na+-D-glucose cotransport regulator gene |
| 40534_at | Hs.158112 gnl\|UG\|Hs#S964605 ak01e07.s1 Homo sapiens cDNA, 3' end |
| 1754_at | Hs.180224 gnl\|UG\|Hs#S816382 Homo sapiens Fas-binding protein (DAXX) mRNA, partial cds |
| 34809_at | Hs.4278 gnl\|UG\|Hs#S267482 yq87g03.r1 Homo sapiens cDNA, 5' end |
| 34788_at | Hs.4105 gnl\|UG\|Hs#S1368155 Homo sapiens mRNA; cDNA DKFZp586A0618 (from clone DKFZp586A0618) |
| 998_s_at | Hs.25333 gnl\|UG\|Hs#S4967 H.sapiens IL-1R2 mRNA for type II interleukin-1 receptor, (cell line CB23) |
| 37757_at | Hs.79353 gnl\|UG\|Hs#S2560 Homo sapiens E2F-related transcription factor (DP-1) mRNA, complete cds |
| 2060_at | Hs.79241 gnl\|UG\|Hs#S1889 Human B-cell leukemia |
| 38254_at | Hs.90419 gnl\|UG\|Hs#S1367642 Homo sapiens mRNA for KIAA0882 protein, partial cds |

FIG. 9J

| | |
|---|---|
| 32234_at | Hs.19261 gnl|UG|Hs#S876061 Homo sapiens torsinA (DYT1) mRNA, complete cds |
| 594_s_at | Hs.155140 gnl|UG|Hs#S759 Human casein kinase II alpha subunit mRNA, complete cds |
| 988_at | Hs.50964 gnl|UG|Hs#S5516 Human mRNA for transmembrane carcinoembryonic antigen BGPa (formerly TM1-CEA) |
| 39301_at | Hs.40300 gnl|UG|Hs#S4176 H.sapiens mRNA for skeletal muscle-specific calpain |
| 35505_at | Hs.123090 gnl|UG|Hs#S1200072 qm12b10.x1 Homo sapiens cDNA, 3' end |
| 41387_r_at | Hs.103915 gnl|UG|Hs#S816459 Human mRNA for KIAA0346 gene, partial cds |
| 38315_at | Hs.95197 gnl|UG|Hs#S1264095 Homo sapiens mRNA for RALDH2-T, complete cds |
| 33436_at | Hs.2316 gnl|UG|Hs#S4005 Homo sapiens SOX9 mRNA |
| 33370_r_at | Hs.239926 gnl|UG|Hs#S417592 Human methyl sterol oxidase (ERG25) mRNA, complete cds |
| 36696_at | Hs.248059 gnl|UG|Hs#S891697 Homo sapiens PIGCP1 pseudogene |
| 41569_at | Hs.44131 gnl|UG|Hs#S1398200 tx40a08.x1 Homo sapiens cDNA, 3' end |
| 36462_at | Hs.54413 gnl|UG|Hs#S376210 Human retinoic acid-responsive protein (NN8-4AG) mRNA, complete cds |
| 39923_at | Hs.13531 gnl|UG|Hs#S1535519 wo84c08.x1 Homo sapiens cDNA, 3' end |
| 32464_at | Hs.105924 gnl|UG|Hs#S1263547 Homo sapiens beta defensin 2 (HBD2) gene, complete cds |
| 36195_at | Hs.250616 gnl|UG|Hs#S3715 Human NAD(H)-specific isocitrate dehydrogenase alpha subunit precursor mRNA, complete cds |
| 874_at | Hs.340 gnl|UG|Hs#S2326 Human interferon gamma treatment inducible mRNA |
| 32971_at | Hs.77889 gnl|UG|Hs#S3473 Human X123 mRNA, 3' end |
| 887_at | Hs.92614 gnl|UG|Hs#SS52087 Human growth |
| 35737_at | Hs.236774 gnl|UG|Hs#S705592 Human non-histone chromosomal protein (NHC) mRNA, complete cds |

FIG. 9K

| | |
|---|---|
| 39626_s_at | Hs.2860 gnl|UG|Hs#S5173 H.sapiens OTF3 mRNA encoding octamer binding protein 3A |
| 260_at | Hs.75438 gnl|UG|Hs#S2079 Human dihydropteridine reductase (hDHPR) mRNA, complete cds |
| 250_at | Hs.172674 gnl|UG|Hs#S4253 Homo sapiens NF-AT4c mRNA, complete cds |
| 31792_at | Hs.1378 gnl|UG|Hs#S2781 Human lipocortin-III mRNA, complete cds |
| 226_at | Hs.183037 gnl|UG|Hs#S1949 Human cAMP-dependent protein kinase type I-alpha subunit (PRKAR1A) mRNA, complete cds |
| 41167_at | Hs.179574 gnl|UG|Hs#S1463 Human protein phosphatase 2A alpha subunit mRNA, complete cds |
| 38226_at | Hs.5105 gnl|UG|Hs#S511975 23h11 Homo sapiens cDNA |
| 32149_at | Hs.183752 gnl|UG|Hs#S799747 nj54a10.s1 Homo sapiens cDNA |
| 40153_at | Hs.158164 gnl|UG|Hs#S269747 H.sapiens RING4 cDNA |
| 40501_s_at | Hs.169849 gnl|UG|Hs#S5425 H.sapiens mRNA for slow MyBP-C |

FIG. 9L

| 0.1% Perm | Description |
|---|---|
| 32306_g_at | Collagen alpha-2 type I (Hs.179573) |
| 33900_at | Follistatin-related protein FLRG (FLRG) (Hs.25348) |
| 1933_g_at | Multidrug resistance-associated protein homolog (MRP3) (Hs.90786) |
| 39069_at | Aortic carboxypeptidase-like protein ACLP (Hs.118397) |
| 37319_at | Insulin-like growth factor-binding protein-3 gene (Hs.77326) |
| 41428_at | ABC transporter MOAT-C (MOAT-C) (Hs.108660) |
| 659_g_at | Thrombospondin 2 (THBS2) (Hs.108623) |
| 39098_at | Dermal fibroblast elastin (Hs.203917) |
| 35852_at | KIAA0658 protein (Hs.7278)(Cryptochrome 2 (photolyase-like)) |
| 39066_at | Microfibril-associated glycoprotein 4 (MFAP4) (Ferritin, light chain) (Hs. 118223) |
| 33232_at | Cysteine-rich protein 1 (intestinal) (Hs. 17409; ou23f10.x1) |
| 671_at | SPARC (Hs.111779) |
| 39038_at | UP50 mRNA, complete cds (Fibrulin 5)(Hs.11494) |
| 38126_at | Biglycan (Hs.821) |
| 1842_at | XP-C repair complementing protein (p58)(RAD23 (S. cerevisiae) homolog B) (Hs. 178658) |

FIG. 10A

| 0.10% | Description |
|---|---|
| 35626_at | N-sulphoglucosamine sulphohydrolase (Hs.31074) |
| 38983_at | NADH dehydrogenase (ubiquinone) 1 alpha subcomplex, 6 (14kD, B14)(Hs.274416; qg70a09.x1) |
| 37026_at | Kruppel-like zinc finger protein Zf9 (Hs.4055 )(Chromosome 21 open reading frame 50) |
| 40735_at | Histidase (Histidine ammonia-lyase) |
| 1924_at | Cyclin H (Hs.514) |
| 40445_at | Ets-related transcription factor (ERT) (Hs.166096) (E74-like factor 3 (ets domain transcription factor, epithelial-specific )) |
| 1647_at | RasGAP-related protein (IQGAP2) (IQ motif containing GTPase activating protein 2) (Hs.78993) |
| 40252_g_at | clone A9A2BRB2 (CAC)n (HIV-1 rev binding protein 2)(Hs.154762) |
| 33374_at | Complement component 2 (C2) gene allele b (Hs.2253) |
| 36731_g_at | cDNA (DKFZp434L0827 30% homology to MOATs)(Hs.55879) |
| 35413_s_at | Zinc finger protein 22 (KOX 15)(Hs.166051; zs30g01.r1) |
| 37690_at | Acetolactate synthase homolog (Hs.78880 ) (ilvB (bacterial acetolactate synthase)-like) |
| 36160_s_at | Protein tyrosine phosphatase receptor pi (PTPRP) (Hs.74624) |
| 37572_at | Cholecystokinin (Hs.80247; wy80b07.x1) |

FIG. 10B

Chromogranin A

Platelet-derived growth factor receptor, beta

Homeodomain-containing protein (HOXC6)

Inositol 1,4,5-trisphosphate receptor, type 3

Beta-galactoside alpha-2,6-sialyltransferase

| Unigene Accession | Title | ProbeSet_ID |
|---|---|---|
| Hs.288869 | Nuclear receptor subfamily 2, group F, member 2 | 215073_s_at |
| Hs.75248 | topoisomerase (DNA) II beta (180kD) | 211987_at |
| Hs.288031 | thymosin, beta 4-like | 216438_s_at |
| Hs.108623 | thrombospondin 2 | 203083_at |
| Hs.1650 | solute carrier family 26, member 3 | 206143_at |
| Hs.287820 | Similar to Fibronectin | 216442_x_at |
| Hs.111779 | secreted protein, acidic, cysteine-rich (osteonectin) | 200665_s_at |
| Hs.178551 | ribosomal protein L8 | 200936_at |
| Hs.182825 | ribosomal protein L35 | 200002_at |
| Hs.7252 | retinoic acid induced 17 | 212124_at |
| Hs.75447 | ralA binding protein 1 | 202845_s_at |
| Hs.31130 | putative sterol reductase SR-1 | 210130_s_at |
| Hs.172182 | poly(A)-binding protein, cytoplasmic 1 | 215157_x_at |
| Hs.306965 | poly(A) binding protein, cytoplasmic 3 | 208113_x_at |
| Hs.83920 | peptidylglycine alpha-amidating monooxygenase | 202336_s_at |
| Hs.83920 | peptidylglycine alpha-amidating monooxygenase | 212958_x_at |
| Hs.76144 | PDGFRbeta | 202273_at |
| Hs.76144 | PDGFRbeta | 202273_at |
| Hs.142827 | P311 protein | 201310_s_at |
| Hs.302649 | nucleosome assembly protein 1-like 1 | 213864_s_at |
| Hs.302649 | nucleosome assembly protein 1-like 1 | 204528_s_at |
| Hs.347991 | nuclear receptor subfamily 2, group F, member 2 | 209120_at |
| Hs.29131 | nuclear receptor coactivator 2 (GRIP1) | 212867_at |
| Hs.8546 | Notch homolog 3 (Drosophila) | 203238_s_at |
| Hs.75283 | nexin 1 | 214531_s_at |
| Hs.6909 | monooxygenase X | 209708_at |
| Hs.82045 | midkine (neurite growth-promoting factor 2) | 209035_at |
| Hs.82045 | midkine (neurite growth-promoting factor 2) | 209035_at |
| Hs.83337 | latent transforming growth factor beta binding protein 2 | 204682_at |
| Hs.70823 | KIAA1077 protein | 212353_at |
| Hs.119206 | insulin-like growth factor binding protein 7 | 201163_s_at |
| Hs.119206 | insulin-like growth factor binding protein 7 | 201162_at |
| Hs.77326 | insulin-like growth factor binding protein 3 | 210095_s_at |
| Hs.76884 | inhibitor of DNA binding 3, dominant negative helix-loop-helix protein | 207826_s_at |
| Hs.268371 | hypothetical protein FLJ20274 | 206555_s_at |
| Hs.820 | homeo box C6 | 206858_s_at |

FIG. 14A

| Unigene_Accession | Title | ProbeSet_ID |
|---|---|---|
| Hs.82226 | glycoprotein (transmembrane) nmb | 201141_at |
| Hs.334695 | GATA binding protein 2 | 209710_at |
| Hs.287820 | fibronectin 1 | 212464_s_at |
| Hs.58189 | eukaryotic translation initiation factor 3, subunit 3 (gamma, 40kD) | 201592_at |
| Hs.2642 | eukaryotic translation elongation factor 1 alpha 2 | 204540_at |
| Hs.243901 | EST | 212250_at |
| Hs.18593 | EST | 213119_at |
| Hs.111680 | endosulfine alpha | 202596_at |
| Hs.76753 | endoglin (Osler-Rendu-Weber syndrome 1) | 201809_s_at |
| Hs.184693 | elongin C | 202824_s_at |
| Hs.9295 | elastin (supravalvular aortic stenosis, Williams-Beuren syndrome) | 212670_at |
| Hs.9295 | elastin (supravalvular aortic stenosis, Williams-Beuren syndrome) | 212670_at |
| Hs.351875 | cytochrome c oxidase subunit VIc | 201754_at |
| Hs.70327 | cysteine-rich protein 2 | 208978_at |
| Hs.17409 | cysteine-rich protein 1 (intestinal) | 205081_at |
| Hs.344027 | collagen, type III, alpha 1 | 211161_s_at |
| Hs.179573 | collagen, type I, alpha 2 | 202404_s_at |
| Hs.179573 | collagen, type I, alpha 2 | 202404_s_at |
| Hs.179573 | collagen, type I, alpha 2 | 202403_s_at |
| Hs.81800 | chondroitin sulfate proteoglycan 2 (versican) | 221731_x_at |
| Hs.81800 | chondroitin sulfate proteoglycan 2 (versican) | 204620_s_at |
| Hs.1584 | cartilage oligomeric matrix protein (pseudoachondroplasia, epiphyseal dysplasia 1, multiple) | 205713_s_at |
| Hs.1584 | cartilage oligomeric matrix protein (pseudoachondroplasia, epiphyseal dysplasia 1, multiple) | 205713_s_at |
| Hs.77054 | B-cell translocation gene 1, anti-proliferative | 200921_s_at |
| Hs.108660 | ATP-binding cassette, sub-family C (CFTR/MRP), member 5 | 209380_s_at |
| Hs.108660 | ATP-binding cassette, sub-family C (CFTR/MRP), member 5 | 209380_s_at |
| Hs.169401 | apolipoprotein E | 203382_s_at |
| Hs.268571 | apolipoprotein C-I | 204416_x_at |
| Hs.118397 | AE binding protein 1 | 201792_at |
| Hs.72157 | adlican | 209596_at |
| Hs.111222 | ribosomal protein L30 | 200062_s_at |

FIG. 14B

| Unigene_Accession | Title | ProbeSet_ID |
|---|---|---|
| Hs.77183 | v-raf murine sarcoma 3611 viral oncogene homolog 1 | 201895_at |
| Hs.77183 | v-raf murine sarcoma 3611 viral oncogene homolog 1 | 201895_at |
| Hs.23582 | tumor-associated calcium signal transducer 2 | 202286_s_at |
| Hs.14894 | trans-golgi network protein 2 | 203834_s_at |
| Hs.2025 | transforming growth factor, beta 3 | 209747_at |
| Hs.158287 | syndecan 3 (N-syndecan) | 202898_at |
| Hs.2316 | SRY (sex determining region Y)-box 9 (campomelic dysplasia, autosomal sex-reversal) | 202936_s_at |
| Hs.2554 | sialyltransferase 1 (beta-galactoside alpha-2,6-sialyltransferase) | 201998_at |
| Hs.138860 | Rho GTPase activating protein 1 | 202117_at |
| Hs.26550 | retinoid X receptor, gamma | 205954_at |
| Hs.35861 | Ras-induced senescence 1 | 213338_at |
| Hs.74624 | protein tyrosine phosphatase, receptor type, N polypeptide 2 | 203029_s_at |
| Hs.152978 | proteasome (prosome, macropain) activator subunit 3 (PA28 gamma; Ki) | 200988_s_at |
| Hs.96744 | prostate androgen-regulated transcript 1 | 205834_s_at |
| Hs.2860 | POU domain, class 5, transcription factor 1 | 208286_x_at |
| Hs.117780 | potassium voltage-gated channel, delayed-rectifier, subfamily S, member 1 | 207366_at |
| Hs.93841 | potassium large conductance calcium-activated channel, subfamily M, beta member 1 | 209948_at |
| Hs.31074 | N-sulfoglucosamine sulfohydrolase (sulfamidase) | 204293_at |
| Hs.5025 | nebulette | 203961_at |
| Hs.78344 | myosin, heavy polypeptide 11, smooth muscle | 201496_x_at |
| Hs.183752 | microseminoprotein, beta- | 210297_s_at |
| Hs.183752 | microseminoprotein, beta- | 207430_s_at |
| Hs.283655 | lysophospholipase II | 215568_x_at |
| Hs.93199 | lanosterol synthase (2,3-oxidosqualene-lanosterol cyclase) | 202245_at |
| Hs.177664 | KIAA0914 gene product | 202973_x_at |
| Hs.103915 | KIAA0346 protein | 213146_at |
| Hs.89868 | KIAA0062 protein | 212110_at |
| Hs.171995 | kallikrein 3, (prostate specific antigen) | 204582_s_at |
| Hs.171995 | kallikrein 3, (prostate specific antigen) | 204582_s_at |
| Hs.171995 | kallikrein 3, (prostate specific antigen) | 204582_s_at |
| Hs.190913 | JNK1 beta1 protein kinase | 210671_x_at |
| Hs.250616 | isocitrate dehydrogenase 3 (NAD+) alpha | 202070_s_at |
| Hs.82112 | interleukin 1 receptor, type I | 202948_at |
| Hs.78877 | inositol 1,4,5-trisphosphate 3-kinase B | 203723_at |
| Hs.22111 | immunoglobulin superfamily, member 1 | 207695_s_at |
| Hs.3268 | heat shock 70kD protein 6 (HSP70B') | 213418_at |

FIG. 14C

| Unigene_Accession | Title | ProbeSet_ID |
|---|---|---|
| Hs.115352 | growth hormone 1 | 205840_x_at |
| Hs.155546 | golgi associated, gamma adaptin ear containing, ARF binding protein 2 | 208914_at |
| Hs.306122 | glycoprotein, synaptic 2 | 208336_s_at |
| Hs.343871 | glycophorin B (includes Ss blood group) | 207459_x_at |
| Hs.336920 | glutathione peroxidase 3 (plasma) | 201348_at |
| Hs.2704 | glutathione peroxidase 2 (gastrointestinal) | 202831_at |
| Hs.77889 | Friedreich ataxia region gene X123 | 213900_at |
| Hs.183738 | FERM, RhoGEF (ARHGEF) and pleckstrin domain protein 1 (chondrocyte-derived) | 201910_at |
| Hs.159543 | endothelial differentiation, G-protein-coupled receptor 6 | 206437_at |
| Hs.166096 | E74-like factor 3 (ets domain transcription factor, epithelial-specific ) | 201510_at |
| Hs.103854 | docking protein 1, 62kD (downstream of tyrosine kinase 1) | 216835_s_at |
| Hs.2253 | complement component 2 | 203052_at |
| Hs.173894 | colony stimulating factor 1 (macrophage) | 209716_at |
| Hs.164410 | chromosome 16 open reading frame 7 | 205781_at |
| Hs.80247 | cholecystokinin | 205827_at |
| Hs.76722 | CCAAT/enhancer binding protein (C/EBP), delta | 203973_s_at |
| Hs.12 | carcinoembryonic antigen-related cell adhesion molecule 4 | 207205_at |
| Hs.50964 | carcinoembryonic antigen-related cell adhesion molecule 1 (biliary glycoprotein) | 209498_at |
| Hs.287921 | cAMP responsive element binding protein 3 (luman) | 209432_s_at |
| Hs.75462 | BTG family, member 2 | 201236_s_at |
| Hs.193163 | bridging integrator 1 | 202931_x_at |
| Hs.193163 | bridging integrator 1 | 214439_x_at |
| Hs.31210 | B-cell CLL/lymphoma 3 | 204908_s_at |
| Hs.176658 | aquaporin 8 | 206784_at |
| Hs.75741 | amiloride binding protein 1 (amine oxidase (copper-containing)) | 203559_s_at |
| Hs.95197 | aldehyde dehydrogenase 1 family, member A2 | 207016_s_at |
| Hs.154721 | aconitase 1, soluble | 207071_s_at |
| Hs.1852 | acid phosphatase, prostate | 204393_s_at |
| Hs.194750 | Interleukin 2 Receptor, Beta (IL-2 Receptor, CD122 anti | 214955_at |
| Hs.419 | distal-less homeo box 2 | 215685_s_at |
| Hs.158029 | protein kinase, cAMP-dependent, catalytic, gamma (PRKACG | 207228_at |
| Hs.323053 | EST | 213658_at |
| Hs.323053 | EST | 213657_s_at |
| Hs.323053 | EST | 213658_at |
| Hs.323053 | EST | 213657_s_at |
| Hs.128425 | Similar to cactin | 214892_x_at |

FIG. 14D

| Unigene_Accession | Title | ProbeSet_ID |
|---|---|---|
| Hs.166079 | cyp related pseudogene | 214235_at |
| Hs.166079 | cyp related pseudogene | 214234_s_at |
| Hs.301373 | ubiquitin specific protease 19 | 214674_at |
| Hs.117729 | keratin 14 | 209351_at |
| Hs.289106 | Ewing sarcoma breakpoint region 1 protein | 213779_at |
| Hs.169849 | myosin-binding protein C, slow-type | 214087_s_at |
| Hs.239 | forkhead box M1 | 214148_at |
| Hs.2780 | jun D proto-oncogene | 214326_x_at |
| Hs.336920 | glutathione peroxidase 3 (plasma) | 214091_s_at |

FIG. 14E

PROSTATE CANCER DIAGNOSIS AND OUTCOME PREDICTION BY EXPRESSION ANALYSIS

RELATED APPLICATION

This application claims the benefit of U.S. Provisional Application No. 60/343,448, filed Dec. 21, 2001. The entire teachings of the above application are incorporated herein by reference.

GOVERNMENT SUPPORT

The invention was supported, in whole or in part, by a grant NIH 1U01CA84995 from the National Institutes of Health. The Government has certain rights in the invention.

BACKGROUND OF THE INVENTION

Classification of biological samples from individuals is not an exact science. In many instances, accurate diagnosis and safe and effective treatment of a disorder depend on being able to discern biological distinctions among cell or tissue samples from a particular area of the body, such as prostate cancer samples and normal prostate samples. The classification of a sample from an individual into particular disease classes has often proven to be difficult, incorrect, or equivocal. Typically, using traditional methods, such as histochemical analyses, immunophenotyping, and cytogenetic analyses, only one or two characteristics of the sample are analyzed to determine the sample's classification. Inaccurate results can lead to incorrect diagnoses and potentially ineffective or harmful treatment.

Prostate cancer (CaP) is the most common non-dermatological cancer in the United States with an estimated 198,100 new cases and 31,500 deaths in 2001. The widespread adoption of screening based upon the serum prostate specific antigen (PSA) level has led to the earlier detection of prostate cancer, with most cases appearing confined to the prostate gland at presentation. While such early diagnosis provides an opportunity to cure men with organ-confined disease, up to 30% of men undergoing radical prostatectomy as primary therapy for such tumors will ultimately relapse, presumably as a result of micro-metastatic disease present at the time of surgery. A critical issue in the care of men with prostate cancer is to improve the risk stratification of patients with intermediate risk disease. Clinical stage, Gleason score, and the serum PSA remain the most important variables with which to predict disease behavior. However, while these measures can successfully distinguish between men at low, intermediate, and high risk for tumor recurrence following local therapy, they are less successful in helping guide therapy for the majority of men falling into the intermediate risk group. Thus, a need exists for accurate and efficient methods for identifying prostate cancer and determining prostate cancer outcomes.

SUMMARY OF THE INVENTION

The present invention features methods of identifying prostate cancer, methods for prognosing and diagnosing prostate cancer, methods for identifying a compound that modulates prostate cancer development, methods for determining the efficacy of a prostate cancer therapy, and oligonucleotide microarrays containing probes for genes involved in prostate cancer development.

The present invention relates to one or more sets of informative genes whose expression correlates with a distinction between samples. In a particular embodiment, the distinction is a distinction between the presence or absence of prostate cancer in a patient from which the sample was obtained. In another embodiment the distinction is treatment outcome, survival, or efficacy of treatment.

When classifying a sample as to the presence or absence of prostate cancer in the patient from which the sample was obtained, expression of prostate cancer identification informative genes (i.e., genes having increased expression in prostate cancer compared to normal prostate, or having decreased expression in prostate cancer compared to normal prostate) is determined. Such prostate cancer identification informative genes can be, for example, all or a subset of the genes shown in FIGS. 2A–2N and FIGS. 3A—3C2. FIGS. 2A–2N show informative genes whose expression is decreased in prostate cancer compared to normal prostate. FIGS. 3A–3C2 show informative genes whose expression is increased in prostate cancer compared to normal prostate.

When classifying a sample into a prostate cancer treatment outcome class, prognosis or diagnosis category, informative genes can be, for example, prostate cancer identification informative genes, for example, all or a subset of the shown in FIGS. 2A–2N (having decreased expression in prostate cancer compared to normal prostate tissue) and FIGS. 3A–3C2 (having increased expression in prostate cancer compared to normal prostate tissue), prostate cancer differentiation informative genes (genes having increased expression in prostate cancers having a Gleason score of 6 or greater, or genes having decreased expression in prostate cancers having a Gleason score of 6 or greater, compared to appropriate controls), for example, all or a subset of the genes shown in FIGS. 9A–9D, FIG. 10A, and FIGS. 14A–14B (having increased expression in prostate cancers having a Gleason score of 6 or greater, compared to appropriate controls) and FIGS. 9E–9L, FIG. 10B, and FIGS. 14C–14E (having decreased expression in prostate cancers having a Gleason score of 6 or greater, compared to appropriate controls), and tumor recurrence informative genes (genes showing increased expression in recurrent prostate tumors compared to appropriate controls, or genes showing decreased expression in recurrent prostate tumors compared to appropriate controls), for example, all or a subset of Platelet Derived Growth Factor Receptor, Beta Chromogranin A, and HOXC6 (all of which show increased expression in recurrent prostate tumors compared to appropriate controls) and Inositol Triphosphate Receptor Type 3 and Beta Galactoside Sialotransferase (all of which show decreased expression in recurprostate tumors compared to appropriate controls). When classifying a sample based on treatment outcome (e.g., recurrence), preferably the informative genes include at least one gene selected from the group consisting of Platelet Derived Growth Factor Receptor, Beta Chromogranin A, HOXC6, Inositol Triphosphate Receptor Type 3, and Beta Galactoside Sialotransferase.

The invention relates to methods of diagnosing or predicting the likelihood of prostate cancer development in a patient comprising the steps of isolating a gene expression product from at least one informative gene (for example, selected from prostate cancer identification informative genes, prostate cancer differentiation informative genes, and tumor recurrence informative genes) from a sample, for example, from one or more cells; and determining a gene expression profile of at least one informative gene, wherein the gene expression profile is correlated with the presence or absence of prostate cancer or an increased or decreased likelihood of developing prostate cancer.

In one embodiment of the methods of the present invention, the gene expression product is mRNA, and in a particular embodiment, the gene expression profile is determined utilizing specific hybridization probes. In particular, the gene expression profile is determined utilizing oligonucleotide microarrays, such as those on which probes or primers for all or a subset of the informative genes disclosed herein are immobilized. In another embodiment of the invention, the gene expression product is a peptide, and in a particular embodiment, the gene expression profile is determined utilizing antibodies. In another embodiment, the informative genes are genes having increased expression in prostate cancer and are selected from the group consisting of the genes in FIGS. 3A–3C2, FIGS. 9A–9D, FIG. 10A, FIGS. 14A–14B, Platelet Derived Growth Factor Receptor, Beta Chromogranin A, and HOXC6. In another embodiment, the informative genes are genes having decreased expression in prostate cancer and are selected from the group consisting of the genes in FIGS. 2A–N, FIGS. 9E–9L, FIG. 10B, FIGS. 14C–14E, Inositol Triphosphate Receptor Type 3, and Beta Galactoside Sialotransferase.

The invention further relates to a method of classifying a sample according to predicted treatment outcome comprising the steps of isolating a gene expression product from at least one informative gene (for example, selected from prostate cancer identification informative genes, prostate cancer differentiation informative genes, and tumor recurrence informative genes) from a sample, for example, one or more cells; and determining a gene expression profile of at least one informative gene, wherein the gene expression profile is correlated with a treatment outcome, thereby classifying the sample with respect to treatment outcome. In one embodiment the sample is a prostate cancer sample. In another embodiment, the gene expression product is mRNA. In yet another embodiment, the gene expression profile is determined utilizing specific hybridization probes, and in a preferred embodiment the gene expression profile is determined utilizing oligonucleotide microarrays. In still another embodiment, the gene expression product is a peptide, and in another embodiment the gene expression profile is determined utilizing antibodies. In preferred embodiments, the predicted treatment outcome is survival after treatment or prostate cancer recurrence. In another embodiment, the informative genes are genes having increased expression in prostate cancer and are selected from the group consisting of the genes in FIGS. 3A–3C2, FIGS. 9A–9D, FIG. 10A, FIGS. 14A–14B, Platelet Derived Growth Factor Receptor, Beta Chromogranin A, and HOXC6. In another embodiment, the informative genes are genes having decreased expression in prostate cancer and are selected from the group consisting of the genes in FIGS. 2A–N, FIGS. 9E–9L, FIG. 10B, FIGS. 14C–14E, Inositol Triphosphate Receptor Type 3, and Beta Galactoside Sialotransferase.

The invention also features a method of identifying a compound for use in modulating prostate cancer development, comprising the steps of providing a cell or cell lysate sample; contacting the cell or cell lysate sample with a candidate compound; and detecting a decrease in expression of at least one informative gene having increased expression in prostate cancer. A candidate compound that decreases the expression of the informative gene is a compound for use in modulating prostate cancer development. In one embodiment, the cell or cell lysate sample is derived from prostate tissue. In another embodiment, the cell or cell lysate sample is derived from a cultured cell, for example, a cultured primary prostate cell or an immortalized prostate cancer cell line. In another embodiment, the informative genes having increased expression in prostate cancer are selected from the group consisting of the genes in FIGS. 3A–3C2, FIGS. 9A–9D, FIG. 10A, FIGS. 14A–14B, Platelet Derived Growth Factor Receptor, Beta Chromogranin A, and HOXC6.

The invention also features a method of identifying a compound for use in modulating (increasing) prostate cancer development, comprising the steps of providing a cell or cell lysate sample; contacting the cell or cell lysate sample with a candidate compound; and detecting an increase in expression of at least one informative gene having decreased expression in prostate cancer. A candidate compound that increases the expression of the informative gene is a compound for use in modulating prostate cancer development. In one embodiment, the cell or cell lysate sample is derived from prostate tissue. In another embodiment, the cell or cell lysate sample is derived from a cultured cell, for example, a cultured primary prostate cell or an immortalized prostate cancer cell line. In another embodiment, the informative genes having decreased expression in prostate cancer are selected from the group consisting of the genes in FIGS. 2A–N, FIGS. 9E–9L, FIG. 10B, FIGS. 14C–14E, Inositol Triphosphate Receptor Type 3, and Beta Galactoside Sialotransferase.

In still another aspect, the invention features a method of identifying a compound that modulates (decreases) the biological activity of an informative gene expression product having increased expression in prostate cancer. The method comprises the steps of a) contacting the informative gene expression product with a candidate compound under conditions suitable for activity of the informative gene expression product; and b) assessing the biological activity level of the informative gene expression product. A candidate compound that decreases the biological activity level of the informative gene expression product relative to a control is a compound that modulates the biological activity of the informative gene expression product having increased expression in prostate cancer. In one embodiment, the method is carried out in a cell or animal. In another embodiment, the method is carried out in a cell free system. In still another embodiment the informative gene expression product is selected from the gene expression products encoded by the genes in FIGS. 3A–3C2, FIGS. 9A–9D, or FIG. 10A, or FIGS. 14A–14B or is Platelet Derived Growth Factor Receptor, Chromogranin A, or HOXC6.

In another aspect, the invention features a method of identifying a compound that decreases expression of an informative gene having increased expression in prostate cancer. The method comprises the steps of a) providing a nucleic acid molecule comprising a promoter region of the informative gene, or part of such a promoter region, operably linked to a reporter gene; b) contacting the nucleic acid molecule with a candidate compound; and c) assessing the level of the reporter gene. A candidate compound that decreases expression of the reporter gene relative to a control is a compound that decreases expression of the informative gene having increased expression in prostate cancer. In one embodiment, the method is carried out in a cell. In another embodiment, the informative gene is selected from the group consisting of the genes in FIGS. 3A–3C2, FIGS. 9A–9D, FIG. 10A, FIGS. 14A–14B, Platelet Derived Growth Factor Receptor, Chromogranin A, and HOXC6.

In another aspect, the invention features a method of identifying a compound that increases expression of an informative gene having decreased expression in prostate cancer. The method comprises the steps of a) providing a nucleic acid molecule comprising a promoter region of the informative gene, or part of such a promoter region, operably linked to a reporter gene; b) contacting the nucleic acid molecule with a candidate compound; and c) assessing the level of the reporter gene. A candidate compound that increases expression of the reporter gene relative to a control is a compound that increases expression of the informative gene having decreased expression in prostate cancer. In one embodiment, the method is carried out in a cell. In another embodiment the informative gene is selected from the group consisting of the genes in FIGS. 2A–2N, FIGS. 9E–9L, FIG. 10B, FIGS. 14C–14E, Inositol Triphosphate Receptor Type 3, and Beta Galactosidase.

In still another aspect, the invention features a method of identifying a polypeptide that interacts with an informative gene expression product having modulated (increased or decreased) expression in prostate cancer in a yeast two-hybrid system. The method comprises the steps of a) providing a first nucleic acid vector comprising a nucleic acid molecule encoding a DNA binding domain and a polypeptide encoded by the informative gene that is increased or decreased in prostate cancer; b) providing a second nucleic acid vector comprising a nucleic acid encoding a transcription activation domain and a nucleic acid encoding a test polypeptide; c) contacting the first nucleic acid vector with the second nucleic acid vector in a yeast two-hybrid system; and d) assessing transcriptional activation in the yeast two-hybrid system. An increase in transcriptional activation relative to a control indicates that the test polypeptide is a polypeptide that interacts with the informative gene expression product having modulated (increased or decreased) expression in prostate cancer.

In other embodiments of the above described compound screening methods, gene expression is determined by assessing the DNA or mRNA level of the gene. Preferably, the DNA or mRNA level is determined utilizing specific hybridization probes. For example, the DNA or mRNA level may be determined utilizing oligonucleotide microarrays. In another embodiment, gene expression is determined by assessing the polypeptide level encoded by the informative gene, for example, using antibodies. In another embodiment, gene expression is determined using mass spectrophotometry.

The invention also features a method for modulating prostate cancer in an individual comprising down-regulating (i.e., inhibiting) in the individual at least one informative gene shown to be expressed, or expressed in increased levels (as compared with a control), in individuals having prostate cancer or at risk for developing prostate cancer. In one embodiment, the informative gene(s) is selected from the group consisting of the genes in FIGS. 3A–3C2, FIGS. 9A–9D, FIG. 10A, FIGS. 14A–14B, Platelet Derived Growth Factor Receptor, Beta Chromogranin A, and HOXC6.

The invention also features a method for modulating prostate cancer in an individual comprising up-regulating (i.e., enhancing) in the individual at least one informative gene shown not to be expressed, or expressed at reduced levels (as compared with a control), in individuals having prostate cancer or at risk for developing prostate cancer. In one embodiment, the informative gene(s) is selected from the group consisting of the genes in FIGS. 2A–N, FIGS. 9E–9L, FIG. 10B, FIGS. 14C–14E, Inositol Triphosphate Receptor Type 3, and Beta Galactoside Sialotransferase.

The invention further relates to a method of assessing treatment efficacy in an individual having prostate cancer, comprising determining the expression level of one or more informative genes at multiple time points, for example, two, three, or more time points during treatment. In one embodiment, a decrease in expression of the one or more informative genes shown to be expressed, or expressed at increased levels (as compared with a control), in individuals having prostate cancer or at risk for developing prostate cancer, is indicative that treatment is effective. In another embodiment, a lack of a decrease in expression of the one or more informative genes indicates that the treatment is less effective. In another embodiment, the at least one informative gene is selected from the group consisting of the genes in FIGS. 3A–3C2, FIGS. 9A–9D, FIG. 10A, FIGS. 14A–14B, Platelet Derived Growth Factor Receptor, Beta Chromogranin A, and HOXC6.

In another embodiment, an increase in expression of the one or more informative genes shown not to be expressed, or expressed at reduced levels (as compared with a control), in individuals having prostate cancer or at risk for developing prostate cancer, is indicative that treatment is effective. In another embodiment, a lack of an increase in expression of the one or more informative genes indicates that the treatment is less effective. In another embodiment, the at least one informative gene is selected from the group consisting of the genes in FIGS. 2A–2N, FIGS. 9E–9L, FIG. 10B, FIGS. 14C–14E, Inositol Triphosphate Receptor Type 3, and Beta Galactoside Sialotransferase.

The invention also relates to an oligonucleotide microarray having immobilized thereon a plurality of oligonucleotide probes specific for one or more informative genes selected from the group consisting of the genes in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase.

In another aspect, the invention features a solid substrate having immobilized thereon a plurality of detection agents specific for one or more informative genes selected from the group consisting of the genes in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase. In one embodiment, the solid substrate is a microarray. In another embodiment, the detection agents are a plurality of oligonucleotide probes specific for one or more informative genes selected from the group consisting of the genes in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase. In still another embodiment, the detection agents are a plurality of gene expression products encoded by one or more informative genes selected from the group consisting of the genes in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase.

BRIEF DESCRIPTION OF THE FIGURES

The patent or application file contains at least one drawing executed in color. Copies of this patent or patent application publication with color drawing will be provided by the Office upon request and payment of the necessary fee.

FIG. 1 is a table of patient characteristics by cohort and a comparison of the clinical characteristics between patient samples included in this study and all patients treated by radical prostatectomy during the same time period. The table displays comparative analysis for all samples together, as well as the subset of patients used in the recurrent versus non-recurrent analysis.

FIGS. 2A–2N show a list of the genes expressed at higher levels in normal prostate samples compared to prostate tumor samples (decreased in prostate tumors relative to normal prostate tissue (control)).

FIGS. 3A–3C2 show a list of the genes expressed at higher levels in prostate tumor samples compared to normal prostate samples (increased in prostate tumors relative to normal prostate tissue (control)).

FIG. 6 is a table of the success rate of the tumor versus normal prediction model tested on an independent surgical cohort.

FIG. 7A is a table of the percentage of epithelium in samples based on type of sample (tumor versus normal), Gleason score, and tumor recurrence.

FIGS. 9A–9D are a table of the 56 genes positively correlating with Gleason score at the p=0.01 level.

FIGS. 9E–9L are a table of the 134 genes negatively correlating with Gleason score at the p=0.01 level.

FIG. 10A is a table of the 15 genes positively correlating with Gleason score at the p=0.001 level.

FIG. 10B is a table of the 14 genes negatively correlating with Gleason score at the p=0.001 level.

FIGS. 14A–14B are a table of genes positively correlating with Gleason score at the p=0.05 level.

FIGS. 14C–14E are a table of genes negatively correlating with Gleason score at the p=0.05 level.

DETAILED DESCRIPTION OF THE INVENTION

Figure 4:
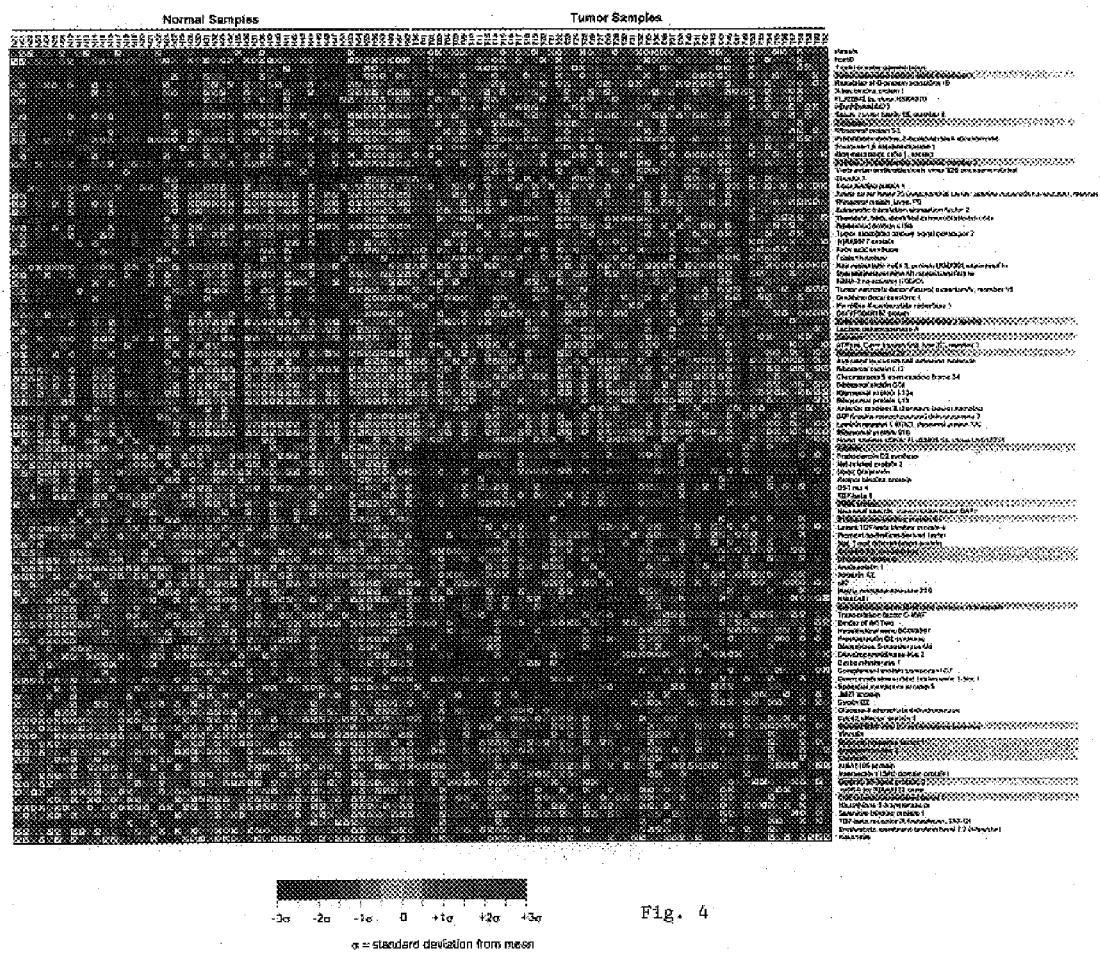
FIG. 4 shows a list of genes that are differentially expressed between prostate tumor and normal prostate tissue samples. The top 50 genes that, based upon the S2N distance, best discriminated between the 50 normal prostate samples and 52 prostate cancer samples are listed ranked according to how well each gene's expression best fits the class distinction (tumor versus normal). The expression difference for each gene in each sample is represented by the number of standard deviations above (red) or below (blue) the mean for that gene across all samples.

The clinical heterogeneity of prostate cancer is striking; some men have indolent disease that remains clinically insignificant even without therapy, whereas other men have aggressive, fatal diseases despite intervention with surgery, radiation therapy or chemotherapy. This has led to the question of whether prostate cancer is molecularly heterogeneous. To address this question, a genomics-based predictor of prostate cancer presence and prostate cancer relapse has been developed. This predictor aids in the diagnosis of prostate cancer, as well as the prognosis for prostate cancer recurrence.

As described herein, global gene expression patterns in 52 tumor samples and 50 normal samples obtained at the time of radical prostatectomy were evaluated, in order to determine if the coordinate expression of groups of genes are associated with: 1) the identity of a sample (i.e., tumor or normal); 2) the state of differentiation (i.e., Gleason score); and 3) the predicted clinical outcome (either non-recurrence of tumor after surgery or recurrence).

In general, the present invention relates to methods for classifying a sample according to the gene expression profile of the sample. In one embodiment, the present invention is directed to classifying a biological sample with respect to a phenotypic effect, e.g., presence or absence of prostate cancer or predicted treatment outcome, comprising the steps of isolating a gene expression product from a sample, for example from a (one or more) cell in the sample, and determining a gene expression profile of at least one informative gene, wherein the gene expression profile is correlated with a phenotypic effect, thereby classifying the sample with respect to phenotypic effect. According to the methods of the invention, samples can be classified as belonging to (i.e., derived from) an individual who has or is likely to develop prostate cancer.

Alternatively, according to methods of the invention, samples can be classified as belonging to a particular class of treatment outcome. In a preferred embodiment, the treatment outcome is prostate cancer recurrence. That is, a sample can be classified as belonging to a high risk class (e.g., a class with a prognosis for a high likelihood of recurrence, or a class with a poor prognosis for survival after treatment) or a low risk class (e.g., a class with a prognosis for a low likelihood of recurrence or a class with a good prognosis for survival after treatment). Duration of illness, severity of symptoms and eradication of disease can also be used as the basis for differentiating, i.e., classifying, samples.

As used herein, by a "gene having increased expression in prostate cancer" is meant a gene having increased expression in prostate cancer compared to normal prostate, a gene having increased expression in prostate cancers having a Gleason score of 6 or greater compared to appropriate controls, or a gene having increased expression in recurrent prostate tumors compared to appropriate controls. These genes are therefore helpful in identifying a patient with prostate cancer, at risk for developing prostate cancer, or at a risk for having a recurrence of prostate cancer. Examples of such genes are provided herein.

As used herein, by a "gene having decreased expression in prostate cancer" is meant a gene having decreased expression in prostate cancer compared to normal prostate, a gene having decreased expression in prostate cancers having a Gleason score of 6 or greater compared to appropriate controls, or a gene having decreased expression in recurrent prostate tumors compared to appropriate controls. These genes are therefore helpful in identifying a patient with prostate cancer, at risk for developing prostate cancer, or at risk for having a recurrence of prostate cancer. Examples of such genes are provided herein.

As used herein, gene expression products are proteins, peptides, or nucleic acid molecules (e.g., mRNA, tRNA, rRNA, or cRNA) that are involved in transcription or translation. The present invention can be effectively used to analyze proteins, peptides, or nucleic acid molecules that are involved in transcription or translation. The nucleic acid molecule levels measured can be derived directly from the gene or, alternatively, from a corresponding regulatory gene. All forms of gene expression products can be measured, including, for example, spliced variants. Similarly, gene expression can be measured by assessing the level of protein or derivative thereof translated from mRNA. The sample to be assessed can be any sample that contains a gene expression product. Suitable sources of gene expression products, i.e., samples, can include cells, lysed cells, cellular material for determining gene expression, or material containing gene expression products. Examples of such samples are blood, plasma, lymph, urine, tissue, mucus, sputum, saliva or other cell samples. Methods of obtaining such samples are known in the art. In a preferred embodiment, the sample is derived from an individual who has been clinically diagnosed as having prostate cancer or at risk of developing prostate cancer. As used herein "obtaining" means acquiring a sample, either by directly procuring a sample from a patient or a sample (tissue biopsy, primary cell, cultured cells), or by receiving the sample from one or more people who procured the sample from the patient or sample.

Genes that are particularly relevant for classification have been identified as a result of work described herein and are shown in FIGS. 2A–N, FIGS. 3A–3C2, FIGS. 9A–9D, FIGS. 9E–9L, FIG. 10A, FIG. 10B, FIGS. 14A–14B, and FIGS. 14C–14E. Platelet Derived Growth Factor Receptor, Beta Chromogranin A, HOXC6, Inositol Triphosphate Receptor Type 3, and Beta Galactoside Sialotransferase are also relevant for classification. The genes that are relevant for classification are referred to herein as "informative genes." Informative genes can be, for example, prostate cancer identification informative genes, for example, all or a subset of the genes shown in FIGS. 2A–2N (having decreased expression in prostate cancer compared to normal prostate tissue) and FIGS. 3A–3C2 (having increased expression in prostate cancer compared to normal prostate tissue), prostate cancer differentiation informative genes, for example, all or a subset of the genes shown in FIGS. 9A–9D, FIG. 10A, and FIGS. 14A–14B (having increased expression in prostate cancers having a Gleason score of 6 or greater, compared to appropriate controls) and FIGS. 9E–9L, FIG. 10B and FIGS. 14C–14E (having decreased expression in prostate cancers having a Gleason score of 6 or greater, compared to appropriate controls), and tumor recurrence informative genes, for example, all or a subset of Platelet Derived Growth Factor Receptor, Beta Chromogranin A, and HOXC6 (having increased expression in recurrent prostate tumors compared to appropriate controls) and Inositol Triphosphate Receptor Type 3 and Beta Galactoside Sialotransferase (having decreased expression in recurrent prostate tumors compared to appropriate controls). Not all informative genes for a particular class distinction must be assessed in order to classify a sample. Similarly, the set of informative genes for one phenotypic effect may or may not be the same as the set of informative genes for a different phenotypic effect. For example, a subset of the informative genes which demonstrate a high correlation with a class distinction can be used. This subset can be, for example, 1 or more genes, 2 or more genes, 3 or more genes, 4 or more genes, 5 or more genes, 10 or more genes, 25 or more genes, or 50 or more genes. It will be understood that the methods of the present invention can classify a sample by evaluating a sample for a combination of genes whose expression is increased in prostate cancer and/or genes that are decreased in prostate cancer.

In one embodiment, the gene expression product is a protein or polypeptide. In this embodiment, determination of the gene expression profile can be made using techniques for protein detection and quantitation known in the art. For example, antibodies specific for the protein or polypeptide can be obtained using methods that are routine in the art, and the specific binding of such antibodies to protein or polypeptide gene expression products can be detected and measured.

"Gene expression profile" as used herein is defined as the level or amount of gene expression of particular genes as assessed by methods described herein. The gene expression profile can comprise data for one or more genes and can be measured at a single time point or over a period of time. Phenotype classification (e.g., treatment outcome, presence or absence of prostate cancer) can be made by comparing the gene expression profile of the sample with respect to one or more informative genes with one or more gene expression profiles (e.g., in a database). Informative genes include, but are not limited to, those shown in FIGS. 2A–N, FIGS. 3A–3C2, FIGS. 9A–9D, FIGS. 9E–9L, FIG. 10A, FIG. 10B, FIGS. 14A–14B and FIGS. 14C–14E, as well as Platelet Derived Growth Factor Receptor, Beta Chromogranin A, HOXC6, Inositol Triphosphate Receptor Type 3, and Beta Galactoside Sialotransferase. Using the methods described herein, expression of numerous genes can be measured simultaneously. The assessment of numerous genes provides for a more accurate evaluation of the sample because there are more genes that can assist in classifying the sample. As discussed above, the sample from which a gene expression profile is determined can be any sample that contains a gene expression product, including cells, lysed cells, cellular material for determining gene expression, or material containing gene expression products. Examples of such samples are blood, plasma, lymph, urine, tissue, mucus, sputum, saliva or other cell samples. In a preferred embodiment, the sample is derived from an individual who has been clinically diagnosed as having prostate cancer or at risk of developing prostate cancer.

In a preferred embodiment, the gene expression product is mRNA and the gene expression levels are obtained, e.g., by contacting the sample with a suitable microarray on which probes specific for all or a subset of the informative genes have been immobilized, and determining the extent of hybridization of the nucleic acid in the sample to the probes on the microarray. Such microarrays are also within the scope of the invention. Examples of methods of making oligonucleotide microarrays are described, for example, in WO 95/11995. Other methods will be readily known to the skilled artisan.

Once the gene expression levels of the sample are obtained, the levels are compared or evaluated against the model, and then the sample is classified. The evaluation of the sample determines whether or not the sample should be assigned to the particular phenotypic class being studied.

The gene expression value measured or assessed is the numeric value obtained from an apparatus that can measure gene expression levels. Gene expression levels refer to the amount of expression of the gene expression product, as described herein. The values are raw values from the apparatus, or values that are optionally rescaled, filtered and/or normalized. Such data is obtained, for example, from a GeneChip® probe array or Microarray (Affymetrix, Inc.) (U.S. Pat. Nos. 5,631,734, 5,874,219, 5,861,242, 5,858,659, 5,856,174, 5,843,655, 5,837,832, 5,834,758, 5,770,722, 5,770,456, 5,733,729, 5,556,752, all of which are incorporated herein by reference in their entirety), and the expression levels are calculated with software (e.g., Affymetrix GENECHIP software). Nucleic acids (e.g., mRNA) from a sample which has been subjected to particular stringency conditions hybridize to the probes on the chip. The nucleic acid to be analyzed (e.g., the target) is isolated, amplified and labeled with a detectable label (e.g., $^{32}$P or fluorescent label) prior to hybridization to the arrays. Once hybridization occurs, the arrays are inserted into a scanner which can detect patterns of hybridization. The hybridization data are collected as light emitted from the labeled groups which are now bound to the probe array. The probes that perfectly match the target produce a stronger signal than those that have mismatches. Since the sequence and position of each probe on the array are known, by complementarity, the identity of the target nucleic acid applied to the probe is determined.

Quantitation of gene profiles from the hybridization of labeled mRNA/DNA microarrays can be performed by scanning the microarrays to measure the amount of hybridization at each position on the microarray with an Affymetrix scanner (Affymetrix, Santa Clara, Calif.). For each stimulus, a time series of mRNA levels (C={C1,C2,C3, . . . Cn}) and a corresponding time series of mRNA levels (M={M1,M2, M3, . . . Mn}) in control medium in the same experiment as the stimulus is obtained. Quantitative data is then analyzed. "Ci" and "Mi" are defined as relative steady-state mRNA levels, where "i" refers to the ith timepoint and "n" to the total number of time points of the entire time course. "$\mu M$" and "$\sigma M$" are defined as the mean and standard deviation of the control time course, respectively. Microarrays are only one method of obtaining gene expression values. Other methods for obtaining gene expression values known in the art or developed in the future can be used with the present invention. Once the gene expression values are prepared, the sample can be classified.

The correlation between gene expression and class distinction can be determined using a variety of methods. Methods of defining classes and classifying samples are described, for example, in U.S. patent application Ser. No. 09/544,627, filed Apr. 6, 2000 by Golub et al., the teachings of which are incorporated herein by reference in their entirety. In one embodiment, gene expression levels are detected and evaluated for expression levels, where genes without variation (e.g., having 5-fold or less variation between any two samples) are filtered out of the analysis. The information provided by the present invention, alone or in conjunction with other test results, aids in sample classification.

In one embodiment, the sample is classified using a weighted voting scheme. The weighted voting scheme advantageously allows for the classification of a sample on the basis of multiple gene expression values. In a preferred embodiment the sample is a prostate cancer patient sample. In a preferred embodiment the sample is classified as belonging to a particular treatment outcome class. In another embodiment the gene is selected from a group of informative genes, including, but not limited to, the genes listed in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase.

For example, one aspect of the present invention is a method of assigning a sample to a known or putative class, e.g., a prostate cancer treatment outcome class, comprising determining a weighted vote of one or more informative genes (e.g., greater than 1, 2, 3, 4, 5, 10, 20, 30, 40 or 50 genes) for one of the classes in accordance with a model built with a weighted voting scheme, wherein the magnitude of each vote depends on the expression level of the gene in the sample and on the degree of correlation of the gene's expression with class distinction; and summing the votes to determine the winning class. The weighted voting scheme is:

$$V_g = a_g(x_g - b_g),$$

wherein $V_g$ is the weighted vote of the gene, g; $a_g$ is the correlation between gene expression values and class distinction, P(g,c), as defined herein; $b_g = (\mu_1(g) + \mu_2(g))/2$ which is the average of the mean $\log_{10}$ expression value in a first class and a second class; $x_g$ is the $\log_{10}$ gene expression value in the sample to be tested; and wherein a positive V value indicates a vote for the first class, and a negative V value indicates a negative vote for the class. A prediction strength can also be determined, wherein the sample is assigned to the winning class if the prediction strength is greater than a particular threshold, e.g., 0.3. The prediction strength is determined by:

$$(V_{win} - V_{lose})/(V_{win} + V_{lose}),$$

wherein $V_{win}$ and $V_{lose}$ are the vote totals for the winning and losing classes, respectively. Moreover, as a consequence of the identification of informative genes for the prediction of treatment outcome, the present invention provides methods for determining a treatment plan for an individual. That is, a determination of the presence or absence of prostate cancer or treatment outcome class to which the sample belongs may dictate that a treatment regimen be implemented. For example, once a health care provider knows to which treatment outcome class the sample, and therefore, the individual from which it was obtained, belongs, the health care provider can determine an adequate treatment plan for the individual. For example, in the treatment of a patient whose gene expression profile, as determined by the present invention, correlates with a poor prognosis, a health care provider could utilize a more aggressive treatment for the patient, or at minimum provide the patient with a realistic assessment of his or her prognosis.

The present invention also provides methods for monitoring the effect of a treatment regimen in an individual by monitoring the gene expression profile for one or more informative genes. For example, a baseline gene expression profile for the individual can be determined, and repeated gene expression profiles can be determined at time points during treatment. A shift in gene expression profile from a profile correlated with poor treatment outcome to a profile correlated with improved treatment outcome is evidence of an effective therapeutic regimen, while a repeated profile correlated with poor treatment outcome is evidence of an ineffective therapeutic regimen.

The present invention also provides information regarding the genes that are important in prostate cancer treatment response, thereby providing additional targets for diagnosis and therapy. It is also clear that the present invention can be used to generate databases comprising informative genes which will have many applications in medicine, research and industry.

Also encompassed in the present invention is the use of gene expression profiles to screen for therapeutic agents. In one embodiment, the present invention is directed to a method of screening for a therapeutic agent for an individual with prostate cancer, comprising isolating a gene expression product from at least one informative gene from one or more cells of the individual with prostate cancer; identifying a therapeutic agent by determining a gene expression profile of at least one informative gene before and after administration of the agent, wherein if the gene expression profile from the individual after administration of the agent is correlated with effective treatment of prostate cancer, then the agent is identified as a therapeutic agent. In another embodiment, the cells are selected from the group consisting of mononuclear blood cells and bone marrow cells. Alternatively, the above method can utilize a cell line derived from an individual with prostate cancer.

The invention also provides methods (also referred to herein as "screening assays") for identifying agents or compounds (e.g., fusion proteins, polypeptides, peptidomimetics, prodrugs, receptors, binding agents, antibodies, small molecules or other drugs, or ribozymes) that alter or modulate (e.g., increase or decrease) the activity of the gene expression products of the informative genes (e.g., polypeptides encoded by the informative genes) as described herein, or that otherwise interact with the informative genes and/or polypeptides described herein. Such compounds can be compounds or agents that bind to informative gene expression products described herein (e.g., the polypeptides encoded by the informative genes in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase), and that have a stimulatory or inhibitory effect on, for example, activity of the polypeptide encoded by an informative gene described herein; or that change (e.g., enhance or inhibit) the ability of a polypeptide encoded by an informative gene to interact with compounds or agents that bind such an informative gene polypeptide; or that alter post-translational processing of such a polypeptide (e.g., agents that alter proteolytic processing to direct the polypeptide from where it is normally synthesized to another location in the cell, such as the cell surface or the nucleus; or agents that alter proteolytic processing such that more polypeptide is released from the cell, etc.). In one example, the binding agent is a prostate cancer binding agent. As used herein, by "a prostate cancer binding agent" is meant an agent as described herein that binds to a polypeptide encoded by an informative gene of the present invention and modulates the occurrence, severity, or progression of prostate cancer. The modulation can be an increase or a decrease in the occurrence, severity, or progression of prostate cancer. In addition, a prostate cancer binding agent includes an agent that binds to a polypeptide that is upstream (earlier) or downstream (later) of the cell signaling events mediated by a polypeptide encoded by an informative gene of the present invention, and thereby modulates the overall activity of the signaling pathway; in turn, the prostate cancer disease state is modulated.

The candidate compound can cause an alteration in the activity of a polypeptide encoded by an informative gene of the present invention. For example, the activity of the polypeptide can be altered (increased or decreased) by at least 1.5-fold to 2-fold, at least 3-fold, or, at least 5-fold, relative to the control. Alternatively, the polypeptide activity can be altered, for example, by at least 10%, at least 20%, 40%, 50%, or 75%, or by at least 90%, relative to the control.

In one embodiment, the invention provides assays for screening candidate compounds or test agents to identify compounds that bind to or modulate the activity of a polypeptide encoded by an informative gene described herein (or biologically active portion(s) thereof), as well as agents identifiable by the assays. As used herein, a "candidate compound" or "test agent" is a chemical molecule, be it naturally-occurring or artificially-derived, and includes, for example, peptides, proteins, synthesized molecules, for example, synthetic organic molecules, naturally-occurring molecule, for example, naturally occurring organic molecules, nucleic acid molecules, and components thereof.

In general, candidate compounds for use in the present invention may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12: 145 (1997)). Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activities should be employed whenever possible.

When a crude extract is found to modulate (i.e., stimulate or inhibit) the expression and/or activity of the informative genes and/or their encoded polypeptides, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits nucleic acid expression, polypeptide expression, or polypeptide biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

In one embodiment, to identify candidate compounds that alter the biological activity of a polypeptide encoded by an informative gene as described herein, a cell, tissue, cell lysate, tissue lysate, or solution containing or expressing a polypeptide encoded by the informative gene (e.g., a polypeptide encoded by a gene in any of FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase), or a fragment or derivative thereof, can be contacted with a candidate compound to be tested under conditions suitable for biological activity of the polypeptide. Alternatively, the polypeptide can be contacted directly with the candidate compound to be tested. The level (amount) of polypeptide biological activity is assessed/measured, either directly or indirectly, and is compared with the level of biological activity in a control (i.e., the level of activity of the polypeptide or active fragment or derivative thereof in the absence of the candidate compound to be tested, or in the presence of the candidate compound vehicle only). If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of the polypeptide encoded by an informative gene of the invention. For example, an increase in the level of polypeptide biological activity relative to a control, indicates that the candidate compound is a compound that enhances (is an agonist of) the polypeptide biological activity. Similarly, a decrease in the polypeptide biological activity relative to a control, indicates that the candidate compound is a compound that inhibits (is an antagonist of) the polypeptide biological activity.

In another embodiment, the level of biological activity of a polypeptide encoded by an informative gene, or a derivative or fragment thereof in the presence of the candidate compound to be tested, is compared with a control level that has previously been established. A level of polypeptide biological activity in the presence of the candidate compound that differs from (i.e., increases or decreases) the control level by an amount that is statistically significant indicates that the compound alters the biological activity of the polypeptide.

The present invention also relates to an assay for identifying compounds (e.g., antisense nucleic acids, fusion proteins, polypeptides, peptidomimetics, prodrugs, receptors, binding agents, antibodies, small molecules or other drugs, or ribozymes) that alter (e.g., increase or decrease) expression (e.g., transcription or translation) of an informative gene or that otherwise interact with an informative gene described herein, as well as compounds identifiable by the assays. For example, a solution containing an informative gene can be contacted with a candidate compound to be tested. The solution can comprise, for example, cells containing the informative gene or cell lysate containing the informative gene; alternatively, the solution can be another solution that comprises elements necessary for transcription/translation of the informative gene. Cells not suspended in solution can also be employed, if desired. The level and/or pattern of informative gene expression (e.g., the level and/or pattern of mRNA or protein expressed) is assessed, and is compared with the level and/or pattern of expression in a control (i.e., the level and/or pattern of the informative gene expressed in the absence of the candidate compound, or in the presence of the candidate compound vehicle only). If the expression level and/or pattern in the presence of the candidate compound differs by an amount or in a manner that is statistically significant from the level and/or pattern in the absence of the candidate compound, or in the presence of the candidate compound vehicle only, then the candidate compound is a compound that alters the expression of an informative gene. Enhancement of informative gene expression indicates that the candidate compound is an agonist of informative gene polypeptide activity. Similarly, inhibition of informative gene expression indicates that the candidate compound is an antagonist of informative gene polypeptide activity.

In another embodiment, the level and/or pattern of an informative gene in the presence of the candidate compound to be tested, is compared with a control level and/or pattern that has previously been established. A level and/or pattern informative gene expression in the presence of the candidate compound that differs from the control level and/or pattern by an amount or in a manner that is statistically significant indicates that the candidate compound alters informative gene expression.

In another embodiment of the invention, compounds that alter the expression of an informative gene, or that otherwise interact with an informative gene described herein, can be identified using a cell, cell lysate, or solution containing a nucleic acid encoding the promoter region of the informative gene operably linked to a reporter gene. As used herein by "promoter" means a minimal nucleotide sequence sufficient to direct transcription, and by "operably linked" means that a gene and one or more regulatory sequences are connected in such a way as to permit gene expression when the appropriate molecules (e.g., transcriptional activator proteins) are bound to the regulatory sequences. Examples of reporter genes and methods for operably linking a reporter gene to a promoter are known in the art. After contact with a candidate compound to be tested, the level of expression of the reporter gene (e.g., the level of mRNA or of protein expressed) is assessed, and is compared with the level of expression in a control (i.e., the level of expression of the reporter gene in the absence of the candidate compound, or in the presence of the candidate compound vehicle only). If the level of expression in the presence of the candidate compound differs by an amount or in a manner that is statistically significant from the level in the absence of the candidate compound, or in the presence of the candidate compound vehicle only, then the candidate compound is a compound that alters the expression of the informative gene, as indicated by its ability to alter expression of the reporter gene that is operably linked to the informative gene promoter. Enhancement of the expression of the reporter gene indicates that the compound is an agonist of the informative gene polypeptide activity. Similarly, inhibition of the expression of the reporter gene indicates that the compound is an antagonist of the informative gene polypeptide activity.

In another embodiment, the level of expression of the reporter in the presence of the candidate compound to be tested, is compared with a control level that has been established previously. A level in the presence of the candidate compound that differs from the control level by an amount or in a manner that is statistically significant indicates that the candidate compound alters informative gene expression.

The present invention also features methods of detecting and/or identifying a compound that alters the interaction between a polypeptide encoded by an informative gene and a polypeptide (or other molecule) with which the polypeptide normally interacts with (e.g., in a cell or under physiological conditions). In one example, a cell or tissue that expresses or contains a compound (e.g., a polypeptide or other molecule) that interacts with a polypeptide encoded by an informative gene (such a molecule is referred to herein as a "polypeptide substrate") is contacted with the informative gene polypeptide in the presence of a candidate compound, and the ability of the candidate compound to alter the interaction between the polypeptide encoded by the informative gene and the polypeptide substrate is determined, for example, by assaying activity of the polypeptide. Alternatively, a cell lysate or a solution containing the informative gene polypeptide, the polypeptide substrate, and the candidate compound can be used. A compound that binds to the informative gene polypeptide or to the polypeptide substrate can alter the interaction between the informative gene polypeptide and the polypeptide substrate by interfering with (inhibiting), or enhancing the ability of the informative gene polypeptide to bind to, associate with, or otherwise interact with the polypeptide substrate.

Determining the ability of the candidate compound to bind to the informative gene polypeptide or a polypeptide substrate can be accomplished, for example, by coupling the candidate compound with a radioisotope or enzymatic label such that binding of the candidate compound to the informative gene polypeptide or polypeptide substrate can be determined by directly or indirectly detecting the candidate compound labeled with $^{125}I$, $^{35}S$, $^{14}C$, or $^{3}H$, and then detecting the radioisotope (e.g., by direct counting of radioemmission or by scintillation counting). Alternatively, the candidate compound can be enzymatically labeled with, for example, horseradish peroxidase, alkaline phosphatase, or luciferase, and the enzymatic label is then detected by determination of conversion of an appropriate substrate to product. In another alternative, one of the other components of the screening assay (e.g., the polypeptide substrate or the informative gene polypeptide) can be labeled, and alterations in the interaction between the informative gene polypeptide and the polypeptide substrate can be detected. In these methods, labeled unbound components can be removed (e.g., by washing) after the interaction step in order to accurately detect the effect of the candidate compound on the interaction between the informative gene polypeptide and the polypeptide substrate.

It is also within the scope of this invention to determine the ability of a candidate compound to interact with the informative gene polypeptide or polypeptide substrate without the labeling of any of the interactants. For example, a microphysiometer can be used to detect the interaction of a candidate compound with a polypeptide encoded by an informative gene or a polypeptide substrate without the labeling of either the candidate compound, the polypeptide encoded by the informative gene, or the polypeptide substrate (McConnell et al., Science 257: 1906–1912 (1992)). As used herein, a "microphysiometer" (e.g., CYTOSENSOR™) is an analytical instrument that measures the rate at which a cell acidifies its environment using a light-addressable potentiometric sensor (LAPS). Changes in this acidification rate can be used as an indicator of the interaction between ligand and polypeptide.

In another embodiment of the invention, assays can be used to identify polypeptides that interact with one or more polypeptides encoded by an informative gene. For example, a yeast two-hybrid system such as that described by Fields and Song (Fields and Song, Nature 340: 245–246 (1989)) can be used to identify polypeptides that interact with one or more polypeptides encoded by an informative gene. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used that includes a nucleic acid encoding a DNA binding domain and a polypeptide encoded by an informative gene, or fragment or derivative thereof, and a second vector is used that includes a nucleic acid encoding a transcription activation domain and a nucleic acid encoding a polypeptide that potentially may interact with the informative gene polypeptide, or fragment or derivative thereof. Incubation of yeast containing the first vector and the second vector under appropriate conditions (e.g., mating conditions such as used in the MATCHMAKER™ system from Clontech) allows identification of colonies that express the markers of the polypeptide(s). These colonies can be examined to identify the polypeptide(s) that interact with the polypeptide encoded by the informative gene or a fragment or derivative thereof. Such polypeptides may be useful as compounds that alter the activity or expression of an informative gene polypeptide.

In more than one embodiment of the above assay methods of the present invention, it may be desirable to immobilize a polypeptide encoded by an informative gene, or a polypeptide substrate, or other components of the assay on a solid support, in order to facilitate separation of complexed from uncomplexed forms of one or both of the polypeptides, as well as to accommodate automation of the assay. Binding of a candidate compound to the polypeptide, or interaction of the polypeptide with a polypeptide substrate in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided that adds a domain that allows the informative gene polypeptide, or the polypeptide substrate to be bound to a matrix or other solid support.

This invention further pertains to novel compounds identified by the above-described screening assays. Accordingly, it is within the scope of this invention to further use a compound identified as described herein in an appropriate animal model. For example, a compound identified as described herein can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein. In addition, a compound identified as described herein can be used to alter activity of a polypeptide encoded by an informative gene, or to alter expression of the informative gene, by contacting the polypeptide or the nucleic acid molecule (or contacting a cell comprising the polypeptide or the nucleic acid molecule) with the compound identified as described herein.

The present invention encompasses a method of treating prostate cancer, comprising the administration of an agent which modulates the expression level or activity of an informative gene product. A therapeutic agent may increase or decrease the level or activity of the gene product. For example, an inhibitor of the kinase FLT3 could be useful in treating prostate cancer. Other suitable therapeutic targets for drug development include genes described herein in FIGS. 2A–N, FIGS. 3A–3C2, FIGS. 9A–9D, FIGS. 9E–9L, FIG. 10A, FIG. 10B, FIGS. 14A–14B, FIGS. 14C–14E, Platelet Derived Growth Factor Receptor, Beta Chromogranin A, HOXC6, Inositol Triphosphate Receptor Type 3, and Beta Galactoside Sialotransferase.

The present invention further relates to antibodies that specifically bind a polypeptide, preferably an epitope, of an informative gene of the present invention (as determined, for example, by immunoassays, a technique well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, for example, anti-Id antibodies to antibodies of the invention), and epitope-binding fragments of any of the above.

The term "antibody," as used herein, refers to immunoglobulin molecules and immunologically active portions of immunoglobulin molecules, and more specifically, molecules that contain an antigen binding site that specifically binds an antigen. The immunoglobulin molecules of the invention can be of any type (for example, IgG, IgE, IgM, IgD, IgA and IgY), and of any class (for example, IgG1, IgG2, IgG3, IgG4, IgA1 and IgA2) or subclass of an immunoglobulin molecule.

In one embodiment, the antibodies are antigen-binding antibody fragments and include, without limitation, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of one or more of the following: hinge region, CH1, CH2, and CH3 domains. Also included in the invention are antigen-binding fragments also comprising any combination of variable region(s) with a hinge region, CH1, CH2, and/or CH3 domains.

The antibodies of the invention may be from any animal origin including birds and mammals. Preferably, the antibodies are human, murine, donkey, sheep, rabbit, goat, guinea pig, hamster, horse, or chicken.

As used herein, "human" antibodies include antibodies having the amino acid sequence of a human immunoglobulin and include antibodies produced by human B cells, or isolated from human sera, human immunoglobulin libraries or from animals transgenic for one or more human immunoglobulins and that do not express endogenous immunoglobulins, as described in U.S. Pat. No. 5,939,598 by Kucherlapati et al., for example.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention that they recognize or specifically bind. The epitope(s) or polypeptide portion(s) may be specified, for example, by N-terminal and/or C-terminal positions, or by size in contiguous amino acid residues. Antibodies that specifically bind any epitope or polypeptide encoded by an informative gene of the present invention may also be excluded. Therefore, the present invention includes antibodies that specifically bind a polypeptide encoded by an informative gene of the present invention, and allows for the exclusion of the same.

The term "epitope," as used herein, refers to a portion of a polypeptide which contacts an antigen-binding site(s) of an antibody or T cell receptor. Specific binding of an antibody to an antigen having one or more epitopes excludes non-specific binding to unrelated antigens, but does not necessarily exclude cross-reactivity with other antigens with similar epitopes.

Antibodies of the present invention may also be described or specified in terms of their cross-reactivity. Antibodies of the present invention may not display any cross-reactivity, such that they do not bind any other analog, ortholog, or homolog of a polypeptide of the present invention. Alternatively, antibodies of the invention can bind polypeptides with at least about 95%, 90%, 85%, 80%, 75%, 70%, 65%, 60%, 55%, or 50% identity (as calculated using methods known in the art) to a polypeptide encoded by an informative gene of the present invention. Further included in the present invention are antibodies that bind polypeptides encoded by informative genes that hybridize to an informative gene of the present invention under stringent hybridization conditions, as will be appreciated by one of skill in the art.

Antibodies of the present invention can also be described or specified in terms of their binding affinity to a polypeptide of the invention. Preferred binding affinities include those with a dissociation constant or Kd less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-13}$ M, $5\times10^{-15}$ M, and $10^{-15}$ M.

The invention also provides antibodies that competitively inhibit binding of an antibody to an epitope of a polypeptide of the invention, as determined by any method known in the art for determining competitive binding, for example, using immunoassays. In particular embodiments, the antibody competitively inhibits binding to the epitope by at least about 90%, 80%, 70%, 60%, or 50%.

Antibodies of the present invention can act as agonists or antagonists of polypeptides encoded by the informative genes of the present invention. For example, the present invention includes antibodies which disrupt interactions with the polypeptides encoded by the informative genes of the invention either partially or fully. The invention also includes antibodies that do not prevent binding, but prevent activation or activity of the polypeptide. Activation or activity (for example, signaling) may be determined by techniques known in the art. Also included are antibodies that prevent both binding to and activity of a polypeptide encoded by an informative gene. Likewise included are neutralizing antibodies.

Antibodies of the present invention may be used, for example, and without limitation, to purify, detect, and target the polypeptides encoded by the informative genes described herein, including both in vitro and in vivo diagnostic and therapeutic methods. For example, the antibodies have use in immunoassays for qualitatively and quantitatively measuring levels of the polypeptides in biological samples. See, for example, Harlow et al., Antibodies: A Laboratory Manual (Cold Spring Harbor Laboratory Press, 2nd ed. 1988).

As discussed in more detail below, the antibodies of the present invention may be used either alone or in combination with other compositions. The antibodies may further be recombinantly fused to a heterologous polypeptide at the N- and/or C–terminus or chemically conjugated (including covalent and non-covalent conjugations) to polypeptides or other compositions. For example, antibodies of the present invention may be recombinantly fused or conjugated to molecules useful as labels in detection assays, or effector molecules such as heterologous polypeptides, drugs, or toxins.

The antibodies of the invention include derivatives that are modified, for example, by the covalent attachment of any type of molecule to the antibody such that covalent attachment does not prevent the antibody from recognizing its epitope. For example, but not by way of limitation, the antibody derivatives include antibodies that have been modified, for example, by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivative can contain one or more non-classical amino acids.

The antibodies of the present invention can be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, or the like, to induce the production of sera containing polyclonal antibodies specific for the antigen. Various adjuvants can be used to increase the immunological response, depending on the host species, and include, but are not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and corynebacterium parvum. Such adjuvants are well known in the art.

Monoclonal antibodies can be prepared using a wide variety of techniques also known in the art, including hybridoma cell culture, recombinant, and phage display technologies, or a combination thereof. For example, monoclonal antibodies can be produced using hybridoma techniques as is known in the art and taught, for example, in Harlow et al., Antibodies: A Laboratory Manual (Cold Spring Harbor Laboratory Press, 2nd ed. 1988). The term "monoclonal antibody" as used herein is not necessarily limited to antibodies produced through hybridoma technology, but also refers to an antibody that is derived from a single clone, including any eukaryotic, prokaryotic, or phage clone.

Human antibodies are desirable for therapeutic treatment of human patients. These antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes. The transgenic mice are immunized with a selected antigen, for example, all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For a detailed discussion of this technology for producing human antibodies and human monoclonal antibodies and protocols for producing such antibodies, see, for example, PCT publications WO 98/24893; WO 96/34096; WO 96/33735; and U.S. Pat. Nos. 5,413,923; 5,625,126; 5,633,425; 5,569,825; 5,661,016; 5,545,806; 5,814,318; and 5,939,598.

In another embodiment, antibodies to the polypeptides encoded by the informative genes as described herein can, in turn, be utilized to generate anti-idiotype antibodies that "mimic" polypeptides of the invention using techniques well known to those skilled in the art. (See, for example, Greenspan & Bona, FASEB J. 7(5):437–444 (1989) and Nissinoff, J. Immunol. 147(8):2429–2438 (1991)). For example, antibodies that bind to and competitively inhibit polypeptide multimerization and/or binding of a polypeptide to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide encoded by an informative gene and/or to bind its ligands, and thereby block its biological activity.

The antibodies or fragments thereof of the present invention can be fused to marker sequences, such as a peptide to facilitate their purification. In one embodiment, the marker amino acid sequence is a hexa-histidine peptide, an HA tag, or a FLAG tag, as will be readily appreciated by one of skill in the art.

The present invention further encompasses antibodies or fragments thereof conjugated to a diagnostic or therapeutic agent. The antibodies can be used diagnostically, for example, to monitor the development or progression of a tumor as part of a clinical testing procedure to determine the efficacy of a given treatment regimen. Detection can be facilitated by coupling the antibody to a detectable substance. Examples of detectable substances include enzymes (such as, horseradish peroxidase, alkaline phosphatase, beta-galactosidase, or acetylcholinesterase), prosthetic group (such as streptavidin/biotin and avidin/biotin), fluorescent materials (such as umbelliferone, fluorescein, fluorescein isothiocyanate, rhodamine, dichlorotriazinylamine fluorescein, dansyl chloride or phycoerythrin), luminescent materials (such as luminol), bioluminescent materials (such as luciferase, luciferin, and aequorin), radioactive materials (such as, $^{125}$I, $^{131}$I, $^{111}$In or $^{99}$Tc), and positron emitting metals using various positron emission tomographies, and nonradioactive paramagnetic metal ions.

In an additional embodiment, an antibody or fragment thereof can be conjugated to a therapeutic moiety such as a cytotoxin, for example, a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (for example, daunorubicin (formerly daunomycin) and doxorubicin), antibiotics (for example, actinomycin, bleomycin, mithramycin, and anthramycin (AMC)), and anti-mitotic agents (for example, vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, for example, angiostatin or endostatin; or, biological response modifiers such as, for example, lymphokines, interleukins, granulocyte macrophase colony stimulating factor ("GM-CSF"), granulocyte colony stimulating factor ("G-CSF"), or other growth factors.

Antibodies of the invention can also be attached to solid supports. These are particularly useful for immunoassays or purification of the target antigen. Such solid supports include, but are not limited to, glass, cellulose, silicon, polyacrylamide, nylon, polystyrene, polyvinyl chloride or polypropylene. Techniques for conjugating such therapeutic moiety to antibodies are well known in the art, see, for example, Arnon et al., "Monoclonal Antibodies For Immunotargeting Of Drugs In Cancer Therapy", in Monoclonal Antibodies And Cancer Therapy, Reisfeld et al. eds., pp. 243–56 (Alan R. Liss, Inc. 1985).

Alternatively, an antibody can be conjugated to a second antibody to form an antibody heteroconjugate as described by Segal in U.S. Pat. No. 4,676,980.

An antibody of the invention, with or without conjugation to a therapeutic moiety, administered alone or in combination with cytotoxic factor(s) and/or cytokine(s), can be used as a therapeutic.

Antisense antagonists of the informative genes of the present invention are also included. Antisense technology can be used to control gene expression through antisense DNA or RNA, or through triple-helix formation. Antisense techniques are discussed for example, in Okano, J., Neurochem. 56:560 (1991). The methods are based on binding of a polynucleotide to a complementary DNA or RNA. In one embodiment, an antisense sequence is generated internally by the organism, in another embodiment, the antisense sequence is separately administered (see, for example, O'Connor, J., Neurochem. 56:560 (1991)).

In one embodiment, the 5' coding portion of an informative gene can be used to design an antisense RNA oligonucleotide from about 10 to 40 base pairs in length. Generally, a DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid of the invention. Such a vector contains the sequence encoding the antisense nucleic acid. The vector can remain episomal or become chromosomally integrated, as long as it can be transcribed to produce the desired antisense RNA. Vectors can be constructed by recombinant DNA technology and can be plasmid, viral, or otherwise, as is known to one of skill in the art.

Expression can be controlled by any promoter known in the art to act in the target cells, such as vertebrate cells, and preferably human cells. Such promoters can be inducible or constitutive and include, without limitation, the SV40 early promoter region (Bernoist and Chambon, Nature 29:304–310(1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), and the regulatory sequences of the metallothionein gene (Brinster et al., Nature 296:39–42 (1982)).

The antisense nucleic acids of the invention comprise a sequence complementary to at least a portion of an RNA transcript of an informative gene. Absolute complementarity, although preferred, is not required. A sequence "complementary to at least a portion of an RNA," referred to herein, means a sequence having sufficient complementarity to be able to hybridize with the RNA, forming a stable duplex. The ability to hybridize will depend on both the degree of complementarity and the length of the antisense nucleic acid. Generally, the larger the hybridizing nucleic acid, the more base mismatches with the RNA it may contain and still form a stable duplex. One skilled in the art can ascertain a tolerable degree of mismatch by use of standard procedures to determine the melting point of the hybridized complex.

Oligonucleotides that are complementary to the 5' end of the RNA, for example, the 5' untranslated sequence up to and including the AUG initiation codon, are generally regarded to work most efficiently at inhibiting translation. However, sequences complementary to the 3' untranslated sequences of mRNAs have been shown to be effective at inhibiting translation of mRNAs as well. Thus, oligonucleotides complementary to either the 5'- or 3'-non-translated, non-coding regions of a nucleotide sequence can be used in an antisense approach to inhibit mRNA translation. Oligonucleotides complementary to the 5' untranslated region of the mRNA can include the complement of the AUG start codon. Antisense oligonucleotides complementary to mRNA coding regions can also be used in accordance with the invention. In one embodiment, the antisense nucleic acids are at least six nucleotides in length, and are preferably oligonucleotides ranging from about 6 to about 50 nucleotides in length. In other embodiments, the oligonucleotide is at least about 10, 17, 25 or 50 nucleotides in length.

The antisense oligonucleotides of the invention can be DNA or RNA, or chimeric mixtures, or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide can include other appended groups such as peptides (for example, to target host cell receptors in vivo), or agents that facilitate transport across the cell membrane, or the blood-brain barrier, or intercalating agents.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625–6641 (1987)). The oligonucleotide is a 2'-O-methylribonucleotide (Inoue et al., Nucl. Acids Res. 15:613–16148 (1987)), or a chimeric RNA–DNA analog (Inoue et al., FEBS Lett. 215:327–330 (1987)).

Antisense oligonucleotides of the invention may be synthesized by standard methods known in the art, for example, by use of an automated DNA synthesizer.

Potential antagonists of informative genes of the present invention also include catalytic RNA, or a ribozyme. Hammerhead ribozymes cleave mRNAs at locations dictated by flanking regions that form complementary base pairs with the target mRNA. The target mRNA has the following sequence of two bases: 5'-UG-3'. The construction and production of hammerhead ribozymes is well known in the art and is described more fully in Haseloff and Gerlach (Nature 334:585–591 (1988)). Preferably, the ribozyme is engineered so that the cleavage recognition site is located near the 5' end of the mRNA in order to increase efficiency and minimize the intracellular accumulation of non-functional mRNA transcripts.

Ribozymes of the invention can be composed of modified oligonucleotides (for example for improved stability, targeting, and the like). DNA constructs encoding the ribozyme can be under the control of a strong constitutive promoter, such as, for example, pol III or pol II promoter, so that a transfected cell will produce sufficient quantities of the ribozyme to destroy endogenous target mRNA and inhibit translation. Since ribozymes, unlike antisense molecules, are catalytic, a lower intracellular concentration is generally required for efficiency.

The present invention also provides pharmaceutical compositions, including both therapeutic and prophylatic compositions. Compositions within the scope of this invention include all compositions wherein the therapeutic abent, antibody, fragment or derivative, antisense oligonucleotide or ribozyme is contained in an amount effective to achieve its intended purpose, for e example, for increasing or decreasing informative gene expression and/or biological activity. While individual needs vary, determination of optimal ranges of effective amounts of each component is within the skill of the art. The effective dose is a function of a number of factors, including the specific antibody, the antisense construct, ribozyme or polypeptide of the invention, the presence of a conjugated therapeutic agent (see below), the patient and their clinical status.

Mode of administration may be by parenteral, subcutaneous, intravenous, intramuscular, intraperitoneal, transdermal, or buccal routes. Alternatively, or concurrently, administration may be orally. The dosage administered will be dependent upon the age, health, and weight of the recipient, kind of concurrent treatment, if any, frequency of treatment, and the nature of the effect desired.

Such compositions generally comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

The compositions of the invention can be administered alone or in combination with other therapeutic agents. Therapeutic agents that can be administered in combination with the compositions of the invention, include but are not limited to chemotherapeutic agents, antibiotics, steroidal and non-steroidal anti-inflammatories, conventional immunotherapeutic agents, cytokines and/or growth factors. Combinations may be administered either concomitantly, for example, as an admixture, separately but simultaneously or concurrently; or sequentially. This includes presentations in which the combined agents are administered together as a therapeutic mixture, and also procedures in which the combined agents are administered separately but simultaneously, for example, as through separate intravenous lines into the same individual. Administration "in combination" further includes the separate administration of one of the compounds or agents given first, followed by the second.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that can be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In additional embodiments, the compositions of the invention are administered in combination with other therapeutic or prophylactic regimens, such as, for example, radiation therapy.

The present invention is further directed to therapies which involve administering pharmaceutical compositions of the invention to an animal, preferably a mammal, and most preferably a human patient for treating one or more of the described disorders. Therapeutic compositions of the invention include, for example, therapeutic agents identified in screening assays, antibodies of the invention (including fragments, analogs and derivatives thereof as described herein), antisense oligonucleotides, ribozymes and nucleic acids encoding same. The compositions of the invention can be used to treat, inhibit, prognose, diagnose or prevent diseases, disorders or conditions associated with aberrant expression and/or activity of a polypeptide of the invention, including, but not limited to, any one or more of the diseases, disorders, or conditions such as, for example, prostate cancer.

The treatment and/or prevention of diseases and disorders associated with aberrant expression and/or activity of a polypeptide of the invention includes, but is not limited to, alleviating symptoms associated with those diseases and disorders.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Furthermore, the dosage and frequency of administration of antibodies of the invention may be reduced by enhancing uptake and tissue penetration of the antibodies by modifications such as, for example, lipidation or addition of cell-specific tags.

The compounds or pharmaceutical compositions of the invention can be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The invention provides methods of treatment, inhibition and prophylaxis by administration to a subject of an effective amount of a compound or pharmaceutical composition of the invention. In one aspect, the compound is substantially purified such that the compound is substantially free from substances that limit its effect or produce undesired side-effects. The subject is preferably an animal, including but not limited to animals such as cows, pigs, horses, chickens, cats, dogs, etc., and is preferably a mammal, and most preferably human.

Various delivery systems are known and can be used to administer a composition of the invention, for example, encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, and the like as will be known by one of skill in the art.

Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, for example, in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, such as a liposome (Langer, Science 249:1527–1533 (1990)).

In yet another embodiment, the compound or composition can be delivered in a controlled release system. Furthermore, a controlled release system can be placed in proximity of the therapeutic target, thus requiring only a fraction of the systemic dose (see, e.g., Goodson, in Medical Applications of Controlled Release, supra, vol. 2, pp. 115–138 (1984)). In a further embodiment, a pump may be used. In another embodiment, polymeric materials can be used.

In a particular embodiment where the compound of the invention is a nucleic acid encoding a protein, the nucleic acid can be administered in vivo to promote expression of its mRNA and encoded protein, by constructing it as part of an appropriate nucleic acid expression vector and administering, for example, by use of a retroviral vector, or by direct injection, or by use of microparticle bombardment for example, a gene gun, or coating with lipids or cell-surface receptors or transfecting agents, or by administering it in linkage to a homeobox-like peptide which is known to enter the nucleus (see e.g., Joliot et al., Proc. Natl. Acad Sci. USA 88:1864–1868 (1991)). Alternatively, a nucleic acid can be introduced intracellularly and incorporated within host cell DNA for expression, by homologous recombination.

The present invention also provides kits that can be used in the above methods. In one embodiment, a kit comprises a pharmaceutical composition of the invention in one or more containers.

In another embodiment, the kit is a diagnostic kit for use in testing biological samples. The kit can include a control antibody that does not react with the polypeptide of interest in addition to a specific antibody or antigen-binding fragment thereof which binds to the polypeptide (antigen) of the invention being tested for in the biological sample. Such a kit may include a substantially isolated polypeptide antigen comprising an epitope that is specifically immunoreactive with at least one anti-polypeptide antigen antibody. Further, such a kit can include a means for detecting the binding of said antibody to the antigen (for example, the antibody may be conjugated to a fluorescent compound such as fluorescein or rhodamine which can be detected by flow cytometry). In a further embodiment, the kit may include a recombinantly produced or chemically synthesized polypeptide antigen. The polypeptide antigen of the kit may also be attached to a solid support.

In an alternative embodiment, the detecting means of the above-described kit includes a solid support to which the polypeptide antigen is attached. The kit can also include a non-attached reporter-labeled anti-human antibody. Binding of the antibody to the polypeptide antigen can be detected by binding of the reporter-labeled antibody.

In an additional embodiment, the invention includes a diagnostic kit for use in screening serum samples containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In another embodiment, the antibody may be a monoclonal antibody. The detecting means of the kit can include a second, labeled monoclonal antibody. Alternatively, or in addition, the detecting means can include a labeled, competing antigen.

In one diagnostic configuration, the test serum sample is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. Generally, the reagent is washed again to remove unbound labeled antibody, and the amount of reporter associated with the reagent is determined. The reporter can be an enzyme, for example, which is detected by incubating the solid phase in the presence of a suitable fluorometric, luminescent or calorimetric substrate, as is standard in the art.

The solid surface reagent in the above assay is prepared by known techniques for attaching protein material to solid support material. Suitable solid support materials include, for example and without limitation, polymeric beads, dip sticks, 96-well plate or filter material.

The present invention also features arrays, for example, microarrays that have a plurality of oligonucleotide probes for informative genes identified herein immobilized thereon. The oligonucleotide probe may be specific for one or more informative genes, selected from those shown in FIGS. 2A–N, FIGS. 3A–3C2, FIGS. 9A–9D, FIGS. 9E–9L, FIG. 10A, FIG. 10B, FIGS. 14A–14B and FIGS. 14C–14E, as well as Platelet Derived Growth Factor Receptor, Beta Chromogranin A, HOXC6, Inositol Triphosphate Receptor Type 3, and Beta Galactoside Sialotransferase. Methods for making oligonucleotide microarrays are well known in the art, and are described, for example, in WO 95/11995, the entire teachings of which are hereby incorporated by reference.

The invention also relates to a solid substrate, for example, an array, having immobilized thereon a plurality of detection agents that can be used to detect expression and/or biological activity of informative genes or informative gene products. Examples of detection agents include oligonucleotide probes specific for one or more informative genes and polypeptides (gene expression products) encoded by one or more informative genes. Such arrays can be used to carry out methods for identifying and/or diagnosing bone resorption diseases or bone generating diseases, predicting the likelihood of developing such diseases, identifying compounds for used in treating such diseases, and assessing efficacy of treatment of such diseases, as described herein. In one embodiment, the informative genes are selected from the group consisting of the genes in FIGS. 2A–N, FIGS. 3A–3C2, FIGS. 9A–9D, FIGS. 9E–9L, FIG. 1A, FIG. 10B, FIGS. 14A–14B and FIGS. 14C–14E, as well as Platelet Derived Growth Factor Receptor, Beta Chromogranin A, HOXC6, Inositol Triphosphate Receptor Type 3, and Beta Galactoside Sialotransferase. Polypeptide arrays can be used with antibodies or other polypeptides that bind to the polypeptides encoded by the informative genes.

Methods and techniques applicable to array (including protein array) synthesis have been described in PCT Application Nos. WO 00/58516, and WO 99/36760, U.S. Pat. Nos. 5,143,854, 5,242,974, 5,252,743, 5,324,633, 5,384, 261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

The present invention also contemplates many uses for detection agents attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040, 138, 6,177,248 and 6,309,822. Genotyping and uses therefore are shown in U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The invention will be further described with reference to the following non-limiting examples. The teachings of all the patents, patent applications and all other publications and cited herein are incorporated by reference in their entirety.

EXEMPLIFICATION

Example 1

Sample Identification

From 1995 to 1997, samples of prostate tumors and non-tumor prostate tissue (normal prostate tissue) were collected from consented patients undergoing radical prostatectomy at the Brigham and Women's Hospital (Boston, Mass.). Samples were embedded in optimal cutting temperature (OCT) solution, snap-frozen, and stored in liquid nitrogen. Two hundred thirty-five (235) tumor samples were cryosectioned and histologically reviewed by an experienced prostate pathologist. Sixty-five samples (27.7%) with tumor present on opposing sides of the sample that also had available corresponding normal tissue were included for further analysis. All tumor samples were prospectively reviewed by the same pathologist for Gleason score (described below) and all tumor and normal samples were reviewed to quantify the proportion of the sample comprised of tumor epithelium, normal epithelial, stromal, inflammatory and/or urothelial cells (when present). The original surgical pathology report of the radical prostatectomy was used to determine other associated pathological features including lymph node or seminal vesicle involvement, capsular penetration and/or positive surgical margins and perineural invasion.

To determine whether the included cases were representative of the larger surgical cohort the study group was compared to all patients undergoing radical prostatectomy for prostate cancer at the Brigham and Women's Hospital between 1995 and 1997. There were no statistically significant differences between these groups with respect to age, pre-operative serum PSA, clinical stage, pathological stage, Gleason score or, prostate gland volume; and the rates at which cancer was detected at the surgical margin, in the seminal vesicles, or in resected pelvic lymph nodes (FIG. 1). These data suggest that the patients and their corresponding tumors selected for expression analysis are representative of the types of patients and tumors presenting for prostatectomy.

Example 2

Preparation of Samples for Microarray Hybridization and Measurement of Gene Expression High-quality oligonucleotide based expression data was obtained from 52 prostate tumors and 50 prostate samples lacking detectable tumor (referred to as "normal prostate" here forward) as follows. Total RNA was extracted from the OCT-embedded specimens after tissue homogenization (with a Polytron PT 2100 tissue homogenizer) using Trizol reagent (Life Technologies, Gaithersberg, Va.). During all processing, the thawing of specimens was minimized so as to limit RNA degradation. In two large batches, using pooled reagents and established methods (Golub, et al., Science 286: 531–537 (1999)), labeled cRNA (referred to as "target") was synthesized for each sample from a minimum of 10 micrograms of total RNA. Seven replicate RNA samples (5 tumors and 2 normal samples) with excess RNA were included to assess expression variability introduced by sample preparation and hybridization. Four replicate samples of universal total RNA (Stratagene®) derived from a mixture of RNA from 7 cancer cell lines, were also included as controls to determine if major differences in gene expression existed between the two batches (2 samples were included in each batch of target preparation). The target cRNA from each sample, replicate, and control was quantified by spectrophotometry and an aliquot of 20 micrograms was fragmented using heat and a high-salt buffer (Golub, supra).

The fragmented target for each sample was hybridized to Affymetrix® human 95Av microarrays (containing 12,600 total features for genes, ESTs, and controls) which were stained with streptavidin-phycoerythrin followed by an anti-biotin antibody (Golub, supra). A con-focal argon laser (Hewlett Packard) measured the fluorescence intensity for all gene probes on the microarray and GeneChip® software was used to calculate the level of expression (referred to as the average difference) for each gene of the 12,600 genes represented on the microarray (the identity of each gene is associated with a known GeneBank Accession number). The expression information of each sample was saved as a single file (Golub, supra; Tamayo, et al., Proc. Natl. Acad. Sci. U.S.A. 96: 2907–2912 (1999)).

Example 3

Early Expression Analysis: Quality Assessment, Scaling, Filtering, and Statistical Methods Gene expression files where overall microarray staining intensity, the percentage of genes detected, or the mean average difference were 2 standard deviations outside the mean level of the dataset were excluded. To minimize the effect of technical variation on subsequent analysis, expression files from each sample included in subsequent experiments were scaled together (also referred to as "normalized"). Files were scaled by multiplying the average difference of each gene by the ratio of the mean average difference for all genes on the sample array and the mean average difference of the selected reference microarray representing the median value for the mean average difference of all arrays.

To exclude genes with minimal variation, the average difference values were set at lower (10) and upper thresholds (16000) and genes without variation (<5-fold between any two samples) across the experiment were excluded (i.e., filtered out).

Descriptive statistics were used to report patient characteristics. For continuous variables, the Wilcoxon rank sum test (Wilcoxin, Biometrics 1: 80–83 (1945)) was used to test for differences between the study sample and the population of patients treated during the 1993–1997 time period and between the patients who recurred and those who did not. Tests for differences in these groups on ordered, categorical variables were done using the exact methods described by Mehta (Biometrics 30: 819–825 (1984)). Fisher's Exact Test (Cox, Analysis of Binary Data. London, Mechuen and Co. (1970)) was used to test for differences between the groups on dichotomous variables.

Summary statistics were computed for the percent epithelial cells in tumor tissue and normal tissue (two sites each per patient). The differences between tumor tissue and normal tissue for site 1, site 2, and the average of the two sites was computed using the Wilcoxon signed rank test.

Example 4

Gene Expression Data for Tumor Samples Versus Normal Samples

Expression data was available for 50 normal samples and 52 tumor samples. After scaling, thresholding, and filtering, 6034 genes remained for analysis. Unsupervised methods (hierarchical clustering and self organized maps (SOMs)) were performed as previously described (Eisen, et al., Proc. Natl. Acad. Sci. U.S.A. 95: 14863–14868 (1998); and Tamayo, supra). The Signal-to-Noise metric was calculated using the absolute value of the difference in the mean expression of any given gene in the tumor versus normal samples divided by the sum of the standard deviations (Golub, supra). The supervised methods of analysis used included nearest neighbor analysis (knn) for class distinction (i.e., genes best discriminating between tumor and normal based on expression) and class prediction using leave-one-out-cross validation.

The results of both forms of supervised methods were compared to data generated after 1000 testings of randomly permuted class distinctions (permutation testing). During this permutation testing, the tumor/normal class distinctions were randomized across all 102 samples (thus, any given sample has a 52/50 chance of being assigned either a tumor or normal designation). The new assignments (with 52 randomly chosen "tumors" and 50 randomly chosen "normal samples (normals)" are then subjected to both knn and leave-one-out cross validation. Because the two classes are randomly assigned, there should be many fewer genes associated with the random class distinction than the actual class distinction if a true difference exits between the actual class distinction. However, if there is no true difference in gene expression in the actual class distinction, the randomly generated class distinctions should have equivalent results. By performing 1000 permutations of the random class assignments, comparing the performance of the actual class distinction to the random class distinction can give estimates of significance based on the number of times the random class distinction had results similar to the actual class distinction (i.e., p=0.001) would suggest that one out of the 1000 random class permutations equaled the actual class distinction, p=0.05 reports that 50 out of the 1000 matched the actual class distinction). This permutation testing was used to empirically calculate the significance of association seen between the tumor and normal classes and those genes matching the class distinction better than p=0.001 were identified.

Example 5

Genes Identified in Tumor Normal Class Distinction

The pathological distinction between prostate cancer and normal prostate epithelium can be difficult when the cancers are well to moderately differentiated. However, prostate cancer cells have undergone transformation and have the potential to behave very differently from normal epithelial cells. It was assessed whether, despite the pathological similarities, significant differences in gene expression were present.

A signal-to-noise metric (S2N), measuring the distance of each gene to the class distinction tumor versus normal was determined as previously described (Golub, supra). S2N measurements were also calculated for the samples after 1000 randomly assigned ("permuted") class distinctions as described above. The comparison of the actual data to the permuted data showed that 139 genes had higher expression in normal samples versus tumor samples (FIGS. 2A–2N) and 317 genes had higher expression in the tumor samples compared to the normal (at the 0.001 level) (FIGS. 3A–3C2). In FIG. 4, the top 50 genes (high in tumor/low in normal; first 50 genes listed) and the top 50 genes (high in normal/low in tumor; second 50 genes listed) are shown ranked by S2N.

Once those genes best distinguishing between tumor and normal prostate samples were identified, the top 50 genes in each list were reviewed for: 1) previous literature confirming a difference in expression between tumor and normal samples, 2) their chromosomal location, and 3) genes with common up-stream transcriptional regulation.

Genes with High Expression in Normal Samples

Of the 139 genes passing permutation testing, the top 50 are presented in FIG. 4. TGF-beta 3 (Djonov et al., Prostate 31: 103–109 (1997)), selenium binding protein (Yang and Sytkowski, Cancer Res. 58: 3150–3153 (1998)), glutathione S-transferase Pi (Nelson, et al., Urology 57(4 Suppl 1): 39–45 (2001)), Annexin 2 (Chetcuti et al. (2001), Cancer Res. 61: 6331–6334 (2001)), and latent transforming growth factor beta (Eklov et al., Cancer Res. 53: 3193–3197 (1993)) have been shown previously to be down regulated in neoplastic prostatic epithelium when compared to normal. Genes sharing chromosomal locations with loci linked with familial prostate cancer included: S100 calcium-binding protein A4 (1q21), Matrix metalloproteinase 23B (1p36.3), KIAA0451 gene product (1), JM27 protein (X), Glucose-6-phosphate dehydrogenase (Xq28), Centrin EF-hand protein 2 (Xq28), Dihydropyrimidinase-like 2 (8p22-p21), and Clusterin (8p21-p12). Finally, there were two groups of genes sharing common signaling pathways and/or transcriptional regulation. The top two genes identified by S2N as having consistently high expression in normal samples compared to tumors were adipsin and Prostaglandin D2 Synthase. These two proteins represent a down-stream target of PPARgamma (Forman et al., Cell 83: 803–812 (1995)) and an enzyme involved in the synthesis of PPARgamma ligand (Forman, supra), respectively. The other set of genes had potential nutritional implications. Together with selenium binding protein, other nutrition related genes such as retinal binding protein and matrix Gla protein (regulated by Vitamin D) had decreased expression in tumors compared to normal samples.

Genes with High Expression in Tumor Samples

Of the 317 genes passing permutation testing because of their increased expression in tumor tissues, Hespin was the gene whose expression most strongly correlated with the tumor/normal distinction, as suggested by other recent reports (Dhanasekaran et al., Nature 412: 822–826 (2001); and Welsh, et al. Cancer Res 61: 5974–5978 (2001)). Other genes with increased expression in tumors and previous evidence in the literature independently supporting increased expression in prostate cancer include Hsp60 (Comford et al., Cancer Res. 60: 7099–7105 (2000)), EpCAM (Poczatek et al., J. Urol. 162: 1462–1466 (1999)), Fatty acid synthase (Welsh, supra); (Myers et al., Hum. Pathol. 27: 1021–1024 (1996)), prostate specific membrane antigen (Folate hydrolase) (Silver et al., Clin. Cancer Res. 3: 81–85 (1997)), NM23 (Myers, supra); Jensen et al. World J. Urol. 14(Suppl. 1): S21–S255 (1996)), Spermidine/spermine N1-acetyltransferase (Bettuzzi et al., Cancer Res. 60: 28–34 (2000)), and ornithine decarboxylase (ODC) (Bettuzzi, supra). When the list of 50 genes are viewed as a whole, genes downstream of MYC (hsp60, ODC, and LDHA) and IL-6 (X-box binding protein 1 and a procolloagen-proline isomerase) were present.

Example 6

Tumor Versus Normal Prediction Model

Figure 5A:
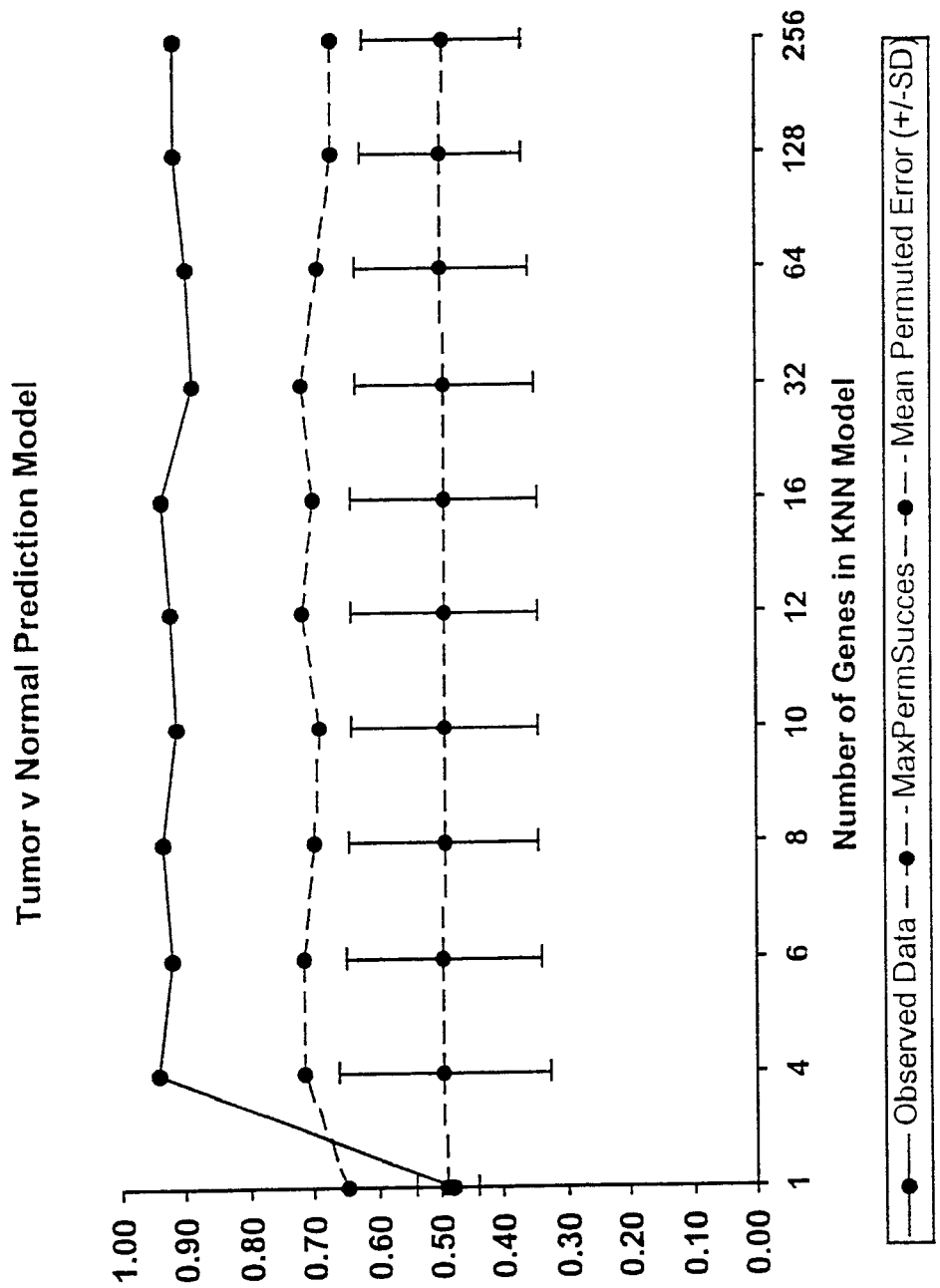
FIG. 5A is a graph of the predictability of a tumor versus normal prediction model for prostate cancer based on the number of genes used in the model.

The question of whether the expression of these genes (or subgroups of these genes) could be used to predict the identity of an unknown sample (tumor versus normal) was next examined. In order to build a tumor versus normal prediction model the S2N metric was used to rank genes based on the class distinction in 101 samples and the identity (tumor or normal) of a left-out sample was predicted using its three nearest neighbors as follows (Golub, supra). The expression files for 51 normal prostate samples and 51 prostate tumor samples were scaled together and imported into GeneCluster. Genes without significant variation were excluded (Threshold minimum 10, maximum 16,000; Max fold Difference=5, Max minus min=50). Of the 6034 genes remaining, a series of models using increasing numbers of genes were tested and the success rate for each model during leave on out cross validation is demonstrated below. For each model, each sample was initially left out of the set and the remaining 101 samples were used to rank genes according to how well they fit the class distinction based on signal to noise. The top "n" genes best distinguishing between the two classes (tumor versus normal) were chosen by the software for an "n" gene model. The expression of these genes were then used in a nearest neighbor analysis to predict the identity of the sample initially left out. This process was performed 102 times with each sample being left out once. The success rate depicted in FIG. 5A is the number of correct predictions divided by the total number of predictions (102).

To determine if the success rate with the actual class distinctions (tumor versus normal) was greater than if the same samples were used but with random class distinctions (two classes with 51 samples in each class but with random assignment without respect for whether the sample was actually a tumor or normal). One thousand permutations of random class distinction was performed for each of the gene models tested. The mean (+/− Standard Deviation as vertical error bars), maximum success rate, and minimum success rate for each gene model is presented below. The success rate for the models generated from the true class distinctions consistently outperformed the random class distinctions with the exception of the single gene model. In this manner, each sample was withheld and predicted using the information derived from the remaining samples. The number of genes used in the nearest-neighbor class prediction models was varied from 1 to 256. While a model using only a single gene had poor accuracy (50%), models that utilized 4 or more genes were uniformly able to predict the class of the held-out sample with greater than 90% accuracy (FIG. 5A). The 16 gene model were also successful 85% of the time when applied to normalized data from a set of prostate tumors processed and scanned at an outside institution, suggesting differences in gene expression between tumor and normal samples are relatively consistent (see below). Of note, the same tumor and normal samples were repeatedly incorrectly classified. Whether these misclassifications were due to true failures of the models or were secondary to introduced artifact (like the occult presence of tumor within a "normal" specimen) is not known, as the entire tumor sample was used after the initial pathological evaluation thus precluding further description.

Figure 5B:
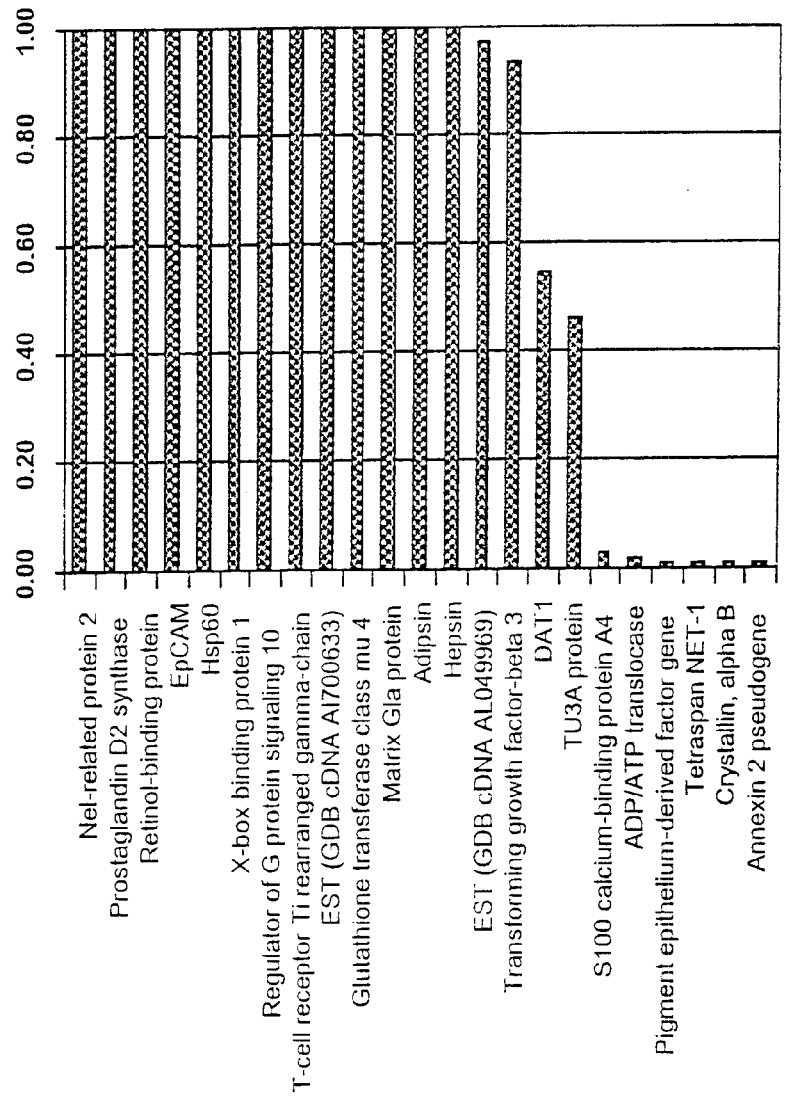
FIG. 5B is a histogram of the genes best distinguishing between tumor and normal samples in the tumor versus normal predication model, ranked according to signal to noise difference between the two classes. The histogram depicts in what percentage of the 102 cross validation trials each gene was used to distinguish between tumor and normal.

In the analysis presented here, there was a near constant set of genes selected to build each predictor. As an example, in the 16 gene-model, a set of 15 genes was used in the vast majority of the models built (95% of the time) (FIG. 5B). This subset of genes would thus appear to be good candidates for further development, whether or not directly linked to tumorigenesis, as diagnostic or early detection markers.

In order to estimate the probability of deriving such models by chance alone, a novel application of permutation testing was used. The tumor and normal designations for each of the 102 specimens were randomized within the dataset to generate 1000 permuted datasets. For each of the randomly generated datasets, nearest neighbor predictors were built and tested in leave-one out cross validation. The mean accuracy of all multi-gene models (1 to 256 genes) generated using the permuted data was 50±7%. The maximum accuracy obtained by the best model generated during the 1000 permutations was 72%. Thus, the 90%+ accuracy of the tumor versus normal prediction models greatly exceeded that obtainable by chance alone (FIG. 5A).

Example 7

Validation of Tumor/Normal Prediction

In order to validate initial observations from the dataset including 50 normal samples and 52 tumors for prediction of tumors/normal samples, expression data for 8 normal samples and 27 prostate tumors were obtained from an outside source. All methods including tumor identification and processing, RNA isolation, labeled cRNA generation, and Affymetrix Hu95Av microarray hybridization were performed by this independent group. Together with the expression data for each sample, information about the tumor including age of patient, PSA at diagnosis, clinical stage at diagnosis, and Gleason score was provided. Outcome data was not available.

To validate the models predicting unknown prostate samples as either tumor or normal, the initial set of 102 genes was used to identify the "n" genes (either 4 or 16 in this experiment) with expression best distinguishing between tumor and normal tissue in leave-one-out cross validation. The expression of these genes in the unknown sample was then compared to the 102 tumors using knn analysis and the identity was predicted (based on the identity of the 3 closest known samples).

Initially, the mean gene expression values across the two sets of files (the initial 102 samples and the 35 sample validation set) were significantly different presumably as a result of technical variation. To minimize these differences tumor normal prediction testing was performed on both raw and normalized data. During normalization, the mean expression of each gene is set at 0 and the level of each gene's expression in each sample is recalculated as the number of standard deviations away from the mean expression (set at 0). When the 4 or 16 gene models were used to predict the identity of the novel 35 samples, the minimum success rate was 77% and the maximum success rate was 86% (FIG. 6). Thus, the outcome model successfully predicted the tumor/normal identity of unknown samples in a completely independent surgical cohort despite significant technical hurdles.

Example 8

Correlation of Gene Expression with Epithelial Content

Figures 7B, 7C:
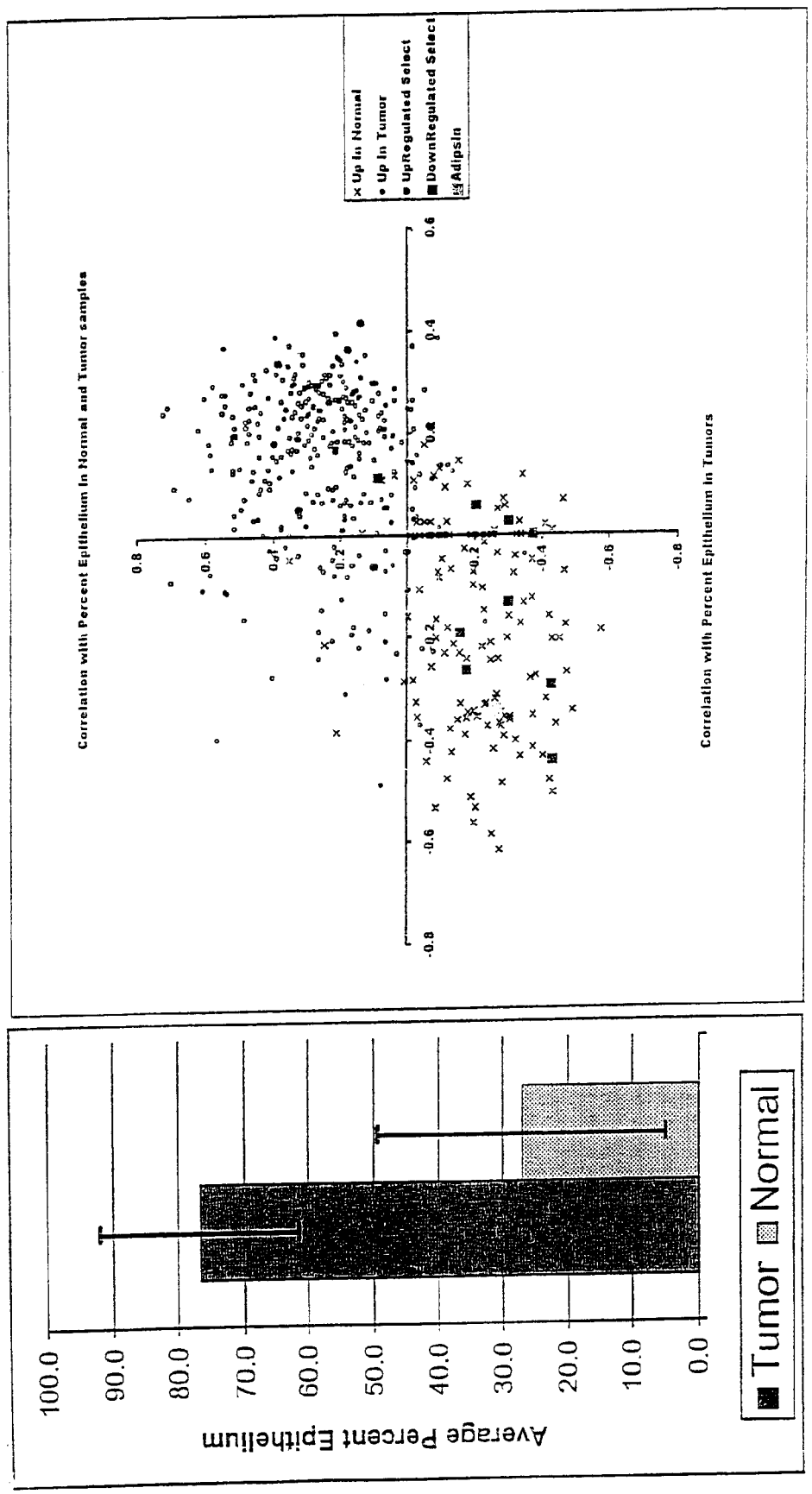
FIG. 7B is a graph of the average percent epithelium between prostate tumor and normal samples.
FIG. 7C is a graph of the correlation between gene expression and percent epithelium in tumors (x-axis) and in normal samples (y-axis) for the 456 genes that passed the initial tumor versus normal (T/N) class prediction permutation testing. The genes frequently used in a 16 gene model distinguishing between tumor and normal are depicted by dark squares (up in tumor, down in normal) and dark circles (down in tumor, up in normal).

When compared histologically, the tumor samples were found to contain a greater proportion of epithelial cells than normal counterparts. In the samples used in the studies described herein, the mean percentage of epithelium in the tumors was 78.65% (±14.27) and in the normal was 27.02 (±20.76) (p<0.0001) (FIGS. 7A and 7B). Thus, some gene transcripts may vary solely as a result of these differences in cellular composition.

To identify such genes, the Pearson coefficients for the correlation between the expression level of each gene and the epithelial content of samples (separately for normal and tumor) were calculated. For the purposes of simplicity, we assumed that samples were composed of only two elements epithelium and stroma. As such, a positive Pearson correlation coefficient indicated an association with epithelium while a negative coefficient indicated a "stromal" association. Specifically, the correlation studies were carried out as follows. The percent epithelium values from the opposing sides of each sample were averaged to a single percent epithelium value. The correlation between the expression of each gene in a given sample and the epithelial content of the sample was determined separately for both tumor and normal samples using the Pearson coefficient. Permutation testing (by randomizing the percent epithelial designations) determined the degree of correlation that would be expected by chance alone with estimated P values of 0.01, 0.05, 0.10, and 0.20. Genes with correlations to epithelial content greater than or equal to an estimated P value of 0.20 in both the tumor samples and the normal samples were identified.

The subset of 317 genes with high expression in tumors and 139 genes with high expression in normal samples were plotted according to the correlation to percent epithelium in tumor (x axis) and normal (y axis) samples (FIG. 7C). Permutation testing determined that many genes correlated with epithelial content (positive) or stromal content (negative) better than would be expected by chance alone. These genes likely represent those that are solely elevated in tumor or normal samples simply as a result of the differences in cellular composition, and can serve as biomarkers for prostate cancer. However, these genes may be less likely to represent genes directly linked to the underlying biology of tumor development. These genes are shaded in FIG. 4.

Example 9

Genes Correlating with Gleason Score

While certain distinctions or classifications (e.g., tumor versus normal) can be accurately represented as dichotomous variables it is likely that the degree of differentiation for any tumor-type represents a spectrum or range. A prostate tissue sample can be examined under a microscope by a pathologist, and a Gleason score can be determined. Upon examination of the sample by a pathologist and comparison of the sample to normal prostate tissue, a grade of one well differentiated) to five (poorly differentiated) is assigned to two dominant differentiation patterns in the sample. The sum of these is the Gleason Score (2 through 10). A lower Gleason score indicates the cells in the sample are well differentiated, and have a lower potential to be clinically significant. A higher Gleason score indicates a poorly differentiated cancer, which is more likely to be clinically significant. Generally, a Gleason score of 2, 3, or 4 indicates a well differentiated cancer with a good prognosis for survival; a Gleason score of 5, 6, or 7 indicates a moderately differentiated cancer and a prognosis ranging from good to poor, and a Gleason score of 8, 9, or 10 indicates a poorly differentiated cancer with a poorer prognosis.

To determine those genes with expression levels that most strongly associated with Gleason score, the Pearson coefficient for the correlation between the expression of each gene and Gleason score was calculated. The maximum Gleason score for each sample based on prospective histological review of opposing sides of each tumor was used for this correlation analysis. After scaling, thresholding, and filtering of the 52 tumor samples, 5254 genes remained for subsequent analysis. Because Gleason is not a dichotomous variable, the correlation between the expression of each of the 5254 genes and the maximum Gleason score of each of the 52 tumor samples was determined using the Pearson correlation coefficient. Genes were ranked according to this correlation. In order to determine the degree of correlation between gene expression and Gleason score that could be expected by chance alone, the Gleason score distinction was randomly permuted 1000 times (in a method similar to that described above for the tumor normal and percent epithelium analysis). Those genes correlating with Gleason score better than $p=0.01$ were identified. As an additional analysis, because there is great clinical interest in the distinction between tumors of Gleason score 6 and those of Gleason score 7, knn analysis was used to determine if significant differences in gene expression existed between tumor samples with Gleason score 6 (n=26) and those of Gleason score 7 (n=20). Permutation testing was used to determine if any genes matched the Gleason distinction better than would be expected by chance alone.

Figure 8:
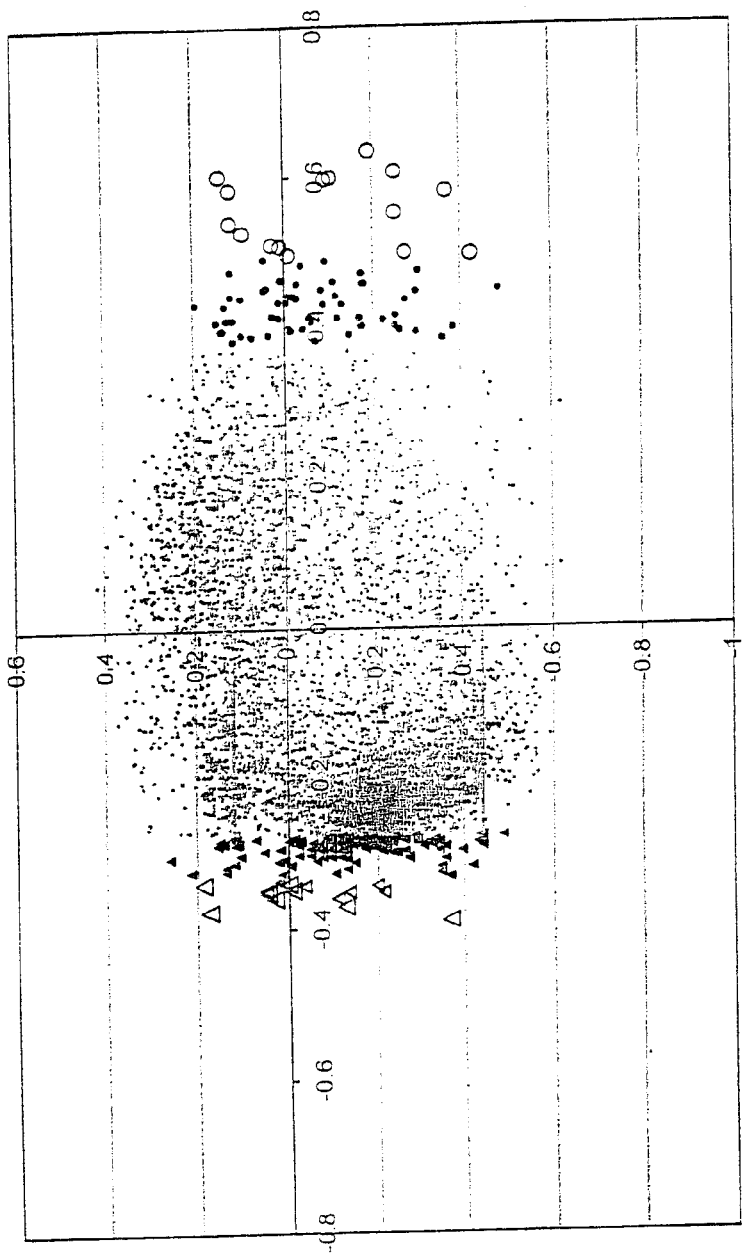
FIG. 8 is a graph of the Pearson correlation of percent epithelium in tumor samples (y-axis) compared to the maximum Gleason score (x-axis) as determined for 5254 genes. Permutation testing on data with randomized Gleason score designations revealed the Pearson correlation coefficients expected by chance alone at the 0.01 (solid circle and triangle) and 0.001 frequency (hollow circle and triangle). Genes with positive correlation greater than expected by chance alone at the 0.001 level are depicted by open circles, and genes with negative correlation with Gleason score are depicted by open triangles.

This permutation analysis revealed that the expression pattern of a group of 219 genes had a stronger correlation with Gleason score than expected by random chance alone (at the $p=0.01$ level) (FIG. 8A, all data points); 29 of these genes (FIG. 8A, ○ and Δ) had a stronger correlation with Gleason score than expected by random chance alone at the $p=0.001$ level. All genes were plotted in FIG. 8 according to their Pearson correlation with Gleason score (x axis) and their correlation with percent epithelium in the same tumor samples (y axis). A list of the 56 genes whose expression positively correlates with Gleason score at the $p=0.01$ level is provided in FIGS. 9A–9D, and a list of the 134 genes whose expression negatively correlates with Gleason score at the $p=0.01$ level is provided in FIGS. 9E–9L. A list of the 15 genes whose expression positively correlates with Gleason score at the $p=0.001$ level is provided in FIG. 10A, and a list of the 14 genes whose expression negatively correlates with Gleason score at the $p=0.001$ level is provided in FIG. 10B. These genes can be use to determine to determine the clinical significance of a prostate cancer sample. Of the genes most strongly positively associated with Gleason score, several are putative TGF-beta targets including SPARC/osteonectin, IGFBP3, Collagen Type 1 Alpha 2, Follistatin-related protein and biglycan. As a group, these genes had a negative correlation with the percentage of epithelium in tumors suggesting that they represent a class of coordinately regulated tumor stromal genes.

Figure 11A:
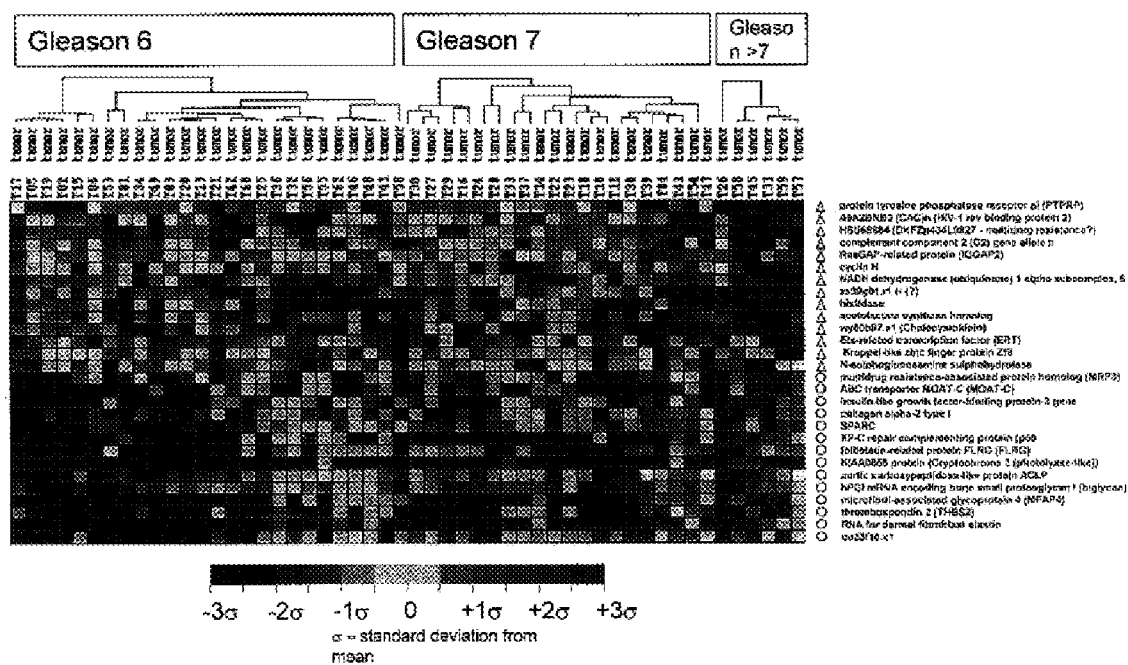
FIG. 11A is a hierarchical clustering within similar Gleason score (Gleason 6, 7, and greater than 7) of genes passing permutation testing at the 0.001 level (see FIG. 8).

The expression of the above described 29 genes that most closely correlated with Gleason score at $p=0.001$ was subsequently used to organize prostate tumors by hierarchical clustering within each Gleason score category (Gleason score 6, Gleason score 7, or Gleason score greater than 7) and were ranked by their Pearson correlation coefficient (FIG. 11A). A recurring problem in prostate cancer is that tumors of intermediate Gleason scores (6 and 7) have significantly varied behavior. As this gene set organized the prostate cancer tumors within both the Gleason score 6 and 7 tumors into roughly two groups, the overlapping behavior of these tumors may be partially explained by the expression of these genes, and perhaps by differences in TGF-β signaling.

Figure 11B:
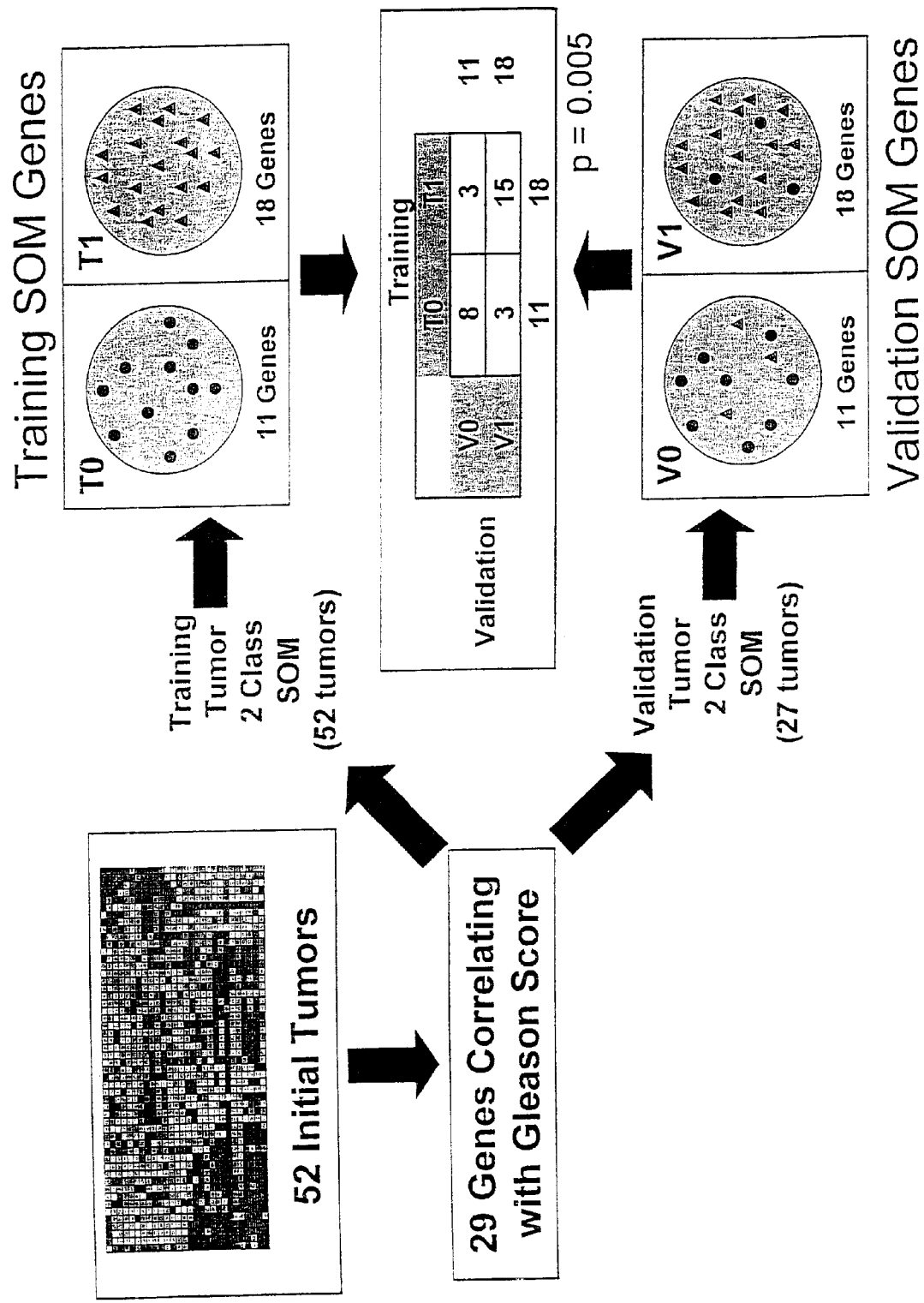
FIG. 11B is a schematic representation of the reproducibility of the determination of genes most strongly correlated with Gleason score.

To test the reproducibility of the observed organization, the same genes were used to organize the 27 validation tumors described in Example 7. If this organization represents a reproducible phenotype, then these genes should drive the organization of an independent tumor set into two groups and recapitulate a similar gene expression pattern. To test this, the independent tumors were separated into a two clusters (5 and 22 members) SOM using the 29 genes best correlated with Gleason score (FIG. 11B). The organization of genes within these two clusters significantly reproduced the original findings (p=0.006 by Fisher's Exact Test). In addition, the TGF-beta targets were again associated with the cluster of tumors tending to have a higher Gleason score.

Example 10

Clinical Outcome Prognosis

Prostate cancer recurrence after prostatectomy is thought to result from the presence of micrometastatic foci present outside the gland at the time of surgery. It is unclear whether such micrometastases result from a stochastic and unpredictable process or are tightly linked to the intrinsic biological behavior of the tumor. Biological differences might be reflected in the expression differences among tumors that recur versus those that do not. To determine whether such differences could be found we looked for expression patterns that differentiated the tumors obtained from patients who ultimately relapsed following surgery from those tumors taken from individuals who remained free of disease for at least 4 years. It was felt that a 4 year disease free survival period would exclude the majority of tumors from patients ultimately destined to relapse from the non-relapse pool.

Based on these criteria of the 52 samples, sufficient clinical follow-up data was available for 8 recurrent and 13 non-recurrent tumors, where the individual from whom the tumor had been removed either had biochemical recurrence or remained free of disease (based on a PSA=0.1) at least 48 months after radical prostatectomy. From this group of tumors, genes whose expression was most strongly associated with disease outcome were identified using nearest neighbor analysis and class prediction. After scaling all present genes, thresholding, and filtering, 5505 genes remained for subsequent analysis. Using these genes, knn and leave-one-out cross validation was used to determine if the individual expression of any gene matched the recurrent/nonrecurrent class distinction better than expected by chance alone and if the expression of any group(s) of genes predicted recurrence following radical prostatectomy better than expected by chance alone.

Figures 12A, 12B:
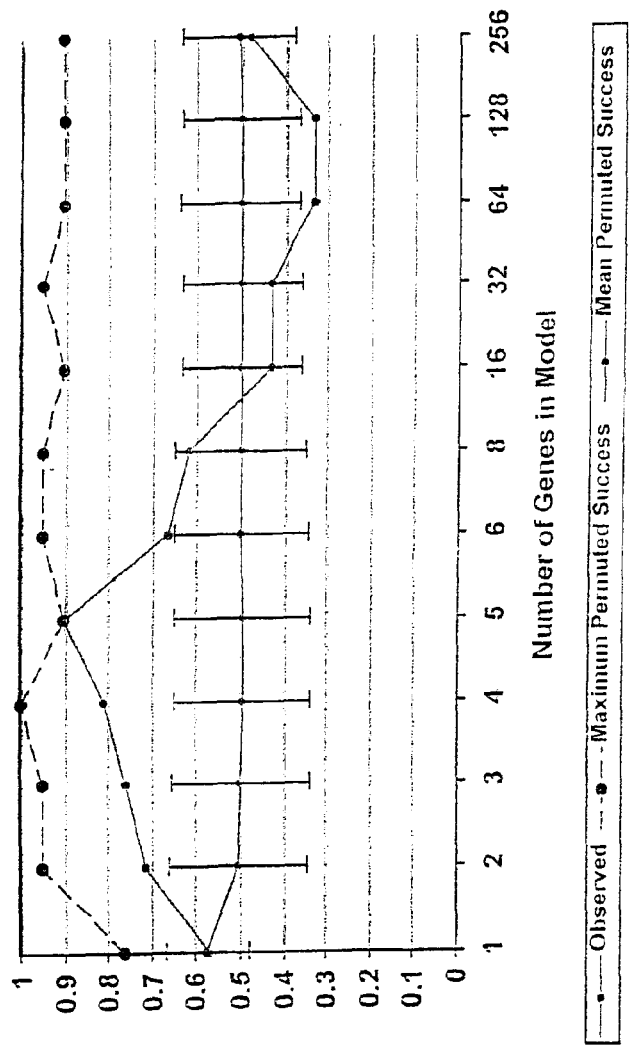
FIG. 12A is a graph of the predictability of an outcome prediction model for prostate cancer based on the number of genes used in the model.
FIG. 12B is a list of the five genes used in the 5-gene model of prostate cancer outcome prediction. Platelet Derived Growth Factor Receptor, Beta Chromogranin A, and HOXC6 showed increased expression in recurrent tumors, while Inositol Triphosphate Receptor Type 3, and Beta Galactoside Sialotransferase show decreased expression in recurrent tumors, compared to controls.

The above analysis showed that a 5-gene model measuring expression of Platelet Derived Growth Factor Receptor, Beta Chromogranin A, HOXC6, Inositol triphosphate receptor, type 3, and Beta Galactoside Sialotransferase outperformed all other prediction models (FIG. 12A). Platelet Derived Growth Factor Receptor, Beta Chromogranin A, and HOXC6 showed increased expression in recurrent tumors, while Inositol Triphosphate Receptor Type 3, and Beta Galactoside Sialotransferase show decreased expression in recurrent tumors, compared to controls. Unlike the tumor/normal prediction model, there was no gene model that bested the results from random permutation of the class distinctions. However, the results of the 5-gene model, which made 2 errors out of the 21 samples, was only surpassed by the random permutation analysis at a rate of 0.002 within all 5-gene models tested and a rate of 0.037 for all gene models tested. Thus, the 5-gene model developed using these samples is unlikely due to chance alone with an estimated p-value of 0.037 after correcting for the testing of multiple gene models within the same data set.

One possibility is that the clinical characteristics of the recurrent and non-recurrent patients (such as serum PSA, Gleason Score or Tumor T stage) might have accounted entirely for the differences in patient outcome. This however, was not the case, as there were minimal differences and none that were statistically significant in any of these clinical characteristics between patients who recurred and those who did not recur (see FIG. 1).

Four of the five genes (FIG. 12B) whose expression was used by this model have been implicated in the pathogenesis of human cancer. While none of these genes can independently separate non-recurrent versus recurrent tumors, Chromogranin A was one of the 5 genes and its detection by immunohistochemistry has previously been reported to associate with recurrent disease (Borre, et al. (2000), Clin. Cancer Res. 6: 1882–90). While our sample size was too small to validate Chromogranin A expression as an independent predictor of outcome in our tumor samples, immunohistochemistry for Chromogranin A was performed in our samples as follows. Tissue samples were fixed in buffered 10% formalin, embedded in paraffin, and used to construct a tissue microarray (TMA) as described previously (Simon et al., J. Natl. Cancer Inst. 93: 1141–1146 (2001)). Briefly, hematoxylin-eosin-stained sections were made from each selected primary tumor block (donor blocks) to define representative tumor regions. Five tissue cylinders (0.6 mm in diameter) were then punched from two regions of the donor block representative of the overall Gleason score recorded in the final pathology report using a microarray instrument (Beecher Instruments, Silver Spring, Md.). Five normal areas, five prostate intraepithelial neoplasia (PIN) (when present) and five tumor areas were arrayed for each patient. Tissues cylinders were placed in five 25-mm×35-mm paraffin blocks to produce the TMA blocks utilized for immunohistochemistry and in situ hybridization. The resulting TMA blocks were cut into 5 µm sections that were transferred to glass slides. A separate section from each of the five complete sets of TMA blocks was used for riboprobe immunohistochemical analysis.

Immunostaining was performed as previously described (Signoretti et al., Am. J. Pathol. 154: 67–75 (1999); and Signoretti et al., J. Natl. Cancer Inst. 92: 1918–1925 (2000)) in all tissue specimens using the following primary antibodies: Chromogranin A (Dako, Carpinteria, Calif.) at 1:200 dilution, Fatty Acid Synthase (Upstate Biotechnology, Lake Placid, N.Y.) at 1:50 dilution, and Ep-Cam (323/A3, BioGenex, San Ramon, Calif.) at 1:50 dilution. Five micron sections of the tissue array slides were deparaffinized, rehydrated and microwaved in 10 mmole/L citrate buffer, pH 6.0 (BioGenex, San Ramon, Calif.) in a 750 W oven for 15 minutes. The primary antibody was applied at RT in the automated stainer (Optimax Plus 2.0 bc, BioGenex, San Ramon, Calif.). Detection steps were performed by the instrument utilizing the MultiLink-HRP kit (BioGenex, San Ramon). Standardized 3,3 diaminobenzidine (DAB) development times allowed accurate comparison of all samples. Substitution of the primary antibody with phosphate buffered saline (PBS) served as negative staining control.

Of the tumors staining highest for Chromogranin A, the top two were recurrent disease. PDGFR-beta was used in this model and its expression was high in our recurrent samples. Others have previously reported elevated expression of PDGF-R beta in metastatic prostate cancer samples and together these data raise the possibility that the PDGFR pathway may be important in the progression of prostate cancer.

Example 11

Expression Differences Between Specific Pathological Features and Measures of Local Invasion The annotated database including the clinical and pathological features of the tumors included in this study allowed us to determine if significant expression patterns differentiated between the presence or absence of specific pathological features. We performed nearest neighbor analysis to determine if the expression of any genes matched the distinction between present or absent capsular penetration, positive or negative margins, and the presence or absence of perineural invasion better than would be expected by chance alone.

Patients whose prostate cancer specimens demonstrate capsular penetration or have positive surgical margins are more likely to recur following surgery. It is unclear whether capsule penetration is a stochastic process having more to do with tumor volume and time to diagnosis or, alternatively, whether prostate tumors that penetrate the capsule differ biologically from those that do not. If the latter is true we hypothesized that significant differences in gene expression would be found that distinguish penetrant from non-penetrant tumors. In this analysis, no genes passed permutation testing (even at the 5% level) during class distinction when tumors were separated with respect to the presence or absence of capsular penetration, present or absent perineural invasion, and positive or negative surgical margins. These data suggest the possibility that these characteristics may be more dependent on factors such as time to diagnosis, tumor volume or surgical technique rather than inherent differences in tumor biology.

Example 12

Additional Gleason Gene Analyses

In order to successfully model outcome using gene expression in prostate cancer, several methods have been applied to choose genes to include in the correlated with prostate cancer. One approach, is to first identify those genes that have expression correlated with Gleason sum and then use the expression of these genes to stratify tumors of known outcome.

For this analysis, each tumor used in the study was evaluated by a single pathologist and assigned a Gleason score. Then the Gleason score for each sample was used as an independent variable and the correlation between the Gleason score and gene expression for each gene on Affymetrix microarrays (Affymetrix, Santa Clara, Calif.) were determined. To determine what degree of correlation was better than that expected by chance alone, permutation testing was used which randomized Gleason score assignment within the same dataset and then recalculated the correlation between each gene's expression and the randomly permuted labeled. Using this method (described, as described herein), one can understand what degree of correlation can be expected by chance alone.

Figure 13:
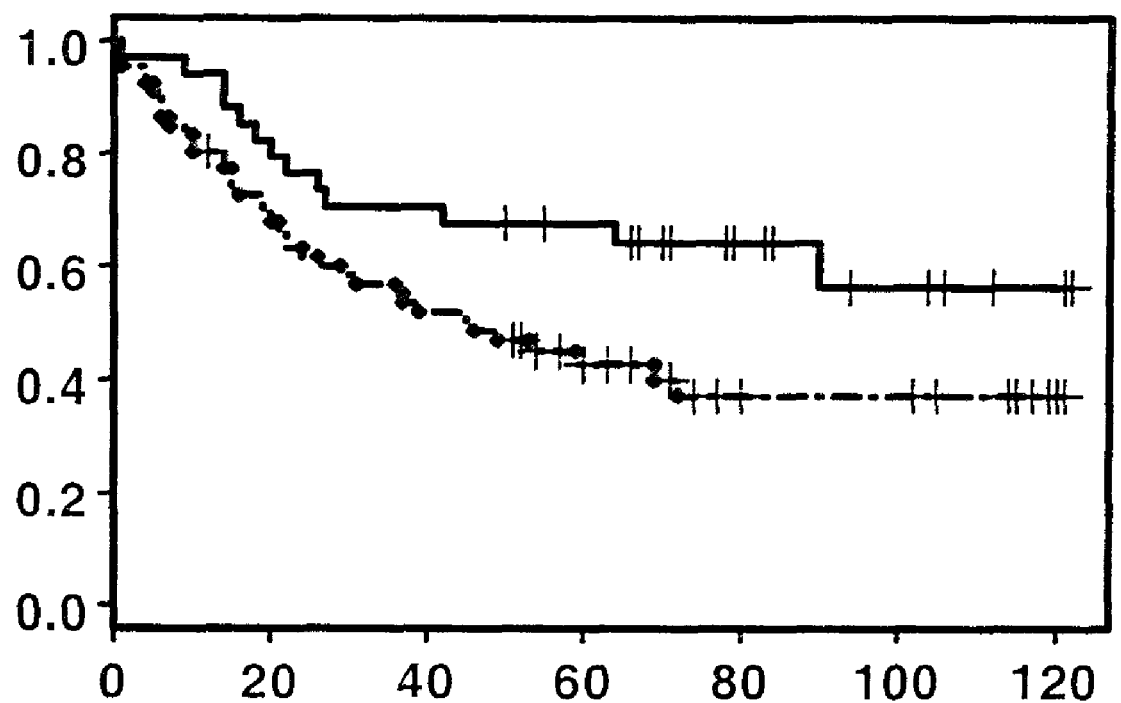
FIG. 13 is a Kaplan Meir curve of the correlation of genes expressed in prostate cancer with Gleason score.

Genes correlating with the Gleason score better than expected at a P value of 0.001 in the initial set of 52 tumors, described in Example 7, were then used to stratify a training set of 100 tumors (18 of which were from the initial 52 and 82 of which were not previously tested). As demonstrated in the Kaplan Meir curve (FIG. 13), the genes having expression correlating with Gleason score could stratify tumor with respect to outcome (p=0.03).

This analysis has been continued to refine the list of genes correlating with Gleason score. The same analysis described above was performed on the initial 52 tumors as well as on the 82 independent tumors. The genes correlating with Gleason score at a P value of 0.05 or less in both independent sets are provided in FIGS. 14A–14E. The Unigene Accession number and the ProbSet ID number (Affymetrix numbers) can be used to obtain the sequence of the gene from GenBank, Swissprot or other sequence databases that are also available. These genes, either independently or used coordinately, are likely to stratify samples with respect to outcome. Significantly, 3 of the genes mentioned in the 5 gene model of outcome described herein (PDGFRbeta, HoxC6, and Sialyltransferase 1) are included in this list, underscoring the value of these genes in predicting outcome following radical prostatectomy.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying prostate cancer comprising determining a gene expression profile from a gene expression product of at least one prostate cancer identification informative gene having increased expression in prostate cancer in a sample from prostate tissue,
wherein said at least one prostate cancer identification informative gene is HOXC6;
and wherein increased expression of said gene expression product in said sample is indicative of prostate cancer.

2. A method of predicting the likelihood of prostate cancer development in a subject, comprising determining a gene expression profile from a gene expression product of at least one informative gene having increased expression in prostate cancer in a sample, derived from prostate tissue;
wherein said at least one prostate cancer identification informative gene is HQXC6;
and wherein increased expression of said gene in said sample indicates an increased likelihood of prostate cancer development in the subject.

3. A method of diagnosing prostate cancer in a subject, comprising determining a gene expression profile from a gene expression product of at least one informative gene having increased expression in prostate cancer in a sample from prostate tissue;
wherein said at least one prostate cancer identification informative gene is HOXC6;
and wherein increased expression of said gene in said sample indicates the presence of prostate cancer in said subject.

4. The method of any one of claims 1, or 2, or 3, comprising further determining a gene expression profile from a gene expression product of at least one additional prostate cancer identification informative gene having increased expression in prostate cancer, wherein said prostate cancer identification informative gene is selected from the group consisting of:
the genes identified by UniGene Cluster Nos. Hs.154424, Hs.823, Hs.79037, Hs.112259, Hs.82280, Hs.4815, Hs.149923, Hs.164280, M21535, Hs.75655, X17620, Hs.574, Hs.182426, Hs.7780, Hs.90336, Hs.25640, Hs.149923, Hs.38972, Hs.83190, Hs.164280, Hs.163593, Hs.73742, Hs.753109, Hs.28491, Hs.182527, Hs.79217, Hs.79093, Hs.10247, Hs.56145, Hs.182979, Hs.2795, Hs.76230, Hs.119122, Hs.181634, Hs.10082, Hs.183698, Hs.75432, Hs.76136, Hs.180842, Hs.227823, Hs.158675, Hs.69469, Hs.75362, Hs.91011, Hs.111029, Hs.155560, Hs.180911, Hs.21543, Hs.1832, Hs.118690, Hs.75212, Hs.22751 1, Hs.155048, Hs.106778, Hs.65114, Hs.174131, Hs.178551, Hs.153177, Hs.146763, Hs.75538, Hs.133230, Hs.105440, Hs.186570, Hs.184270, Hs.83383, Hs.8752, Hs.146763, Hs.76422, Hs.135, Hs.76698, Hs.I 117950, Hs.74267, Hs.89529, Hs.5662, Hs.83753, Hs.2953, Hs.1708, Hs179516, Hs.110029, Hs.76285, Hs.4112, Hs.3491, Hs.56845, Hs.5174, Hs.1197, Hs.6727, Hs.75525, Hs.161002, Hs.75471, Hs.1066, Hs.75139, Hs.76194, Hs.180450, Hs.75207, Hs.61273, Hs.51299, Hs.111611, Hs.234489, Hs.6456, Hs.178391, Hs.16492, Hs.75458, Hs.75459, Hs.82202, Hs.25846, Hs.70337, Hs.180946, Hs.198951, Hs.74861, Hs.179779, Hs.4193, Hs.184776, Hs.158675, Hs.174140, Hs.61635, Hs.126701, Hs.75789, Hs.848, Hs.6895, Hs.8603, Hs.5809, Hs.170250, Hs.31130, Hs.172089, Hs.286, Hs.699, Hs.179943, Hs.165590, Hs.75724, Hs.180414, Hs.75746, Hs.75616, Hs.234518, Hs.80617, Hs.182825, Hs.184582, Hs.181350, Hs.76067, Hs.13456, Hs.70830, Hs.155356, Hs.163867, Hs.130227, Hs.84072, Hs.3297, Hs.5662, Hs.119252, Hs.10842, Hs.79081, Hs.49346, Hs.18953, Hs.1948, Hs.136644, Hs.7306, Hs.4437, Hs.182740, Hs.76064, Hs.6574, Hs.118065, Hs.211824, Hs.154890, Hs.154103, Hs. 106711, Hs. 129548, Hs.180737, Hs.79, Hs.74276, Hs.185057, Hs.169301, Hs.31439, Hs.118638, Hs.172182, Hs.75914, Hs.9950, Hs.82148, Hs.78614, Hs.203907, Hs.73818, Hs.82148, Hs.2953, Hs.166033, Hs.119076, Hs.5174, Hs.66762, Hs.181243, Hs.06673, Hs.55682, Hs.9701, Hs.183109, Hs.75344, Hs.119387, Hs.113029, Hs.119598, Hs.75722, Hs.93304, Hs.120856, Hs.184014, Hs.169793, Hs.234705, Hs.75618, Hs.5957, Hs.63552, Hs.74405, Hs.75744, Hs.118836, Hs.105465, Hs.177559, Hs.7771, Hs.173205, Hs.157850, Hs.101025, Hs.70830, Hs.3128, Hs.28757, Hs.77290, Hs.32317, Hs.9235, Hs.12770, Hs.114360, Hs.15071, Hs.184582, Hs.8123, Hs.83753, Hs.17144, Hs.3709, Hs.145279, Hs.30965, Hs.182429, Hs.89674, Hs.91747, Hs.74624, Hs.84359, Hs.74407, Hs.28914, Hs.182371, Hs.7314, Hs.77257, Hs.182937, Hs.75607, Hs.238542, Hs.93659, Hs.84131, Hs.76847, Hs.49767, Hs.98732. Hs.15832, HS.75410, Hs.180352, Hs. 41569, Hs.2642, Hs.75893, Hs.121017, Hs.878, Hs.109201, Hs.109752, Hs.7936, Hs.3462, Hs.199263, Hs.94466, Hs.83532, Hs.230, Hs.166152, Hs.11223, Hs.4890, Hs.91379, Hs.1624, Hs.6396, Hs.234518, Hs.89643, Hs.51860, Hs.S5971, Hs.S52721, Hs.S5591, Hs.S1908, Hs.S3389, Hs.S2453, Hs.S3950, Hs.S81622 1, Hs.S6082, Hs.S5945, Hs.S569401, Hs.S417477, Hs.54651, Hs.S572086, Hs.S268597, Hs.S1369068, Hs.70823, Hs.77290, Hs.82226, Hs.118162, Hs.80988, Hs.129872, Hs.179573, Hs.178551, Hs.178728, Hs.142827, Hs.271473, Hs.77054, Hs.7969 1, Hs.154424, Hs.75860, Hs.82932, Hs.82163, Hs.125078, Hs.85181, Hs.26077, Hs.1255, Hs.79, Hs.80768, Hs.89781, Hs.75916, Hs.194673, Hs.74368, Hs.83920, Hs.18593, Hs.146550, Hs.198281, Hs.814, Hs.10247, Hs.75074, Hs.2064, Hs.279554, Hs.76884, Hs.119529, Hs.182366, Hs.179573, Hs.25348, Hs.90786, Hs.I 18397, Hs.77326, Hs.108660, Hs.108623, Hs.203917, Hs.7278, Hs.118223, Hs.17409, Hs.111779, Hs.11494, Hs.821, Hs.178658, Hs.288869, Hs.75248, Hs.288031, Hs.108623, Hs.1650, Hs.287820, Hs.111779, Hs.178551, Hs.182825, Hs.7252, Hs.75447, Hs.31130, Hs.172182, Hs.306965, Hs.83920, Hs.83920, Hs.76144, Hs.76144, Hs.142827, Hs.302649, Hs.302649, Hs.347991, Hs.29131, Hs.8546, Hs.75283, Hs.6909, Hs.82045, Hs.82045, Hs.83337, Hs.70823, Hs.119206, Hs.119206, Hs.77326, Hs.76884, Hs.268371, Hs.820, Hs.82226, Hs.334695, Hs.287820, Hs.58189, Hs.2642, Hs.243901, Hs.18593, Hs.111680, Hs.76753, Hs.184693, Hs.9295, Hs.9295, Hs.351875, Hs.70327, Hs.17409, Hs.344027, Hs.179573, Hs.179573, Hs.179573, Hs.81800, Hs.81800, Hs.1584, Hs.1584, Hs.77054, Hs.108660, Hs.108660, Hs.169401, Hs.268571, Hs.118397, Hs.72157, Hs.111222;

the genes identified by GenBank Accession Nos. D14530, X58965, U37518, J04152, M55409, M14199, M99487, U 51004, Z97630, J02783, X63527, U21090, M22430, L19686, U41060, M64241, M1 1353, X56468, U95006, U18321, D38047, AL035252, M21154, D13748, M55914, M34309, U70063, D38048, AB000584, X73066, AL021546, U76604, X15187, AL034374, M84711, X00734, M33764, M21154, M99487; M93036;

the genes identified by hybridization to probe 1513_at, 1173_g at, 179_at, 1180_g_at, 296_at, 1840_g_at or 324_f_at in the Affymetrix® Human Genome U95Av2 Array;

platelet derived growth factor receptor beta, and chromogranin A.

5. The method of claim 2, 3, or 4, comprising further determining a gene expression profile from a gene expression product of at least one prostate cancer identification informative gene having decreased expression in prostate cancer, wherein said at least one prostate cancer identification informative gene is selected from the group consisting of:

the genes identified by UniGene Cluster Nos. Hs.155597, Hs.8272, Hs.79389, Hs.236327, Hs.101850, Hs.7974, Hs.8022, Hs.81256, Hs.80395, Hs.85087, Hs.106070, Hs.173594, Hs.2463, Hs.18586, Hs.1940, Hs.166072, Hs.211819, Hs.56045, Hs.30250, Hs.9552, Hs.117782, M98539, Hs.6349, Hs.9999, Hs.76688, Hs.173381, Hs.78065, Hs.156007, Hs.95420, Hs.80206, Hs.220056, Hs.75350, Hs.9651, Hs.75586, Hs.8025, Hs.6606, Hs.75106, Hs.85155, Hs.104105, Hs.66392, Hs.82794, Hs.29736, Hs.77546, Hs.171595, Hs.226795, Hs.112844, Hs.7833, Hs.160483, Hs.227716, Hs.93557, Hs.74034, Hs.106826, Hs.82001, Hs.19180, Hs.20060, Hs.3407, Hs.81047, Hs.25511, Hs.9208, Hs.8402, Hs.137569, Hs.37682, Hs.154721, Hs.46659, Hs.1640, Hs.35094, Hs.76536, Hs.231884, Hs.65424, Hs.78989, Hs.184724, Hs.198689, Hs.109438, Hs.79386, Hs.48998, Hs.126084, Hs.29802, Hs.80552, Hs.35861, Hs.170133, Hs.74070, Hs.14896, Hs.84883, Hs.82749, Hs.82109, Hs.10351, Hs.114346, Hs.160318, Hs.20084, Hs.12956, Hs.21851, Hs.75807, Hs.4217, Hs.202097, Hs.239587, Hs.7835, Hs.77448, Hs.76884, Hs.20144, Hs.118796, Hs.234680, Hs.13999, Hs.79844, Hs.75899, Hs.170279, Hs.188882, Hs.21858, Hs.78629, Hs.134932, Hs.107164, Hs.82223, Hs.19368, Hs.50130, Hs.105584, Hs.78501, Hs.6139, Hs.225936, Hs.195432, Hs.155122, Hs.35094, Hs.167740, Hs.8762, Hs.155119, Hs.47431, Hs.8309, Hs.1473, Hs.158348, Hs.845, Hs.200188, Hs.123659, Hs.161166, Hs.180533, Hs.79844, Hs.214142, Hs.82128, Hs.79101, Hs.170917, Hs.76873, Hs.99877, Hs.36975, Hs.234759, Hs.12256, Hs.194143, Hs.94581, Hs.46329, Hs.77578, Hs.181202, Hs.76719, Hs.258850, Hs.195484, Hs.75180, Hs.2025, Hs.110746, Hs.211562, Hs.2726, Hs.5457, Hs.121478, Hs.250773, Hs.9059, Hs.21894, Hs.124029, Hs.169401, Hs.80261, Hs.122575, Hs.126256, Hs.51, Hs.278540, Hs.79432, Hs.203, Hs.37501, Hs.194657, Hs.7678, Hs.49378, Hs.158297, Hs.95243, Hs.1372, Hs.27973, Hs.12513, Hs.84, Hs.272951, Hs.123125, Hs.66542, Hs.166361, Hs.156115, Hs.199179, Hs.24103, Hs.2664, Hs.173894, Hs.23294, Hs.274295, Hs.4764, Hs.155987, Hs.35861, Hs.69171, Hs.80343, Hs.78765, Hs.69351, Hs.66774, Hs.99877, Hs.89499, Hs.96744, Hs.184194, Hs.23964, Hs.2994, Hs.6441, Hs.89633, Hs.635, Hs.1074, Hs.143522, Hs.137570, Hs.227473, Hs.23777, Hs.172670, Hs.158029, Hs.166074, Hs.26837, Hs.29287, Hs.250615, Hs.172690, Hs.180034, Hs.154846, Hs.239459, Hs.158112, Hs.180224, Hs.4278, Hs.4105, Hs.25333, Hs.79353, Hs.79241, Hs.90419, Hs.19261, Hs.155140, Hs.50964, Hs.40300, Hs.123090, Hs.103915, Hs.95197, Hs.2316, Hs.239926, Hs.248059, Hs.44131, Hs.54413, Hs.13531, Hs.105924, Hs.250616, Hs.340, Hs.77889, Hs.92614, Hs.236774, Hs.2860, Hs.75438, Hs.172674, Hs.1378, Hs.183037, Hs.179574, Hs.5105, Hs.183752, Hs.158164, Hs.169849, Hs.4055, Hs.31074, Hs.274416, Hs.514, Hs.166096, Hs.78993, Hs.154762, Hs.2253, Hs.55879, Hs.166051, Hs.78880, Hs.74624, Hs.80247, Hs.771 83, Hs.77183, Hs.23582, Hs.14894, Hs.2025, Hs.158287, Hs.2316, Hs.2554, Hs.138860, Hs.26550, Hs.35861, Hs.74624, Hs.152978, Hs.96744, Hs.2860, Hs.117780, Hs.93841, Hs.31074, Hs.5025, Hs.78344, Hs.183752, Hs.183752, Hs.283655, Hs.93199, Hs.177664, Hs.103915, Hs.89868, Hs.171995, Hs.171995, Hs.190913, Hs.250616, Hs.82112, Hs.78877, Hs.22111, Hs.3268, Hs.115352, Hs.155546, Hs.306122, Hs.343871, Hs.336920, Hs.2704, Hs.77889, Hs.183738, Hs.159543, Hs.166096, Hs.103854, Hs.2253, Hs.173894, Hs.164410, Hs.80247, Hs.76722, Hs.12, Hs.50964, Hs.287921, Hs.75462, Hs.193163, Hs.193163, Hs.31210, Hs.176658, Hs.75741, Hs.95197, Hs.154721, Hs.1852, Hs.194750, Hs.419, Hs.158029, Hs.323053, Hs.323053, Hs.323053, Hs.323053, Hs.128425, Hs.166079, Hs.166079, Hs.301373, Hs.117729, Hs.289106, Hs.169848, Hs.239, Hs.2780, Hs.336920;

the genes identified by GenBank Accession Nos. D00017, M96233, X14885, L07594, U04313, X57025, L13720, X02958, L24203, U21689, U93305, M14752, L37112;

the genes identified by hybridization to probe 1664_at or 40735_at in the Affymetrix® Human Genome U95Av2 Array;

inositol triphosphate receptor type 3 and beta galactoside sialotransferase;

wherein increased expression of HOXC6 and decreased expression of at least one of the prostate cancer identification informative genes identified in this claim is indicative of prostate cancer.

6. The method of claim 1, 2, 3, 4, or 5, wherein said method comprises determining the gene expression profile from the gene expression product of at least four prostate cancer identification informative genes.

7. The method of claim 1, 2, 3, 4, or 5, wherein said method comprises determining the gene expression profile from the gene expression product of at least sixteen prostate cancer identification informative genes.

* * * * *

UNITED STATES PATENT AND TRADEMARK OFFICE
CERTIFICATE OF CORRECTION

PATENT NO. : 6,949,342 B2  Page 1 of 1
DATED : September 27, 2005
INVENTOR(S) : Golub et al.

It is certified that error appears in the above-identified patent and that said Letters Patent is hereby corrected as shown below:

Column 44,
Line 58, "Hs.753109" should read -- Hs.75309 --.
Line 67, "Hs.I 117950" should read -- Hs.117950 --.

Column 45,
Line 23, "Hs.06673" should read -- Hs.106673 --.
Line 41, "Hs.S81622" should read -- Hs.816221 --.
Line 43, "Hs.S4651" should read -- Hs.54651 --.
Line 43, "Hs.I 18397" should read -- Hs.118397 --.

Signed and Sealed this

Fourteenth Day of March, 2006

JON W. DUDAS
*Director of the United States Patent and Trademark Office*